(12) United States Patent
Selsted et al.

(10) Patent No.: US 7,119,070 B2
(45) Date of Patent: Oct. 10, 2006

(54) ANTIMICROBIAL THETA DEFENSINS, ANALOGS THEREOF, AND METHODS OF USE

(75) Inventors: Michael E. Selsted, Irvine, CA (US); Dat Q. Tran, Anaheim, CA (US)

(73) Assignee: The Regents of the University of California, Oakland, CA (US)

( * ) Notice: Subject to any disclaimer, the term of this patent is extended or adjusted under 35 U.S.C. 154(b) by 76 days.

(21) Appl. No.: 10/427,715

(22) Filed: Apr. 30, 2003

(65) Prior Publication Data

US 2004/0014669 A1 Jan. 22, 2004

Related U.S. Application Data

(60) Provisional application No. 60/377,071, filed on Apr. 30, 2002.

(51) Int. Cl.
*A61K 38/00* (2006.01)
*A61K 38/01* (2006.01)
*A61K 38/04* (2006.01)
*A61K 38/10* (2006.01)

(52) U.S. Cl. .......................................... 514/13; 514/12
(58) Field of Classification Search ...................... None
See application file for complete search history.

(56) References Cited

U.S. PATENT DOCUMENTS

| | | | |
|---|---|---|---|
| 4,543,252 A | 9/1985 | Lehrer et al. |
| 4,659,692 A | 4/1987 | Lehrer et al. |
| 4,705,777 A | 11/1987 | Lehrer et al. |
| 5,242,902 A | 9/1993 | Murphy et al. |
| 5,324,716 A | 6/1994 | Selsted et al. |
| 5,422,424 A | 6/1995 | Selsted et al. |
| 5,459,235 A | 10/1995 | Selsted et al. |
| 5,464,823 A | 11/1995 | Lehrer et al. |
| 5,547,939 A | 8/1996 | Selsted |
| 5,633,229 A | 5/1997 | Kokryakov et al. |
| 5,693,486 A | 12/1997 | Lehrer et al. |
| 5,708,145 A | 1/1998 | Lehrer et al. |
| 5,731,149 A | 3/1998 | Selsted et al. |
| 5,804,553 A | 9/1998 | Kokryakov et al. |
| 5,804,558 A | 9/1998 | Lehrer et al. |
| 5,821,224 A | 10/1998 | Selsted et al. |
| 5,840,498 A | 11/1998 | Selsted et al. |
| 5,844,072 A | 12/1998 | Selsted et al. |
| 5,889,152 A | 3/1999 | Kokryakov et al. |
| 5,916,872 A | 6/1999 | Chang et al. |
| 5,994,306 A | 11/1999 | Chang et al. |
| 6,043,220 A | 3/2000 | Chang et al. |
| 6,159,936 A | 12/2000 | Lehrer et al. |
| 6,307,016 B1 | 10/2001 | Lehrer et al. |
| 6,335,318 B1 | 1/2002 | Selsted et al. |
| 6,492,328 B1 | 12/2002 | Lehrer et al. |
| 6,514,727 B1 | 2/2003 | Selsted et al. |
| 6,653,442 B1 | 11/2003 | Chang et al. |
| 6,713,078 B1 | 3/2004 | Lehrer et al. |

FOREIGN PATENT DOCUMENTS

| | | |
|---|---|---|
| WO | WO 96/16075 | 5/1996 |
| WO | WO 97/08199 | 6/1997 |
| WO | WO 99/11663 | 3/1999 |
| WO | WO 99/13080 | 3/1999 |
| WO | WO 00/12842 | 5/2000 |
| WO | WO 03/105883 | 12/2003 |

OTHER PUBLICATIONS

Ahmad et al., "Liposomal entrapment of the neutrophil-derived peptide indolicidin endows it with in vivo antifungal activity," *Biochemica et Biophysica Acta* 1237:109-114 (1995).
Bals et al., "Mouse β-Defensin 1 Is a Salt-Sensitive Antimicrobial Peptide Present in Epithelia of the Lung and Urogenital Tract," *Infect. Immun.* 66(3):1225-1232 (1998).
Blond et al., "The cyclic strucutre of microcin J25, a 21-residue peptide antibiotic form *Escherichia coli*," *Eur. J. Biochem.* 259:747-755 (1999).
Derua et al., "Analysis of the Disulfide Linkage Pattern in Circulin A and B; HIV-Inhibitory Macrocyclic Peptides," *Biochem. Biophys. Res. Commun.* 228:632-638 (1996).
Gålvez et al., "Purification and Amino Acid composition of Peptide Antibiotic AS-48 Produced by *Streptococcus* (*Enterococcus*) *faecalis* subsp. *liquefaciens* S-48," *Antimicrob. Agents Chemother.* 33(4):437-441 (1989).
Goldman et al., "Human β-Defensin-1 Is a Salt-Sensitive Antibiotic in Lung That Is Inactivated in Cyctic Fibrosis," *Cell* 88:553-560 (1997).
Gustafson et al., "Circulins A and B: Novel HIV-Inhibitory Macrocyclic Peptides from the Tropical Tree *Chassalia parvifolia*," *J. Amer. Chem. Soc.* 116:9337-9338 (1994).
Lehrer and Ganz, "Antimicrobial peptides in mammalian and insect host defence," *Current Opinion Immunol.* 11(1):23-27 (1999).
Lehrer et al., "Defensins: Endogenous Antibiotic Peptides of Animal Cells," *Cell* 64:229-230 (1991).
Munk et al., "The θ-defensin, retrocyclin, inhibits HIV-1 entry," *AIDS Res. Hum. Retroviruses* 19(10):875-881 (2003).
Smith et al., "Cystic Fibrosis Airway Epithelia Fail to Kill Bacteria Because of Abnormal Airway Surface Fluid," *Cell* 85:229-236 (1996).
Tam et al., "Marked increase in membranolytic selectivity of novel cyclic tachyplesins constrained with an antiparallel two-βstrand cystine knot framework," *Biochem. Biophys. Res. Commun.* 267(3):783-790 (2000).

(Continued)

*Primary Examiner*—Cecilia J. Tsang
*Assistant Examiner*—Jennifer Ione Harle
(74) *Attorney, Agent, or Firm*—McDermott Will & Emery

(57) ABSTRACT

The invention provides theta defensin analogs having antimicrobial activity. The invention also provides a method of reducing or inhibiting growth or survival of a microorganism in an environment capable of sustaining the growth or survival of the microorganism, comprising administering an effective amount of a theta defensin analog to the environment, thereby reducing or inhibiting the growth or survival of the microorganism.

12 Claims, 21 Drawing Sheets

OTHER PUBLICATIONS

Tang et al., "A cyclic antimicrobial peptide produced in primate leukocytes by the litigation of two truncated α-defensins," *Science* 286(5439):498-502 (1999).

Tang and Selsted, "Characterization of the Disulfide Motif in BNBD-12, and Antimicrobialβ-Defensin Peptide from Bovine Neutrophils," *J. Biol. Chem.* 268:6649-6653 (1993).

Tran, Dat Q., "Isolation, synthesis, and biological properties of cyclic defensins: structure-activity relationships and comparison with protegrin PG-1" Dissertation, University of California, Irvine, Thesis Defense May 1, 2001.

Valore et al., "Human β-Defensin-1: An Antimicrobial Peptide of Urogenital Tissues," *J. Clin. Invest.* 101:1633-1642 (1998).

Wade et al., "All-D amino acid-containing channel-forming antibiotic peptides," *Proc. Natl. Acad. Sci. USA* 87:4761-4765 (1990).

Wu et al., "Protein *trans*-splicing by a split intein encoded in a split DnaE gene of *Synechocystis* sp. PCC6803," *Proc. Natl. Acad. Sci. USA* 95:9226-9231 (1998).

Zanetti et al., "Cathelicidins: a novel protein family with a common proregion and a variable C-terminal antimicrobial domain," *FEBS Lett.* 347:1-5 (1995).

RTD-1: G-F-C-R-C-L-C-R-R-G-V-C-R-C-I-C-T-R

RTD-2: G-F-C-R-C-I-C-T-R-G-F-C-R-C-I-C-T-R

RTD-3: G-V-C-R-C-L-C-R-R-G-V-C-R-C-L-C-R-R

FIGURE 1

RTD1a

| | |
|---|---|
| GACGGCTGCTGTTGCTACAGGAGACCCAGGACAGAGGACTGCTGTCTGCACTCTCTCTTC | 60 |
| ACTCTGCCTAACTTGAGGATCTGTCACTCCAGCCATGAGGACCTTCGCCCTCCTCACCGC | 120 |
|                                                                 M R T F A L L T A | |
| CATGCTTCTCCTGGTGGCCCTGCACGCTCAGGCAGAGGCACGTCAGGCAAGAGCTGATGA | 180 |
|   M L L L V A L H A Q A E A R Q A R A D E | |
| AGCTGCCGCCCAGCAGCAGCCTGGAACAGATGATCAGGGAATGGCTCATTCCTTTACATG | 240 |
|   A A A Q Q Q P G T D D Q G M A H S F T W | |
| GCCTGAAAACGCCGCTCTTCCACTTTCAGAGTCAGCGAAAGGCTTGAGGTGCATTTGCAC | 300 |
|   P E N A A L P L S E S A K G L $R^{13} C^{14} L^{15} C^{16} T^{17}$ | |
| ACGAGGATTCTGCCGTTTGTTATAATGTCACCTTGGGTCCTGCGCTTTTCGTGGTTGACT | 360 |
|   $R^{18} G^1 F^2 C^3$ P L L stop | |
| CCACCGGATCTGCTGCCGCTGAGCTTCCAGAATCAAGAAAAATATGCTCAGAAGTTACTT | 420 |
| TGAGAGTTAAAAGAAATTCTTGCTACTGCTGTACCTTCTCCTCAGTTTCCTTTTCTCATC | 480 |
| CCAAATAAATACCTTATCGC | 500 |

RTD1b

| | |
|---|---|
| GACCGCTGCTCTTGCTACAGGAGACCCGGGACAGAGGACTGCTGTCTGCCCTCTCTCTTC | 60 |
| ACTCTGCCTAACTTGAGGATCTGCCAGCCATGAGGACCTTCGCCCTCCTCACCGCCATGC | 120 |
|                                           M R T F A L L T A M L | |
| TTCTCCTGGTGGCCCTGCACGCTCAGGCAGAGGCACGTCAGGCAAGAGCTGATGAAGCTG | 180 |
|   L L V A L H A Q A E A R Q A R A D E A A | |
| CCGCCCAGCAGCAGCCTGGAGCAGATGATCAGGGAATGGCTCATTCCTTTACACGGCCTG | 240 |
|   A Q Q Q P G A D D Q G M A H S F T R P E | |
| AAAACGCCGCTCTTCCGCTTTCAGAGTCAGCGAGAGGCTTGAGGTGCCTTTGCAGACGAG | 300 |
|   N A A L P L S E S A R G L $R^4 C^5 L^6 C^7 R^8 R^9 C^{10}$ | |
| GAGTTTGCCAACTGTTATAAAGGCGTTTGGGTCCTGCGCTTTTCGTGGTTGACTCTGCC | 360 |
|   $V^{11} C^{12}$ Q L L stop | |
| GGATCTGCTGCCGCTGAGCTTCCAGAATCAAGAAAAATACGCTCAGAAGTTACTTTGAGA | 420 |
| GTTGAAAGAAATTCCTGTTACTCCTGTACCTTGTCCTCAATTTCCTTTTCTCATCCCAAA | 480 |
| TAAATACCTTCTCGC | 495 |

| # | Name | Sequence | Charge | Mass obs | Mass calc |
|---|---|---|---|---|---|
| 1 | aRTD-1-NH | GFCRCLCRRGVCRCICTR-NH | +6 | 2099.69 | (2099.78) |
| 2 | RTD-1* | GFCRCLCRRGVCRCICTR | +5 | 2082.67 | (2082.69) |
| 3 | aRTD-1-OH | GFCRCLCRRGVCRCICTR-OH | +5 | 2100.67 | (2099.86) |
| 4 | RTD-2* | GFCRCITRGFCRCICTR | +4 | 2075.63 | (2075.26) |
| 5 | aRTD-2-OH | GFCRCITRGFCRCICTR-OH | +4 | 2093.63 | (2094.03) |
| 6 | RTD-3* | GFCRCLCRRGVCRCLCRR | +6 | 2089.71 | (2089.66) |
| 7 | aRTD-3-OH | GVCRCLCRRGVCRCLCRR-OH | +6 | 2107.71 | (2107.18) |
| 8 | aRTD-3-NH | GVCRCLCRRGVCRCLCRR-NH | +7 | 2106.71 | (2106.11) |
| 9 | 3:1 aRTD-3-NH | RGVCRCLCRRGVCRCLAR-NH | +7 | 2106.71 | (2107.37) |
| 10 | 5:3 aRTD-3-NH | RGVARCLCRRGVCRCLAR-NH | +7 | 2042.53 | (2044.18) |
| 11 | PG-1* | RGGRLCYCRRRFCVCVGR | +7 | 2154.68 | (2155.83) |
| 12 | PG-1-OH | RGGRLCYCRRRFCVCVGR-OH | +6 | 2155.67 | (2157.96) |
| 13 | cPG-1 | GGRLCYCRRRFCVCVGRR | +6 | 2137.67 | (2140.04) |
| 14 | 4:4 PG-1-OH | GGRLCYCRRRFCVCVGRR-OH | +6 | 2155.67 | (2155.41) |
| 15 | 4:4 PG-1-NH | GGRLCYCRRRFCVCVGRR-NH | +7 | 2154.68 | (2154.14) |
| 16 | 3cys cPG-1 | GGRCYCRRRFCVCVGRR | +6 | 2173.74 | (2169.89) |
| 17 | 3cys 2:2 PG-1-OH | GGRCYCRRRFCVCVGRR-OH | +6 | 2191.74 | (2189.69) |
| 18 | 3cys 2:2 PG-1-NH | GGRCYCRRRFCVCVRR-NH | +7 | 2190.76 | (2188.12) |
| 19 | 3cys 3:1 PG-1-OH | RGGRCYCRRRFCVCVR-OH | +6 | 2191.74 | (2189.47) |
| 20 | 3cys 3:1 PG-1-NH | RGGRCYCRRRFCVCVR-NH | +7 | 2190.76 | (2188.47) |

FIGURE 5A

| Name | Sequence | Molecular mass (Ave M+H) | | |
|---|---|---|---|---|
| | | Linear | Folded | cyclic |
| 21. RTD-1-21: | G-F-C-R-A-L-C-R-R-G-V-C-R-A-I-C-T-R | 2042.5 | 2038.5 | 2020.5 |
| 22. RTD-1-22: | G-F-A-R-C-L-C-R-R-G-V-C-R-I-A-T-R | 2042.5 | 2038.5 | 2020.5 |
| 23. RTD-1-23: | G-F-A-R-C-L-A-R-R-G-V-A-R-I-A-T-R | 1978.4 | 1976.4 | 1958.4 |
| 24. RTD-1-24: | G-F-A-R-A-L-A-R-R-G-V-A-R-A-I-A-T-R | 1914.3 | N/A¹ | 1896.3 |
| 25. RTD-1-25: | G-F-C-R-C-R-R-G-V-C-L-C-I-C-T-R | 2106.6 | 2100.6 | 2082.6 |
| 26. RTD-3-26: | G-F-C-R-C-T-R-G-F-C-I-C-T-R | 2099.6 | 2093.6 | 2075.6 |
| 27. µRTD-1-27: | G-F-C-R-C-R-G-V-C-R-C-T-R | 1674.0 | 1670.0 | 1652.0 |
| 28. µRTD-1-28: | G-V-C-I-C-R-R-F-C-L-C-R-R | 1742.2 | 1738.2 | 1720.2 |
| 29. µRTD-1-29: | G-V-C-L-C-I-R-G-R-C-R-R | 1652.1 | 1648.1 | 1630.1 |
| 30. RTD-1-30: | G-V-C-T-C-I-C-R-R-F-C-G-C-L-C-R-R | 2106.6 | 2100.6 | 2082.6 |
| 31. RTD-4 (RTD1a/1c): | G-I-C-R-C-I-C-T-R-G-F-C-R-C-I-C-V-L | 2020.6 | 2014.6 | 1996.6 |
| 32. RTD-5 (RTD1b/1c): | G-I-C-R-C-L-C-R-R-G-V-C-R-C-I-C-V-L | 2027.6 | 2021.6 | 2003.6 |
| 33. RTD-6 (RTD1c/1c): | G-I-C-R-C-I-C-V-L-G-I-C-R-C-I-C-V-L | 1941.6 | 1935.6 | 1917.6 |

```
GAA TTC ATG GGA TTC TGC AGG TGC CTT TGC AGA CGA
EcoRI Met Gly Phe Cys Arg Cys Leu Cys Arg Arg
         ↑
GGA GTT TGC AGG TGC ATT TGC ACA CGA ATG GGA TTC
Gly Val Cys Arg Cys Ile Cys Thr Arg Met Gly Phe
                                  ⇑
TGC AGG TGC CTT TGC AGA CGA GGA GTT TGC AGG TGC
Cys Arg Cys Leu Cys Arg Arg Gly Val Cys Arg Cys

ATT TGC ACA CGA TAA TAA GTC GAC
Ile Cys Thr Arg Stp Stp  Sal I
```

B

SEQUENCE LISTING

<160> NUMBER OF SEQ ID NOS: 41

<210> SEQ ID NO 1
<211> LENGTH: 18
<212> TYPE: PRT
<213> ORGANISM: Macaca mulatta

<400> SEQUENCE: 1

Gly Phe Cys Arg Cys Leu Cys Arg Arg Gly Val Cys Arg Cys Ile Cys
1               5                   10                  15

Thr Arg

<210> SEQ ID NO 2
<211> LENGTH: 18
<212> TYPE: PRT
<213> ORGANISM: Macaca mulatta

<400> SEQUENCE: 2

Gly Phe Cys Arg Cys Ile Cys Thr Arg Gly Phe Cys Arg Cys Ile Cys
1               5                   10                  15

Thr Arg

<210> SEQ ID NO 3
<211> LENGTH: 18
<212> TYPE: PRT
<213> ORGANISM: Macaca mulatta

<400> SEQUENCE: 3

Gly Val Cys Arg Cys Leu Cys Arg Arg Gly Val Cys Arg Cys Leu Cys
1               5                   10                  15

Arg Arg

<210> SEQ ID NO 4
<211> LENGTH: 500
<212> TYPE: DNA
<213> ORGANISM: macaca mulatta
<220> FEATURE:
<221> NAME/KEY: CDS
<222> LOCATION: (95)...(325)

<400> SEQUENCE: 4
gacggctgct gttgctacag gagacccagg acagaggact gctgtctgca ctctctcttc     60
actctgccta acttgaggat ctgtcactcc agcc atg agg acc ttc gcc ctc ctc    115
                                    Met Arg Thr Phe Ala Leu Leu
                                    1               5 acc gcc atg ctt ctc ctg gtg gcc ctg cac gct cag gca gag gca cgt      163
Thr Ala Met Leu Leu Leu Val Ala Leu His Ala Gln Ala Glu Ala Arg
        10                  15                  20 cag gca aga gct gat gaa gct gcc gcc cag cag cag cct gga aca gat      211
Gln Ala Arg Ala Asp Glu Ala Ala Ala Gln Gln Gln Pro Gly Thr Asp
    25                  30                  35 gat cag gga atg gct cat tcc ttt aca tgg cct gaa aac gcc gct ctt      259
Asp Gln Gly Met Ala His Ser Phe Thr Trp Pro Glu Asn Ala Ala Leu
40                  45                  50                  55 cca ctt tca gag tca gcg aaa ggc ttg agg tgc att tgc aca cga gga      307
Pro Leu Ser Glu Ser Ala Lys Gly Leu Arg Cys Ile Cys Thr Arg Gly
                60                  65                  70 ttc tgc cgt ttg tta taa tgtcaccttg ggtcctgcgc ttttcgtggt             355
Phe Cys Arg Leu Leu *
            75

```
tgactccacc ggatctgctg ccgctgagct tccagaatca agaaaaatat gctcagaagt      415
tactttgaga gttaaaagaa attcttgcta ctgctgtacc ttctcctcag tttccttttc      475
tcatcccaaa taaataccct atcgc                                            500
```

<210> SEQ ID NO 5
<211> LENGTH: 76
<212> TYPE: PRT
<213> ORGANISM: macaca mulatta

<400> SEQUENCE: 5

```
Met Arg Thr Phe Ala Leu Leu Thr Ala Met Leu Leu Leu Val Ala Leu
 1               5                  10                  15

His Ala Gln Ala Glu Ala Arg Gln Ala Arg Ala Asp Glu Ala Ala Ala
            20                  25                  30

Gln Gln Gln Pro Gly Thr Asp Asp Gln Gly Met Ala His Ser Phe Thr
        35                  40                  45

Trp Pro Glu Asn Ala Ala Leu Pro Leu Ser Glu Ser Ala Lys Gly Leu
    50                  55                  60

Arg Cys Ile Cys Thr Arg Gly Phe Cys Arg Leu Leu
65                  70                  75
```

<210> SEQ ID NO 6
<211> LENGTH: 495
<212> TYPE: DNA
<213> ORGANISM: Macaca mulatta
<220> FEATURE:
<221> NAME/KEY: CDS
<222> LOCATION: (90)...(320)

<400> SEQUENCE: 6

```
gaccgctgct cttgctacag gagacccggg acagaggact gctgtctgcc ctctctcttc       60
actctgccta acttgaggat ctgccagcc atg agg acc ttc gcc ctc ctc acc       113
                                 Met Arg Thr Phe Ala Leu Leu Thr
                                  1               5 gcc atg ctt ctc ctg gtg gcc ctg cac gct cag gca gag gca cgt cag      161
Ala Met Leu Leu Leu Val Ala Leu His Ala Gln Ala Glu Ala Arg Gln
     10                  15                  20 gca aga gct gat gaa gct gcc gcc cag cag cag cct gga gca gat gat      209
Ala Arg Ala Asp Glu Ala Ala Ala Gln Gln Gln Pro Gly Ala Asp Asp
 25                  30                  35                  40 cag gga atg gct cat tcc ttt aca cgg cct gaa aac gcc gct ctt ccg      257
Gln Gly Met Ala His Ser Phe Thr Arg Pro Glu Asn Ala Ala Leu Pro
                 45                  50                  55 ctt tca gag tca gcg aga ggc ttg agg tgc ctt tgc aga cga gga gtt      305
Leu Ser Glu Ser Ala Arg Gly Leu Arg Cys Leu Cys Arg Arg Gly Val
             60                  65                  70 tgc caa ctg tta taa aggcgtttgg ggtcctgcgc ttttcgtggt tgactctgcc       360
Cys Gln Leu Leu *
                 75 ggatctgctg ccgctgagct tccagaatca agaaaaatac gctcagaagt tactttgaga      420 gttgaaagaa attcctgtta ctcctgtacc ttgtcctcaa tttccttttc tcatcccaaa      480 taaataccct ctcgc                                                      495
```

<210> SEQ ID NO 7
<211> LENGTH: 76
<212> TYPE: PRT
<213> ORGANISM: Macaca mulatta

```
<400> SEQUENCE: 7

Met Arg Thr Phe Ala Leu Leu Thr Ala Met Leu Leu Val Ala Leu
 1               5                  10                  15

His Ala Gln Ala Glu Ala Arg Gln Ala Arg Ala Asp Glu Ala Ala Ala
            20                  25                  30

Gln Gln Gln Pro Gly Ala Asp Asp Gln Gly Met Ala His Ser Phe Thr
            35                  40                  45

Arg Pro Glu Asn Ala Ala Leu Pro Leu Ser Glu Ser Ala Arg Gly Leu
    50                  55                  60

Arg Cys Leu Cys Arg Arg Gly Val Cys Gln Leu Leu
65                  70                  75

<210> SEQ ID NO 8
<211> LENGTH: 27
<212> TYPE: DNA
<213> ORGANISM: Macaca mulatta
<220> FEATURE:
<221> NAME/KEY: CDS
<222> LOCATION: (1)...(27)

<400> SEQUENCE: 8 agg tgc att tgc aca cga gga ttc tgc                          27
Arg Cys Ile Cys Thr Arg Gly Phe Cys
 1               5

<210> SEQ ID NO 9
<211> LENGTH: 9
<212> TYPE: PRT
<213> ORGANISM: Macaca mulatta

<400> SEQUENCE: 9

Arg Cys Ile Cys Thr Arg Gly Phe Cys
 1               5

<210> SEQ ID NO 10
<211> LENGTH: 39
<212> TYPE: DNA
<213> ORGANISM: Macaca mulatta
<220> FEATURE:
<221> NAME/KEY: CDS
<222> LOCATION: (1)...(39)

<400> SEQUENCE: 10 agg tgc ctt tgc aga cga gga gtt tgc caa ctg tta taa          39
Arg Cys Leu Cys Arg Arg Gly Val Cys Gln Leu Leu  *
 1               5                  10

<210> SEQ ID NO 11
<211> LENGTH: 12
<212> TYPE: PRT
<213> ORGANISM: Macaca mulatta

<400> SEQUENCE: 11

Arg Cys Leu Cys Arg Arg Gly Val Cys Gln Leu Leu
 1               5                  10

<210> SEQ ID NO 12
<211> LENGTH: 18
<212> TYPE: PRT
<213> ORGANISM: Artificial Sequence
<220> FEATURE:
<223> OTHER INFORMATION: synthetic construct

<400> SEQUENCE: 12
```

Gly Phe Cys Arg Cys Leu Cys Arg Arg Gly Val Cys Arg Cys Ile Cys
1               5                   10                  15

Thr Arg

<210> SEQ ID NO 13
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: AMIDATION
<222> LOCATION: 18
<223> OTHER INFORMATION: at the C terminus

<400> SEQUENCE: 13

Gly Phe Cys Arg Cys Leu Cys Arg Arg Gly Val Cys Arg Cys Ile Cys
1               5                   10                  15

Thr Arg

<210> SEQ ID NO 14
<211> LENGTH: 18
<212> TYPE: PRT
<213> ORGANISM: Artificial Sequence
<220> FEATURE:
<223> OTHER INFORMATION: synthetic construct

<400> SEQUENCE: 14

Gly Phe Cys Arg Cys Ile Cys Thr Arg Gly Phe Cys Arg Cys Ile Cys
1               5                   10                  15

Thr Arg

<210> SEQ ID NO 15
<211> LENGTH: 18
<212> TYPE: PRT
<213> ORGANISM: Artificial Sequence
<220> FEATURE:
<223> OTHER INFORMATION: synthetic construct

<400> SEQUENCE: 15

Gly Val Cys Arg Cys Leu Cys Arg Arg Gly Val Cys Arg Cys Leu Cys
1               5                   10                  15

Arg Arg

<210> SEQ ID NO 16
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: AMIDATION
<222> LOCATION: 18
<223> OTHER INFORMATION: at the C terminus

<400> SEQUENCE: 16

Gly Val Cys Arg Cys Leu Cys Arg Arg Gly Val Cys Arg Cys Leu Cys
1               5                   10                  15

Arg Arg

<210> SEQ ID NO 17
<211> LENGTH: 18
<212> TYPE: PRT
<213> ORGANISM: Artificial Sequence
<220> FEATURE:

```
<223> OTHER INFORMATION: synthetic construct
<220> FEATURE:
<221> NAME/KEY: AMIDATION
<222> LOCATION: 18
<223> OTHER INFORMATION: at the C terminus

<400> SEQUENCE: 17

Arg Gly Val Cys Arg Cys Leu Cys Arg Arg Gly Val Cys Arg Cys Leu
 1               5                  10                  15

Cys Arg

<210> SEQ ID NO 18
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: AMIDATION
<222> LOCATION: 18
<223> OTHER INFORMATION: at the C terminus

<400> SEQUENCE: 18

Arg Gly Val Ala Arg Cys Leu Cys Arg Arg Gly Val Cys Arg Cys Leu
 1               5                  10                  15

Ala Arg

<210> SEQ ID NO 19
<211> LENGTH: 18
<212> TYPE: PRT
<213> ORGANISM: Artificial Sequence
<220> FEATURE:
<223> OTHER INFORMATION: synthetic construct

<400> SEQUENCE: 19

Gly Phe Cys Arg Ala Leu Cys Arg Arg Gly Val Cys Arg Ala Ile Cys
 1               5                  10                  15

Thr Arg

<210> SEQ ID NO 20
<211> LENGTH: 18
<212> TYPE: PRT
<213> ORGANISM: Artificial Sequence
<220> FEATURE:
<223> OTHER INFORMATION: synthetic construct

<400> SEQUENCE: 20

Gly Phe Ala Arg Cys Leu Cys Arg Arg Gly Val Cys Arg Cys Ile Ala
 1               5                  10                  15

Thr Arg

<210> SEQ ID NO 21
<211> LENGTH: 18
<212> TYPE: PRT
<213> ORGANISM: Artificial Sequence
<220> FEATURE:
<223> OTHER INFORMATION: synthetic construct

<400> SEQUENCE: 21

Gly Phe Ala Arg Cys Leu Ala Arg Arg Gly Val Ala Arg Cys Ile Ala
 1               5                  10                  15

Thr Arg

<210> SEQ ID NO 22
```

```
<211> LENGTH: 18
<212> TYPE: PRT
<213> ORGANISM: Artificial Sequence
<220> FEATURE:
<223> OTHER INFORMATION: synthetic construct

<400> SEQUENCE: 22

Gly Phe Ala Arg Ala Leu Ala Arg Arg Gly Val Ala Arg Ala Ile Ala
 1               5                  10                  15

Thr Arg

<210> SEQ ID NO 23
<211> LENGTH: 18
<212> TYPE: PRT
<213> ORGANISM: Artificial Sequence
<220> FEATURE:
<223> OTHER INFORMATION: synthetic construct

<400> SEQUENCE: 23

Gly Phe Cys Arg Cys Arg Cys Arg Arg Gly Val Cys Leu Cys Ile Cys
 1               5                  10                  15

Thr Arg

<210> SEQ ID NO 24
<211> LENGTH: 18
<212> TYPE: PRT
<213> ORGANISM: Artificial Sequence
<220> FEATURE:
<223> OTHER INFORMATION: synthetic construct

<400> SEQUENCE: 24

Gly Phe Cys Arg Cys Arg Cys Thr Arg Gly Phe Cys Ile Cys Ile Cys
 1               5                  10                  15

Thr Arg

<210> SEQ ID NO 25
<211> LENGTH: 14
<212> TYPE: PRT
<213> ORGANISM: Artificial Sequence
<220> FEATURE:
<223> OTHER INFORMATION: synthetic construct

<400> SEQUENCE: 25

Gly Phe Cys Arg Cys Arg Arg Gly Val Cys Arg Cys Thr Arg
 1               5                  10

<210> SEQ ID NO 26
<211> LENGTH: 14
<212> TYPE: PRT
<213> ORGANISM: Artificial Sequence
<220> FEATURE:
<223> OTHER INFORMATION: synthetic construct

<400> SEQUENCE: 26

Gly Val Cys Ile Cys Arg Arg Arg Phe Cys Leu Cys Arg Arg
 1               5                  10

<210> SEQ ID NO 27
<211> LENGTH: 14
<212> TYPE: PRT
<213> ORGANISM: Artificial Sequence
<220> FEATURE:
<223> OTHER INFORMATION: synthetic construct

<400> SEQUENCE: 27
```

```
Gly Val Cys Leu Cys Ile Arg Gly Arg Cys Arg Cys Arg Arg
1               5                   10
```

<210> SEQ ID NO 28
<211> LENGTH: 18
<212> TYPE: PRT
<213> ORGANISM: Artificial Sequence
<220> FEATURE:
<223> OTHER INFORMATION: synthetic construct

<400> SEQUENCE: 28

```
Gly Val Cys Thr Cys Ile Cys Arg Arg Phe Cys Gly Cys Leu Cys
1               5                   10                  15

Arg Arg
```

<210> SEQ ID NO 29
<211> LENGTH: 18
<212> TYPE: PRT
<213> ORGANISM: Artificial Sequence
<220> FEATURE:
<223> OTHER INFORMATION: synthetic construct

<400> SEQUENCE: 29

```
Gly Ile Cys Arg Cys Ile Cys Thr Arg Gly Phe Cys Arg Cys Ile Cys
1               5                   10                  15

Val Leu
```

<210> SEQ ID NO 30
<211> LENGTH: 18
<212> TYPE: PRT
<213> ORGANISM: Artificial Sequence
<220> FEATURE:
<223> OTHER INFORMATION: synthetic construct

<400> SEQUENCE: 30

```
Gly Ile Cys Arg Cys Leu Cys Arg Arg Gly Val Cys Arg Cys Ile Cys
1               5                   10                  15

Val Leu
```

<210> SEQ ID NO 31
<211> LENGTH: 18
<212> TYPE: PRT
<213> ORGANISM: Artificial Sequence
<220> FEATURE:
<223> OTHER INFORMATION: synthetic construct

<400> SEQUENCE: 31

```
Gly Ile Cys Arg Cys Ile Cys Val Leu Gly Ile Cys Arg Cys Ile Cys
1               5                   10                  15

Val Leu
```

<210> SEQ ID NO 32
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: AMIDATION
<222> LOCATION: 18
<223> OTHER INFORMATION: at the C terminus

<400> SEQUENCE: 32

```
Arg Gly Gly Arg Leu Cys Tyr Cys Arg Arg Phe Cys Val Cys Val
1               5                   10                  15
```

```
<210> SEQ ID NO 33
<211> LENGTH: 18
<212> TYPE: PRT
<213> ORGANISM: Artificial Sequence
<220> FEATURE:
<223> OTHER INFORMATION: synthetic construct

<400> SEQUENCE: 33

Arg Gly Gly Arg Leu Cys Tyr Cys Arg Arg Arg Phe Cys Val Cys Val
 1               5                  10                  15

Gly Arg

<210> SEQ ID NO 34
<211> LENGTH: 18
<212> TYPE: PRT
<213> ORGANISM: Artificial Sequence
<220> FEATURE:
<223> OTHER INFORMATION: synthetic construct

<400> SEQUENCE: 34

Gly Gly Arg Leu Cys Tyr Cys Arg Arg Arg Phe Cys Val Cys Val Gly
 1               5                  10                  15

Arg Arg

<210> SEQ ID NO 35
<211> LENGTH: 18
<212> TYPE: PRT
<213> ORGANISM: Artificial Sequence
<220> FEATURE:
<223> OTHER INFORMATION: synthetic construct

<400> SEQUENCE: 35

Gly Gly Arg Leu Cys Tyr Cys Arg Arg Arg Phe Cys Val Cys Val Gly
 1               5                  10                  15

Arg Arg

<210> SEQ ID NO 36
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: AMIDATION
<222> LOCATION: 18
<223> OTHER INFORMATION: at the C terminus

<400> SEQUENCE: 36

Gly Gly Arg Leu Cys Tyr Cys Arg Arg Arg Phe Cys Val Cys Val Gly
 1               5                  10                  15

Arg Arg

<210> SEQ ID NO 37
<211> LENGTH: 18
<212> TYPE: PRT
<213> ORGANISM: Artificial Sequence
<220> FEATURE:
<223> OTHER INFORMATION: synthetic construct

<400> SEQUENCE: 37

Gly Gly Cys Arg Cys Tyr Cys Arg Arg Arg Phe Cys Val Cys Val Cys
 1               5                  10                  15
```

Arg Arg

<210> SEQ ID NO 38
<211> LENGTH: 18
<212> TYPE: PRT
<213> ORGANISM: Artificial Sequence
<220> FEATURE:
<223> OTHER INFORMATION: synthetic construct

<400> SEQUENCE: 38

Gly Gly Cys Arg Cys Tyr Cys Arg Arg Arg Phe Cys Val Cys Val Cys
 1               5                  10                  15

Arg Arg

<210> SEQ ID NO 39
<211> LENGTH: 18
<212> TYPE: PRT
<213> ORGANISM: Artificial Sequence
<220> FEATURE:
<223> OTHER INFORMATION: synthetic construct
<220> FEATURE:
<221> NAME/KEY: AMIDATION
<222> LOCATION: 18
<223> OTHER INFORMATION: at the C terminus

<400> SEQUENCE: 39

Gly Gly Cys Arg Cys Tyr Cys Arg Arg Arg Phe Cys Val Cys Val Cys
 1               5                  10                  15

Arg Arg

<210> SEQ ID NO 40
<211> LENGTH: 18
<212> TYPE: PRT
<213> ORGANISM: Artificial Sequence
<220> FEATURE:
<223> OTHER INFORMATION: synthetic construct

<400> SEQUENCE: 40

Arg Gly Gly Cys Arg Cys Tyr Cys Arg Arg Arg Phe Cys Val Cys Val
 1               5                  10                  15

Cys Arg

<210> SEQ ID NO 41
<211> LENGTH: 17
<212> TYPE: PRT
<213> ORGANISM: Artificial Sequence
<220> FEATURE:
<223> OTHER INFORMATION: synthetic construct
<220> FEATURE:
<221> NAME/KEY: AMIDATION
<222> LOCATION: 18
<223> OTHER INFORMATION: at the C terminus

<400> SEQUENCE: 41

Arg Gly Gly Cys Arg Cys Tyr Cys Arg Arg Arg Phe Cys Val Cys Val
 1               5                  10                  15

Arg

US 7,119,070 B2

ANTIMICROBIAL THETA DEFENSINS, ANALOGS THEREOF, AND METHODS OF USE

This application claims benefit of the filing date of U.S. Provisional Application No. 60/377,071, filed Apr. 30, 2002, and which is incorporated herein by reference.

This invention was made with government support under grant number AI22931 awarded by the National Institutes of Health. The government has certain rights in the invention.

BACKGROUND OF THE INVENTION

The present invention relates generally to antimicrobial agents and, more specifically, to cyclic theta defensin peptides and methods of using a theta defensin peptide to reduce or inhibit microbial growth or survival.

Infections by microorganisms, including bacteria, viruses and fungi, are a major cause of human morbidity and mortality. Although anyone can be a victim of such infection, the sick and elderly are particularly susceptible. For example, hospitalized patients frequently acquire secondary infections due to a combination of their weakened condition and the prevalence of microorganisms in a hospital setting. Such opportunistic infections result in increased suffering of the patient, increased length of hospitalization and, consequently, increased costs to the patient and the health care system. Similarly, the elderly, particularly those living in nursing homes or retirement communities, are susceptible to infections because of their close living arrangement and the impaired responsiveness of their immune systems.

Numerous drugs are available for treating infections by certain microorganisms. In particular, various bacterial infections have been amenable to treatment by antibiotics. However, the prolonged use of antibiotics since their discovery has resulted in the selection of bacteria that are relatively resistant to these drugs. Furthermore, few if any drugs are effective against microorganisms such as viruses. As a result, continuing efforts are being made to identify new and effective agents for treating infections by a variety of microorganisms.

The identification of naturally occurring compounds that act as antimicrobial agents has provided novel and effective drugs. Many organisms protect themselves by producing natural products that are toxic to other organisms. Frogs, for example, produce a class of peptides, magainins, which provide a defense mechanism for the frog against potential predators. Magainins have been purified and shown to have antimicrobial activity, thus providing a natural product useful for reducing or inhibiting microbial infections.

Natural products useful as antimicrobial agents also have been purified from mammalian organisms, including humans. For example, the defensins are a class of peptides that have been purified from mammalian neutrophils and demonstrated to have antimicrobial activity. Similarly, indolicidin is a peptide that has been isolated from bovine neutrophils and has antimicrobial activity, including activity against viruses, bacteria, fungi and protozoan parasites. Thus, naturally occurring compounds provide a source of drugs that are potentially useful for treating microbial infections.

Upon identifying naturally occurring peptides useful as antimicrobial agents, efforts began to chemically modify the peptides to obtain analogs having improved properties. Such efforts have resulted, for example, in the identification of indolicidin analogs which, when administered to an individual, have increased selectivity against the infecting microorganisms as compared to the individual's own cells. Thus, the availability of naturally occurring antimicrobial agents has provided new drugs for treating microbial infections and has provided a starting material to identify analogs of the naturally occurring molecule that have desirable characteristics.

Although such natural products and their analogs have provided new agents for treating microbial infections, it is well known that microorganisms can become resistant to drugs. Thus, a need exists to identify agents that effectively reduce or inhibit the growth or survival of microorganisms. The present invention satisfies this need and provides additional advantages.

SUMMARY OF THE INVENTION

The invention provides theta defensin analogs having antimicrobial activity. The invention also provides a method of reducing or inhibiting growth or survival of a microorganism in an environment capable of sustaining the growth or survival of the microorganism, comprising administering an effective amount of a theta defensin analog to the environment, thereby reducing or inhibiting the growth or survival of the microorganism.

BRIEF DESCRIPTION OF THE DRAWINGS

FIG. 1 shows the sequence and disulfide bonding pattern of RTD-1 (SEQ ID NO:1), RTD-2 (SEQ ID NO:2) and RTD-3 (SEQ ID NO:3).

FIG. 2 shows RTD1a and RTD1b cDNAs. FIG. 2A shows full length cDNA sequence of RTD1a (SEQ ID NO:4) with the deduced amino acid sequence (SEQ ID NO:5). FIG. 2B shows full length cDNA sequence of RTD1b (SEQ ID NO:6) with the deduced amino acid sequence (SEQ ID NO:7). Underlined amino acids are found in RTD-1, and superscript numbers correspond to the residue numbering of RTD-1 shown in FIG. 1. The underlined sequences in FIG. 2A correspond to nucleotides 287 to 313 (SEQ ID NO:8) and amino acids 65 to 73 (SEQ ID NO:9) of RTD1a. The underlined sequences in FIG. 2B correspond to nucleotides 282 to 308 (SEQ ID NO:10) and amino acids 65 to 73 (SEQ ID NO:11) of RTD1b. ATG of the initiation methionines are in bold, as are the polyadenlation sites at the 3' ends of the sequences.

FIG. 5A shows the amino acid sequences of θ-defensins, PG-1, and analogs. Native sequences are indicated by asterisks (*). The peptide charges are calculated at pH 7.0. Molecular masses calculated from peptide sequences and structures are compared with those determined experimentally by MALDI-TOF mass spectroscopy (in parentheses). Cysteine (shaded residues) connectivity is shown in accordance to structures determined for PG-1 and RTD-1 (Kokryakov et al., *Febs Letters* 327:231–236 (1993); Tang et al., *Science* 286:498–502 (1999)). "a"-acyclic analogs of θ-defensins; "c"-cyclic analogs of PG-1. "—NH" or "—OH" denotes amide and acid of the peptide terminus, respectively. "3cys"-tridisulfide PG-1 analogs. "Even" and "overlapping" chain termini are indicated by a pair of numbers separated by a colon corresponding to respective lengths of N- and C-termini. Native PG-1 and PG-1-OH have the 5:3, "overlapping"-termini structure. FIG. 5B shows the sequences and disulfide bonds of additional theta defensin analogs. The masses of various forms of the peptides are also shown.

FIG. 11A shows kinetics of ONPG hydrolysis for increasing concentrations of RTD-1. Inhibitors or 0.01% acetic acid were added at the time noted by the arrows. FIG. 11B shows inhibition of ONPG hydrolysis by IPTG (10 mM final) and RTD-2 (1 μg/ml final). Addition of RTD-2 inhibited ONPG hydrolysis (dashed line) compared to the rate of hydrolysis for 1 μg/ml of RTD-1 (solid line).

DETAILED DESCRIPTION OF THE INVENTION

Figure 3:
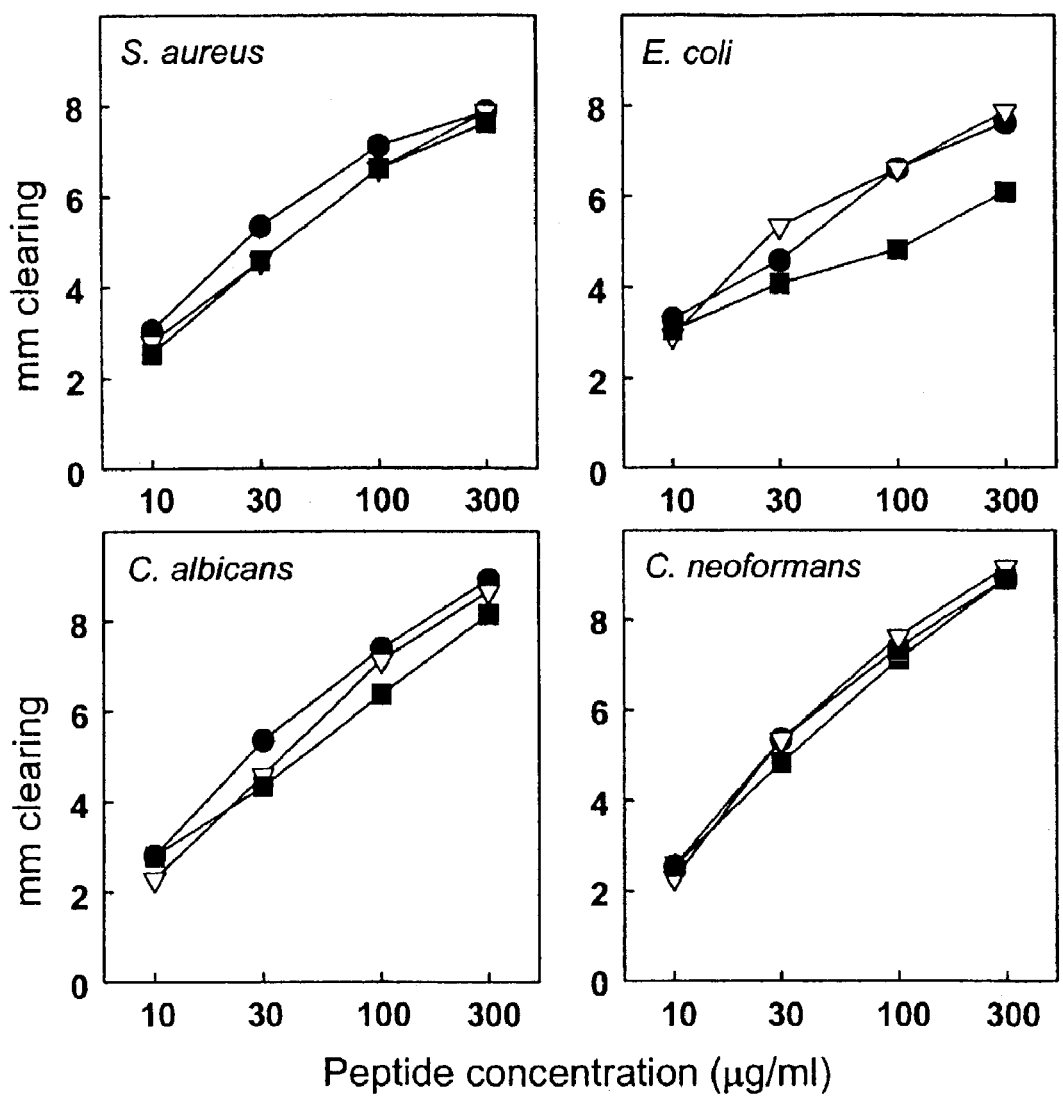
FIG. 3 shows antimicrobial activities of RTD-1, 2, and 3. The antimicrobial activities of synthetic RTD-1 (●), RTD-2 (∇), and RTD-3 (■) against *S. aureus* 502a, *E. coli* ML35, *C. albicans* 16820, and *C. neoformans* 271a were assessed in an agar diffusion assay.

The invention provides theta defensins and theta defensin analogs having antimicrobial activity. The theta defensins and theta defensin analogs can be used to reduce or inhibit the growth or survival of a microorganism. In addition to antimicrobial activity, the theta defensins and theta defensin analogs exhibit low hemolytic activity.

The Rhesus theta defensin (θ-defensin) RTD-1 is a macrocyclic 18-amino acid antimicrobial peptide formed by the ligation of two nine-residue sequences derived from similar 76-amino acid precursors, termed RTD1a and RTD1b (see FIG. 2) (U.S. Pat. No. 6,335,318, issued Jan. 1, 2002; WO 00/68265; Tang et al., Science 286:498–502 (1999), each of which is incorporated herein by reference). The two nine-residue sequences can be ligated as a heterodimer (RTD-1) or homodimer (RTD-2 and 3)(see FIG. 1).

The theta defensin peptides of the invention have antimicrobial activity and include theta defensin and theta defensin analogs having the amino acid sequence Xaa1-Xaa2-Xaa3-Xaa4-Xaa5-Xaa1-Xaa6-Xaa4-Xaa4-Xaa1-Xaa1-Xaa6-Xaa4-Xaa5-Xaa1-Xaa3-Xaa7-Xaa8; having the amino acid sequence Xaa1-Xaa2-Xaa3-Xaa4-Xaa5-Xaa1-Xaa6-Xaa7-Xaa8-Xaa1-Xaa2-Xaa6-Xaa4-Xaa5-Xaa1-Xaa3-Xaa7-Xaa8; and having the amino acid sequence Xaa1-Xaa1-Xaa3-Xaa4-Xaa5-Xaa1-Xaa6-Xaa4-Xaa4-Xaa1-Xaa1-Xaa6-Xaa4-Xaa5-Xaa1-Xaa3-Xaa4-Xaa4, wherein Xaa1 independently is an aliphatic amino acid; Xaa2 is an aromatic amino acid; Xaa3 is Cys or Trp; Xaa4 independently is Arg or Lys; Xaa5 is Cys or Trp; Xaa6 is Cys or Trp; Xaa7 is Thr or Ser; and Xaa8 is Arg or Lys. For example, Xaa1 can be an aliphatic amino acid such as Gly, Ile, Leu, Val or Ala and Xaa2 can be an aromatic amino acid such as Phe, Trp or Tyr. In general, a theta defensin is a cyclic peptide, wherein Xaa1 is linked through a peptide bond to Xaa8, and contains three intrachain crosslinks, which are formed between Xaa3 and Xaa3, between Xaa5 and Xaa5, and between Xaa7 and Xaa7. However, as disclosed herein, the invention also encompasses linear theta defensin precursors as well as peptide portions of a theta defensin or theta defensin analog.

As used herein, the term "independently," when used in reference to the selection of an amino acid at a position in the generic structure of a theta defensin, means that the selection of one amino acid at a position, for example, Xaa1 at position 1 of the theta defensin sequence Xaa1-Xaa2-Xaa3-Xaa4-Xaa5-Xaa1-Xaa6-Xaa4-Xaa4-Xaa1-Xaa1-Xaa6-Xaa4-Xaa5-Xaa1-Xaa3-Xaa7-Xaa8; or of the theta defensin sequence Xaa1-Xaa2-Xaa3-Xaa4-Xaa5-Xaa1-Xaa6-Xaa7-Xaa8-Xaa1-Xaa2-Xaa6-Xaa4-Xaa5-Xaa1-Xaa3-Xaa7-Xaa8; or of the theta defensin sequence Xaa1-Xaa1-Xaa3-Xaa4-Xaa5-Xaa1-Xaa6-Xaa4-Xaa4-Xaa1-Xaa1-Xaa6-Xaa4-Xaa5-Xaa1-Xaa3-Xaa4-Xaa4, has no influence on the selection, for example, of Xaa1 at position 6 or 10 or the like. For example, Xaa1 can be Gly at position 1 and can be Leu or Ile at position 6.

The theta defensins and theta defensin analogs of the invention exhibit broad spectrum antimicrobial activity. An exemplified theta defensin is an 18 amino acid cyclic peptide having the amino acid sequence Gly-Phe-Cys-Arg-Cys-Leu-Cys-Arg-Arg-Gly-Val-Cys-Arg-Cys-Ile-Cys-Thr-Arg (SEQ ID NO:1), wherein the Gly at position 1 (Gly-1) is linked through a peptide bond to Arg-18, and wherein three intrachain crosslinks are present due to disulfide bonds between Cys-3 and Cys-16, between Cys-5 and Cys-14, and between Cys-7 and Cys-12. Other exemplary theta defensins include RTD-2 (SEQ ID NO:2) and RTD-3 (SEQ ID NO:3) (see FIG. 1).

A theta defensin which lacks free amino and carboxyl termini is resistant to exopeptidases and is thus relatively stable to proteolytic degradation. The invention also provides theta defensin analogs having antimicrobial activity (see Examples I–III). Exemplary theta defensin analogs include the analogs shown in Table 1 and referenced as SEQ ID NOS:12–31.

TABLE 1

| NAME | SEQUENCE | SEQ ID NO. |
|---|---|---|
| aRTD-1-NH | G F C R C L C R R G V C R C I C T R-NH | 13 |
| RTD-1* | G F C R C L C R R G V C R C I C T R | 1 |
| aRTD-1-OH | G F C R C L C R R G V C R C I C T R-OH | 12 |
| RTD-2* | G F C R C I C T R G F C R C I C T R | 2 |
| aRTD-2-OH | G F C R C I C T R G F C R C I C T R-OH | 14 |
| RTD 3* | G V C R C L C R R G V C R C L C R R | 3 |
| aRTD-3-OH | G V C R C L C R R G V C R C L C R R-OH | 15 |
| aRTD-3-NH | G V C R C L C R R G V C R C L C R R-NH | 16 |
| 3:1 aRTD-3-NH | R G V C R C L C R R G V C R C L C R-NH | 17 |
| 5:3 aRTD-3-NH | R G V A R C L C R R G V C R C L A R-NH | 18 |
| RTD-1-21: | G - F - C - R - A - L - C - R - R - G - V - C - R - A - I - C - T - R | 19 |
| RTD-1-22: | G - F - A - R - C - L - C - R - R - G - V - C - R - C - I - A - T - R | 20 |
| RTD-1-23: | G - F - A - R - C - L - A - R - R - G - V - A - R - C - I - A - T - R | 21 |
| RTD-1-24: | G - F - A - R - A - L - A - R - R - G - V - A - R - A - I - A - T - R | 22 |
| RTD-1-25: | G - F - C - R - C - R - C - R - R - G - V - C - L - C - I - C - T - R | 23 |
| RTD-1-26: | G - F - C - R - C - R - C - T - R - G - F - C - I - C - I - C - T - R | 24 |
| µRTD-1-27: | G - F - C - R - C - R - R - G - V - C - R - C - T - R | 25 |
| µRTD-1-28: | G - V - C - I - C - R - R - R - F - C - L - C - R - R | 26 |
| µRTD-1-29: | G - V - C - L - C - I - R - G - R - C - R - C - R - R | 27 |
| RTD-1-30: | G - V - C - T - C - I - C - R - R - R - F - C - G - C - L - C - R - R | 28 |
| RTD-4 (RTD1a/1c): | G - I - C - R - C - I - C - T - R - G - F - C - R - C - I - C - V - L | 29 |
| RTD-5 (RTD1b/1c): | G - I - C - R - C - L - C - R - R - G - V - C - R - C - I - C - V - L | 30 |
| RTD-6 (RTD1c/1c): | G - I - C - R - C - I - C - V - L - G - I - C - R - C - I - C - V - L | 31 |

As used herein, the term "isolated," when used in reference to a natural theta defensin, means that the peptide is free of at least a portion of the contents associated with or occurring with the theta defensin peptide in the native environment. An isolated theta defensin can be relatively free of proteins, lipids, nucleic acids or other molecules it normally is associated with in a cell. In general, an isolated theta defensin peptide can constitute at least about 25% by weight of a sample containing the theta defensin, and usually constitutes at least about 50%, at least about 75%, at least about 85%, at least about 90% of a sample, particularly about 95% of the sample or 99% or more. An isolated theta defensin can be obtained by isolation from a cell expressing the theta defensin, can be chemically synthesized, or can be expressed from a recombinant nucleic acid molecule (see U.S. Pat. No. 6,335,318 and WO 00/68265). Following chemical synthesis or recombinant expression, the theta defensin precursor peptide generally is linear and, therefore, can be further subjected to appropriate conditions for cyclizing the peptide and forming the intrachain crosslinks, as disclosed herein.

The theta defensin peptides shown as SEQ ID NOS:1–3 constitutes the first members of a new class of defensins and are the basis for constructing theta defensin analogs as disclosed herein (see Examples I–III). Previously described defensins are cationic, arginine-rich peptides having 29 to 42 amino acids and containing three disulfide bonds (see Lehrer et al., *Cell* 64:229–230 (1991); Lehrer and Ganz, *Current Opin. Immunol.* 11:23–27 (1999)). The β-defensins, for example, contain 38 to 42 amino acids and have a net charge of +4 to −10 (see U.S. Pat. No. 5,459,235, issued Oct. 17, 1995, which is incorporated herein by reference). The disulfide bonds in β-defensins are formed in a characteristic pattern between the first and fifth Cys residues, the second and fourth Cys residues, and the third and sixth Cys residues. In addition, some β-defensins contain a pyroglutamate residue at the amino terminus (U.S. Pat. No. 5,459,235, supra, 1995).

Defensins and defensin-like peptides are endogenously expressed in various organisms. In mammals, defensins generally are expressed in neutrophils, macrophages and intestinal cells (see Lehrer et al., supra, 1991; Lehrer and Ganz, supra, 1999). Defensins can exhibit potent antimicrobial activity against a broad spectrum of microorganisms, including gram negative and gram positive bacteria, fungi, protozoans such as *Acanthamoeba* and *Giardia*, enveloped viruses such as herpes simplex viruses and human immunodeficiency viruses, and helminths. Defensins also have other properties, including chemotactic activity for human monocytes and the ability to interfere with adrenocorticotropin binding to its receptor (see Lehrer et al., supra, 1991).

A new class of defensins, termed theta defensins, have been described (U.S. Pat. No. 6,335,318, issued Jan. 1, 2002; WO 00/68265; Tang et al., *Science* 286:498–502 (1999)). Theta defensins have been classified as members of the defensin family of peptides based on their cationicity, arginine-rich composition and the presence of three intrapeptide disulfide bonds, as well as their broad spectrum antimicrobial activity. However, theta defensins are distinguishable from previously described defensins in that theta defensins are cyclic peptides, which lack a free amino or carboxyl terminus, and are shorter than previously described defensins.

The theta defensins are exemplified by the peptides shown as SEQ ID NOS:1–3 (FIG. 1). RTD-1 contains 18 amino acids, wherein the amino terminus of the first amino acid (Gly) is linked to the carboxyl terminus of the last amino acid (Arg) through a peptide bond, and wherein disulfide bonds are formed between Cys-3 and Cys-16, Cys-5 and Cys-14, and Cys-7 and Cys-12. For convenience of discussion, reference to an amino acid position in a theta defensin, or an analog thereof, is made with respect to the amino acid position in the linear form of theta defensin shown as SEQ ID NOS:1–3 or of the theta defensin sequence Xaa1-Xaa2-Xaa3-Xaa4-Xaa5-Xaa1-Xaa6-Xaa4-Xaa4-Xaa1-Xaa1-Xaa6-Xaa4-Xaa5-Xaa1-Xaa3-Xaa7-Xaa8; or of the theta defensin sequence Xaa1-Xaa2-Xaa3-Xaa4-Xaa5-Xaa1-Xaa6-Xaa7-Xaa8-Xaa1-Xaa2-Xaa6-Xaa4-Xaa5-Xaa1-Xaa3-Xaa7-Xaa8; or of the theta defensin sequence Xaa1-Xaa1-Xaa3-Xaa4-Xaa5-Xaa1-Xaa6-Xaa4-Xaa4-Xaa1-Xaa1-Xaa6-Xaa4-Xaa5-Xaa1-Xaa3-Xaa4-Xaa4. As such, the amino acids are referred to as positions 1 through 18, starting with the Gly residue in (position 1; SEQ ID NO:1) and ending with Arg (position 18).

A theta defensin having the amino acid sequence of SEQ ID NOS:1–3 can be obtained by purification of the native peptide from a natural source by expression of a recombinant theta defensin, or by chemical synthesis (see Example I). A theta defensin having the amino acid sequence of SEQ ID NOS:1–3, or of the theta defensin sequence Xaa1-Xaa2-Xaa3-Xaa4-Xaa5-Xaa1-Xaa6-Xaa4-Xaa4-Xaa1-Xaa1-Xaa6-Xaa4-Xaa5-Xaa1-Xaa3-Xaa7-Xaa8; or of the theta defensin sequence Xaa1-Xaa2-Xaa3-Xaa4-Xaa5-Xaa1-Xaa6-Xaa7-Xaa8-Xaa1-Xaa2-Xaa6-Xaa4-Xaa5-Xaa1-Xaa3-Xaa7-Xaa8; or of the theta defensin sequence Xaa1-Xaa1-Xaa3-Xaa4-Xaa5-Xaa1-Xaa6-Xaa4-Xaa4-Xaa1-Xaa1-Xaa6-Xaa4-Xaa5-Xaa1-Xaa3-Xaa4-Xaa4, also can be chemically synthesized using routine methods of solid phase synthesis or can be expressed from a recombinant nucleic acid molecule encoding the theta defensin.

The invention additionally provides a theta-defensin comprising the amino acid sequence Arg-Cys-Ile-Cys-Thr-Arg-Gly-Phe-Cys (SEQ ID NO:9) or Arg-Cys-Leu-Cys-Arg-Arg-Gly-Val-Cys (SEQ ID NO:11). Also provided is a theta defensin analog comprising the amino acid sequence Xaa4-Xaa5-Xaa1-Xaa3-Xaa7-Xaa8-Xaa1-Xaa2-Xaa3, and a theta defensin analog comprising the amino acid sequence Xaa4-Xaa5-Xaa1-Xaa6-Xaa4-Xaa4-Xaa1-Xaa1-Xaa6. Further provided is a theta defensin having the amino acid sequence Gly-Phe-Cys-Arg-Cys-Ile-Cys-Thr-Arg-Gly-Phe-Cys-Arg-Cys-Ile-Cys-Thr-Arg (SEQ ID NO:2). The invention also provides a theta defensin having the amino acid sequence Gly-Val-Cys-Arg-Cys-Leu-Cys-Arg-Arg-Gly-Val-Cys-Arg-Cys-Leu-Cys-Arg-Arg (SEQ ID NO:3).

As disclosed herein, the RTD1a and RTD1b peptides can form heterodimers (RTD1) and homodimers (RTD-2 and RTD-3; see Example I). Similarly, an analog of the RTD1a peptide, such as Xaa4-Xaa5-Xaa1-Xaa3-Xaa7-Xaa8-Xaa1-Xaa2-Xaa3, and an analog of the RTD1b peptide, such as Xaa4-Xaa5-Xaa1-Xaa6-Xaa4-Xaa4-Xaa1-Xaa1-Xaa6, can form heterodimers and homodimers. Such heterodimers and homodimers are theta defensin analogs of the invention. The dimers can be linked by a peptide bond and contain intrachain disulfide crosslinks (FIG. 1).

In general, a precursor theta defensin is obtained following chemical synthesis of the peptide, since the newly synthesized peptide is not cyclized and does not contain the appropriate intrachain crosslinking. Similarly, expression of a recombinant nucleic acid molecule encoding a theta defensin generally results in the production of a precursor theta defensin peptide, unless the peptide is expressed in a cell that can effect formation of the appropriate bonds. Accordingly, the term "precursor," when used in reference to a theta defensin peptide, means a form of the peptide that lacks a peptide bond between the amino terminal and carboxyl terminal amino acids or lacks at least one of the three disulfide bonds characteristic of a theta defensin. Such precursor peptides can be converted into a mature cyclic theta defensin containing, for example, one, two or three disulfide bonds by exposing the precursor peptide to the appropriate conditions for effecting formation of the intrapeptide crosslinks (see Example I). However, precursor theta defensins also are contemplated as useful in the present invention so long as the precursor has antimicrobial activity or can be converted to an antimicrobial form.

A theta defensin or theta defensin analog can be prepared by solid phase methods. Theta defensin analogs are synthesized based on SEQ ID NOS:1, 2 or 3 (see Example I). For example, a natural theta defensin can be modified to a form having a free amino or carboxyl terminus, which can optionally be amidated (see Table 1). In addition, an analog can be generated by substituting one or more amino acids of SEQ ID NOS:1, 2 or 3, as desired, particularly by incorporating conservative amino acid substitutions. Such conservative amino acid substitutions are well known and include, for example, the substitution of an amino acid having a small hydrophobic side chain with another such amino acid (for example, Ala for Gly) or the substitution of one basic residue with another basic residue (for example, Lys for Arg). Similar conservative amino acid substitutions in other antimicrobial peptides such as indolicidin resulted in the production of indolicidin analogs that maintained their broad spectrum antimicrobial activity (see U.S. Pat. No. 5,547,939, issued Aug. 20, 1996, which is incorporated herein by reference). Thus, a theta defensin analog having, for example, a substitution of Leu-6 with a Val, Ile or Ala residue, or a substitution of Arg-8 or Arg-9 or Arg-13 or Arg-18 with a Lys residue similarly can be expected to maintain broad spectrum antimicrobial activity.

A theta defensin analog also can have substitutions of the cysteine residues involved in a disulfide bond, with amino acids that can form an intrachain crosslink, for example, with tryptophan residues, which can form a di-tryptophan crosslink. Similarly to naturally occurring indolicidin, which is a linear antimicrobial peptide, indolicidin analogs having an intrachain di-tryptophan crosslink also have antimicrobial activity. Furthermore, substitution of the Trp residues involved in the di-tryptophan crosslink in an indolicidin analog with Cys residues results in an indolicidin analog that has an intrachain disulfide crosslink and exhibits broad spectrum antimicrobial activity. By analogy to such indolicidin analogs, a theta defensin analog can contain, in place of one or more of the characteristic disulfide bonds, one or more corresponding di-tryptophan, lactam or lanthionine crosslinks. For example, a crosslink in a theta defensin analog can be formed, for example, between two Trp residues, which form a di-tryptophan crosslink. In addition, a crosslink can be a monosulfide bond formed by a lanthionine residue. A crosslink also can be formed between other amino acid side chains, for example, a lactam crosslink formed by a transamidation reaction between the side chains of an acidic amino acid and a basic amino acid, such as between the γ-carboxyl group of Glu (or β-carboxyl group of Asp) and the ε-amino group of Lys; or can be a lactone produced, for example, by a crosslink between the hydroxy group of Ser and the γ-carboxyl group of Glu (or β-carboxyl group of Asp); or a covalent bond formed, for example, between two amino acids, one or both of which have a modified side chain.

A theta defensin peptide can also have the amino acid sequence Xaa1-Xaa2-Xaa9-Xaa4-Xaa10-Xaa1-Xaa11-Xaa4-Xaa4-Xaa1-Xaa1-Xaa12-Xaa4-Xaa13-Xaa1-Xaa14-Xaa7-Xaa8; or the amino acid sequence Xaa1-Xaa2-Xaa9-Xaa4-Xaa10-Xaa1-Xaa11-Xaa7-Xaa8-Xaa1-Xaa2-Xaa12-Xaa4-Xaa13-Xaa1-Xaa14-Xaa7-Xaa8; or the amino acid sequence Xaa1-Xaa1-Xaa9-Xaa4-Xaa10-Xaa1-Xaa11-Xaa4-Xaa4-Xaa1-Xaa1-Xaa12-Xaa4-Xaa13-Xaa1-Xaa14-Xaa4-Xaa4, wherein Xaa1 independently is an aliphatic amino acid such as Gly, Ile, Leu, Val or Ala; Xaa2 is an aromatic amino acid such as Phe, Trp or Tyr; Xaa4 independently is Arg or Lys; Xaa7 is Thr or Ser; Xaa8 is Arg or Lys; Xaa9 is Glu, Asp, Lys or Ser; Xaa10 is Glu, Asp, Lys or Ser; Xaa11 is Glu, Asp, Lys or Ser; Xaa12 is Glu, Asp, Lys or Ser; Xaa13 is Glu, Asp, Lys or Ser; Xaa14 is Glu, Asp, Lys or Ser. In such a theta defensin peptide, an intrachain crosslink can be formed between two amino acids, Xaa9 and Xaa14; Xaa10 and Xaa13; or Xaa11 and Xaa12, which correspond to the same position as disulfide crosslinks in natural theta defensin. The intrachain crosslink can be, for example, a lactam or lactone. Such a theta defensin can be a linear peptide and can optionally be amidated at the C-terminus.

In theta defensin peptides having less than three crosslinks, as found in native theta defensin, the amino acids at the positions corresponding to the native crosslinks, amino acids Xaa3, Xaa5 and Xaa6 in SEQ ID NO:1, can be modified. For example if positions Xaa3 are disulfide crosslinked, the amino acids at position Xaa5 and Xaa6 can be non cysteine residues, for example, a hydrophobic amino acid such as Tyr, Val, Ile, Leu, Met, Phe or Trp; a small amino acid such as Gly, Ser, Ala, or Thr; or a large polar amino acid such as Asn or Gln.

If desired, a theta defensin analog of the invention can have one or more amino acid deletions or additions as compared to SEQ ID NOS:1, 2 or 3, again, by analogy to indolicidin analogs, which can have a carboxyl terminal amino acid deletion or as many as five amino terminal amino acid deletions, yet still maintain broad spectrum antimicrobial activity. Thus, it can be expected that theta defensin analogs having one or a few deletions or additions at selected positions in the theta defensin sequence also will maintain broad spectrum antimicrobial activity and, as such, are considered functional fragments of a theta defensin (see Examples II and III). As used herein, a "functional fragment" when used in reference to a theta defensin is a portion of a theta defensin that still retains some or all of the antimicrobial activity of a theta defensin. The antimicrobial activity of a theta defensin analog, or a functional fragment thereof, containing one or more amino acid substitutions, deletions or additions as compared to SEQ ID NO:1 can be confirmed using assays as disclosed herein or otherwise known in the art.

For example, a residue added to a theta defensin peptide or peptide analog can be a homoserine residue. As shown in Example IV, addition of a homoserine residue can advantageously enhance antimicrobial activity of the theta defensin.

As used herein, the term "amino acid" is used in its broadest sense to mean the naturally occurring amino acids as well as non-naturally occurring amino acids, including amino acid analogs. Thus, reference herein to an amino acid includes, for example, naturally occurring proteogenic (L)-amino acids, as well as (D)-amino acids, chemically modified amino acids such as amino acid analogs, naturally occurring non-proteogenic amino acids such as norleucine, and chemically synthesized compounds having properties known in the art to be characteristic of an amino acid. As used herein, the term "proteogenic" indicates that the amino acid can be incorporated into a protein in a cell through a metabolic pathway.

Theta defensin having the amino acid sequence of SEQ ID NOS:1–3 were chemically synthesized as a linear precursor peptide using solid phase Fmoc chemistry (see Example I). The linear peptide was subjected to reducing conditions, then oxidized to allow formation of the disulfide bonds, and treated with ethylenediaminecarbodiimide to cyclize the peptide. The synthesized cyclic theta defensin was characterized by reverse phase-high performance liquid chromatography (RP-HPLC), MALDI-TOF mass spectrometry and circular dichroism (CD) and comigrated with native theta defensin by acid-urea PAGE. The synthetic cyclic theta defensin also demonstrated broad spectrum antimicrobial activity.

Methods for synthesizing a theta defensin or theta defensin analog are well known to those skilled in the art (U.S. Pat. No. 6,335,318, issued Jan. 1, 2002; WO 00/68265; Tang et al., *Science* 286:498–502 (1999)). A linear peptide of an amino acid sequence corresponding to the amino acid sequence of theta defensin or an analog thereof can be synthesized. One or more crosslink bonds within the linear peptide can be formed, and the peptide cyclized by linking the carboxyl and amino termini to form a cyclic peptide. The crosslink formed can be a disulfide, lanthionine, lactam or lactone. The cysteine residues used in the linear peptide can be in a pre-formed activated ester form. If a disulfide crosslink is formed between two cysteines, the crosslink can be formed by oxidation. The formation of a peptide bond between the amino and carboxyl termini can be advantageously mediated by placing the carboxyl terminus and amino terminus of the linear peptide each approximately the same number of amino acids from the nearest cysteine.

An advantage of using chemical synthesis to prepare a theta defensin or theta defensin analog is that (D)-amino acids can be substituted for (L)-amino acids, if desired. The incorporation of one or more (D)-amino acids into a theta defensin analog can confer, for example, additional stability of the peptide in vitro or, particularly, in vivo, since endogenous endoproteases generally are ineffective against peptides containing (D)-amino acids. Naturally occurring antimicrobial peptides that have been chemically synthesized to contain (D)-amino acids maintain their antimicrobial activity (Wade et al., *Proc. Natl. Acad. Sci. USA* 87:4761–4765 (1990), which is incorporated herein by reference).

If desired, the reactive side group of one or more amino acids in a theta defensin or theta defensin analog can be modified or amino acid derivatives can be incorporated into the peptide (see, for example, *Protein Engineering: A practical approach* (IRL Press 1992); Bodanszky, *Principles of Peptide Synthesis* (Springer-Verlag 1984), each of which is incorporated herein by reference). Selective modification of a reactive group, other than those involved in formation of the three intrachain crosslinks characteristic of a defensin, can impart desirable characteristics upon a theta defensin analog, although modifications that allow the formation of intrachain crosslinks at the appropriate positions also can be effected. The choice of including such a modification is determined, in part, by the characteristics required of the peptide. Such modifications can result, for example, in theta defensin analogs having greater antimicrobial selectivity or potency than naturally occurring theta defensin. For example, a theta defensin analog having a free carboxyl terminus can be modified so that the C-terminus is amidated (see Table 1). Similarly, a theta defensin analog having a free amino terminus can be modified so that the N-terminus is acetylated.

The theta defensins are polypeptides having antimicrobial activity. As used herein, the term "polypeptide" when used in reference to a theta defensin is intended to refer to a peptide or polypeptide of two or more amino acids. The term is similarly intended to refer to derivatives, analogues and functional mimetics thereof. For example, derivatives can include chemical modifications of the polypeptide such as alkylation, acylation, carbamylation, iodination, or any modification which derivatizes the polypeptide. Analogues can include modified amino acids, for example, hydroxyproline or carboxyglutamate, and can include amino acids that are not linked by peptide bonds. Mimetics encompass chemicals containing chemical moieties that mimic the function of the polypeptide. For example, if a polypeptide contains two charged chemical moieties having functional activity, a mimetic places two charged chemical moieties in a spatial orientation and constrained structure so that the charged chemical function is maintained in three-dimensional space. Thus, a mimetic, which orients functional groups that provide the antimicrobial function of a theta defensin, are included within the meaning of a theta defensin derivative. All of these modifications are included within the term "polypeptide" so long as the polypeptide retains its antimicrobial function.

A theta defensin can incorporate polypeptide derivatives. Peptide derivatives are well known in the art (see, for example, U.S. Pat. No. 5,804,558, issued Sep. 8, 1998). For example, certain commonly encountered amino acids, which are not encoded by the genetic code, include, for example, beta-alanine (beta-Ala), or other omega-amino acids, such as 3-aminopropionic, 2,3-diaminopropionic (2,3-diaP), 4-aminobutyric and so forth, alpha-aminisobutyric acid (Aib), sarcosine (Sar), ornithine (Orn), citrulline (Cit), t-butylalanine (t-BuA), t-butylglycine (t-BuG), N-methylisoleucine (N-MeIle), phenylglycine (Phg), and cyclohexylalanine (Cha), norleucine (Nle), 2-naphthylalanine (2-Nal); 1,2,3,4-tetrahydroisoquinoline-3-carboxylic acid (Tic); β-2-thienylalanine (Thi); methionine sulfoxide (MSO); and homoarginine (Har).

In a theta defensin peptide or peptide analog thereof, one or more amide linkages (—CO—NH—) can be replaced with another linkage which is an isostere such as —CH$_2$NH—, —CH$_2$S—, —CH$_2$CH$_2$, —CH═CH— (cis and trans), —COCH$_2$—, —CH(OH)CH$_2$— and —CH$_2$SO—. This replacement can be made by methods known in the art (see, for example, Spatola, *Vega Data* Vol. 1, Issue 3, (1983); Spatola, in *Chemistry and Biochemistry of Amino Acids Peptides and Proteins,* Weinstein, ed., Marcel Dekker, New York, p. 267 (1983); Morley, J. S., *Trends Pharm. Sci.* pp. 463–468 (1980); Hudson et al., *Int. J. Pept. Prot. Res.* 14:177–185 (1979); Spatola et al., *Life Sci.* 38:1243–1249 (1986); Hann, *J. Chem. Soc. Perkin Trans. I* 307–314 (1982); Almquist et al., *J. Med. Chem.* 23:1392–1398 (1980); Jennings-White et al., *Tetrahedron Lett.* 23:2533 (1982); Szelke et al., EP 45665 (1982); Holladay et al., *Tetrahedron Lett.* 24:4401–4404 (1983); and Hruby, *Life Sci.* 31:189–199 (1982)).

In addition to polypeptide derivatives of a theta defensin, a chemical mimetic of a theta defensin peptide can be used. As described above, mimetics contain chemical functional groups that mimic the function of a theta defensin. Such a mimetic chemical can orient functional groups on a theta defensin peptide sufficient for antimicrobial activity. A mimetic places the functional chemical moieties in a spatial orientation and constrained structure so that the chemical function is maintained in three-dimensional space. Thus, a mimetic orients chemical functional groups that provide the theta defensin function of antimicrobial activity in an orientation that mimics the structure of a theta defensin.

A molecular model of a theta defensin has been previously described (see U.S. Pat. No. 6,335,318, issued Jan. 1, 2002; WO 00/68265). Using the molecular model of theta defensin, one skilled in the art can identify a chemical such as a peptidomimetic. As used herein, the term "peptidomimetic" is used broadly to mean a peptide-like molecule that has a similar structure and activity as a theta defensin. With respect to the theta defensin peptides of the invention, peptidomimetics, which include chemically modified peptides, peptide-like molecules containing non-naturally occurring amino acids, peptoids and the like, have the antimicrobial activity upon which the peptidomimetic is derived (see, for example, "Burger's Medicinal Chemistry and Drug Discovery" 5th ed., vols. 1 to 3 (ed. M. E. Wolff; Wiley Interscience 1995)). Peptidomimetics provide various advantages over a peptide, including that a peptidomimetic can be more stable during passage through the digestive tract and, therefore, useful for oral administration.

Methods for identifying a peptidomimetic are well known in the art and include, for example, the screening of databases that contain libraries of potential peptidomimetics. For example, the Cambridge Structural Database contains a collection of greater than 300,000 compounds that have known crystal structures (Allen et al., Acta Crystallogr. Section B, 35:2331 (1979)). This structural depository is continually updated as new crystal structures are determined and can be screened for compounds having suitable shapes, for example, the same shape as a theta defensin peptide. Another database, the Available Chemicals Directory (Molecular Design Limited, Information Systems; San Leandro Calif.), contains about compounds that are commercially available and also can be searched to identify potential peptidomimetics of a theta defensin peptide.

As used herein, the term "antimicrobial selectivity" refers to the relative amount of antimicrobial activity of theta defensin, or a theta defensin analog, against a microorganism as compared to its activity against the environment to which it is administered, particularly its activity against normal cells in a treated individual. For example, a theta defensin analog that is characterized by having antimicrobial activity that is equivalent to native theta defensin, but having decreased hemolytic activity as compared to native theta defensin, is considered to have greater antimicrobial selectivity than native theta defensin.

As disclosed herein, theta defensin (SEQ ID NOS:1–3) and analogs thereof have broad spectrum antimicrobial activity. As used herein, the term "broad spectrum," when used in reference to the antimicrobial activity of theta defensin or an analog thereof, refers to the ability of the peptide to reduce or inhibit the survival or proliferative ability of various viruses, prokaryotic and eukaryotic microorganisms. For example, theta defensin (SEQ ID NOS:1–3) and analogs thereof can exhibit antimicrobial activity against protozoans such as Giardia lamblia, Chlamydia sp. and Acanthamoeba sp.; viruses, particularly enveloped viruses such as herpes simplex virus and HIV-1; fungi such as Cryptococcus and Candida; various genera of gram negative and gram positive bacteria, including Escherichia, Salmonella and Staphylococcus and Listeria; and parasitic helminths such as liver flukes. Antimicrobial activity can occur through "microbicidal inhibition," which refers to the ability of a theta defensin or theta defensin analog to reduce or inhibit the survival of a microorganism by killing or irreversibly damaging it, or through "microbistatic inhibition," which refers to the ability of the theta defensin or theta defensin analog to reduce or inhibit the growth or proliferative ability of a target microorganism without necessarily killing it. The invention theta defensins and theta defensin analogs are also active in the presence of physiological salt and serum (see Example II).

A precursor theta defensin or theta defensin analog can be expressed from a recombinant nucleic acid molecule encoding the peptide. For example, a nucleic acid encoding a theta defensin peptide or precursor can be used to recombinantly express a theta defensin peptide or analog thereof. A nucleic acid molecule encoding a theta defensin can be chemically synthesized or can be cloned from a cell that contains a theta defensin gene or encodes a theta defensin mRNA, which can be converted to a cDNA. A nucleic acid molecule encoding a precursor theta defensin can be prepared by chemical synthesis, based on the disclosed theta defensin amino acid sequence (SEQ ID NOS:1–3) and knowledge in the art of codons encoding each amino acid.

In addition, a nucleic acid encoding a theta defensin analog having a free amino and carboxyl terminus can be synthesized and used to recombinantly express the theta defensin analog. Thus, a theta defensin analog can be expressed as a single, contiguous polypeptide without the need for trans splicing of peptides, as with the in vivo synthesis of native RTD-1, 2, and 3. Accordingly, the invention provides nucleic acid molecules encoding theta defensin analogs of the invention, including the theta defensin analogs referenced as SEQ ID NOS:13–31 and other analogs disclosed herein.

RTD1 is encoded by two similar cDNAs, termed RTD1a (SEQ ID NO:4) and RTD1b (SEQ ID NO:6), each of which contains 9 of the 18 amino acid residues in the mature RTD-1 peptide (see FIG. 2). The cDNAs encode separate peptides, which become cyclized by formation of peptide bonds that join the two peptides.

A nucleic acid molecule encoding a precursor theta defensin or a theta defensin analog thereof can be cloned into an appropriate vector, particularly an expression vector, and the encoded peptide can be expressed in a host cell or using an in vitro transcription/translation reaction, thereby providing a means to obtain large amounts of the theta defensin. Optionally, the recombinant peptide can be produced as a fusion with a tag, such as a His tag, to facilitate identification and purification. Suitable vectors, host cells, in vitro transcription/translation systems, and tag sequences are well known in the art and commercially available.

Example IV shows the production of recombinant RTD-1 and a homoserine analog of RTD-1. Recombinant and synthetic versions of RTD-1 had equivalent antimicrobial activities.

An anti-theta defensin antibody can be used to substantially purify theta defensin from a sample. For example, a theta defensin antibody can be used to isolate naturally occurring theta defensin from leukocytes or from a cell expressing a recombinant nucleic acid molecule encoding a theta defensin or theta defensin analog.

A theta defensin or analog thereof having antimicrobial activity can be applied to an environment capable of sustaining the survival or growth of a microorganism or to an environment at risk of supporting such survival or growth, thus providing a means for reducing or inhibiting microbial growth or survival. Accordingly, a theta defensin or a theta defensin analog can be used to reduce or inhibit microbial growth by contacting an environment capable of sustaining microbial growth or survival with the antimicrobial peptide.

Thus, the invention provides a method of reducing or inhibiting growth or survival of a microorganism in an environment capable of sustaining the growth or survival of the microorganism by administering an effective amount of a theta defensin analog of the invention to the environment, thereby reducing or inhibiting the growth or survival of the microorganism. It is understood that any of the theta defensin analogs of the invention can be used in a method of reducing or inhibiting growth or survival of a microorganism.

As used herein, reference to "an environment capable of sustaining survival or growth of a microorganism" means a gaseous, liquid or solid material, including a living organism, in or upon which a microorganism can live or propagate. In view of the broad range of environments that allow the survival or growth of microorganisms as diverse, for example, as viruses, bacteria, fungi, protozoans and helminths, and further in view of the disclosed effectiveness of a theta defensin and theta defensin analogs against a broad spectrum of such microorganisms, the range of such environments that can be treated using a theta defensin or theta defensin analog includes, for example, a tissue or bodily fluid of an organism such as a human; a liquid such as water or an aqueous solution such as contact lens solution or eyewash solution; a food such as a food crop, a food product or a food extract; and an object such as the surface of an instrument used, for example, to prepare food or to perform surgery; and a gas such as that used for anesthetization in preparation for surgery.

A method of the invention encompasses administering to the environment an effective amount of a theta defensin analog of the invention such that the antimicrobial peptide can contact a microorganism in the environment, thereby reducing or inhibiting the ability of the microorganism to grow or survive. A theta defensin analog can be used in a variety of procedures for reducing or inhibiting the survival or growth of microorganisms, including the microbicidal inhibition of survival of a microorganism as well as the microbistatic inhibition of growth. As such, a theta defensin analog can be used, for example, as a therapeutic agent, a food preservative, a disinfectant or a medicament.

A theta defensin analog can be particularly useful as a therapeutic agent for treating a patient suffering from a bacterial, viral, fungal or other infection due to a microorganism susceptible to the antimicrobial activity of the theta defensin or theta defensin analog. For example, a cyclic form of a theta defensin can be used since a cyclic theta defensin is particularly resistant to the activity of endogenous proteases and peptidases. Similarly, modified forms of a theta defensin such as the analogs disclosed herein can be resistant to protease digestion. Thus, a theta defensin analog can be used to treat an individual suffering from a pathology caused, at least in part, by microbial infection, by administering a theta defensin or theta defensin analog to the individual under conditions that allow the theta defensin or analog thereof to contact the infecting microorganisms, thereby reducing or inhibiting the survival or growth of the microorganism and alleviating the severity of the infection.

For use as a therapeutic agent, the theta defensin or theta defensin analog can be formulated with a pharmaceutically acceptable carrier to produce a pharmaceutical composition, which can be administered to the individual, which can be a human or other mammal. A pharmaceutically acceptable carrier can be, for example, water, sodium phosphate buffer, phosphate buffered saline, normal saline or Ringer's solution or other physiologically buffered saline, or other solvent or vehicle such as a glycol, glycerol, an oil such as olive oil or an injectable organic ester.

A pharmaceutically acceptable carrier can contain physiologically acceptable compounds that act, for example, to stabilize or increase the absorption of the theta defensin or analog thereof. Such physiologically acceptable compounds include, for example, carbohydrates such as glucose, sucrose or dextrans; antioxidants such as ascorbic acid or glutathione; chelating agents such as ethylenediamine tetraacetic acid (EDTA), which disrupts microbial membranes; divalent metal ions such as calcium or magnesium; low molecular weight proteins; or other stabilizers or excipients. One skilled in the art would know that the choice of a pharmaceutically acceptable carrier, including a physiologically acceptable compound, depends, for example, on the route of administration of the composition.

A pharmaceutical composition containing a theta defensin or analog thereof can be administered to an individual by various routes, including by intravenous, subcutaneous, intramuscular, intrathecal or intraperitoneal injection; orally, as an aerosol spray; or by intubation. If desired, the theta defensin or theta defensin analog can be incorporated into a liposome, a non-liposome lipid complex, or other polymer matrix, which further can have incorporated therein, for example, a second drug useful for treating the individual. Use, for example, of an antimicrobial indolicidin peptide incorporated into liposomes has been demonstrated to have antifungal activity in vivo (Ahmad et al., *Biochem. Biophys. Acta* 1237:109–114 (1995), which is incorporated herein by reference). Liposomes, which consist of phospholipids or other lipids, are nontoxic, physiologically acceptable and metabolizable carriers that are relatively simple to make and administer (Gregoriadis, *Liposome Technology, Vol.* 1 (CRC Press, Boca Raton Fla., 1984), which is incorporated herein by reference). The skilled artisan will select a particular route and method of administration based, for example, on the location of a microorganism in a subject, the particular characteristics of the microorganism, and the specific theta defensin or theta defensin analog that is administered.

In order to exhibit antimicrobial activity in an environment, an effective amount of a theta defensin analog is administered to the environment. As used herein, the term "effective amount" refers to the amount of a theta defensin analog that reduces or inhibits the survival or growth of a microorganism in an environment. In particular, an effective amount of a theta defensin analog produces only minimal effects against the environment, although the level of an acceptable deleterious effect is weighed against the benefit caused by the antimicrobial effect.

A theta defensin analog can be administered to a subject such as a human systemically at a dose ranging from 1 to 100 mg/kg body weight, for example, at a dose of about 10 to 80 mg/kg, particularly about 10 to 50 mg/kg. A theta defensin analog also can be incorporated into liposomes, if desired, in which case the total amount administered to a subject generally can be reduced. Furthermore, a theta defensin analog can be administered orally to a subject at a dose ranging from about 1 to 100 mg/kg body weight, for example at a dose of about 10 to 200 mg/kg, in particular about 20 to 100 mg/kg. In addition, a theta defensin analog can be administered topically to an environment, which can be a human subject, or can be placed in a solution, at a concentration of about 0.1 to 10 mg/ml, for example, at a concentration of about 0.5 to 5 mg/ml. Although theta defensins generally are effective in microgram per ml amounts, an effective amount for administration to a particular environment will depend, in part, on the environment. For example, when administered to a mammal such as a human, a theta defensin analog, in addition to having antimicrobial activity, can have an undesirable side effect. The skilled artisan will recognize that the level of such side effects must be considered in prescribing a treatment and must be monitored during the treatment period, and will adjust the amount of the theta defensin analog that is administered accordingly.

An effective amount of a theta defensin analog also will vary depending, for example, on the characteristics of the target microorganism, the extent of prior infection or growth and the specific theta defensin analog that is administered. In addition, an effective amount depends on the form in which the theta defensin is administered. For example, incorporation of another antimicrobial peptide, indolicidin, into liposomes allowed administration of a higher amount of the peptide than "free" indolicidin, without producing unacceptable side effects, such that fungal infection in mice could be cured (Ahmad et al., supra, 1995).

Furthermore, the effective amount of a theta defensin analog to be administered to an individual can be adjusted if the theta defensin is administered in combination with another antimicrobial compound such as an antibiotic. Thus, one skilled in the art can adjust the dosage of the theta defensin analog so that the combination of the theta defensin analog and other antimicrobial therapy is optimally effective for inhibiting the growth or survival of a microorganism in an environment.

The invention additionally provides a method of decreasing an inflammatory response using a theta defensin or analog thereof. As used herein, decreasing an inflammatory response refers to a decrease of one or more responses associated with inflammation. Inflammation is a physiologic response to a variety of stimuli such as infections and tissue injury. Neutrophils are the predominant cell type infiltrating an area of inflammation in the early stages of an inflammatory response. A variety of inflammatory mediators are released that serve to trigger or enhance specific aspects of the inflammatory response, including chemokines, lipids such as arachidonic acid, prostaglandins and leukotrienes, and cytokines. For example, as shown in Example V, lipopolysaccharide (LPS) was used as a model of inflammation and was found to stimulate the production of several cytokines including tumor necrosis factor-α, several interleukins (IL-1β, 2, 5, 6, 7, and 10), several chemokines (MIP-1-δ, RANTES) and growth stimulatory factors (GM-CSF, SCF, and TGF-β$_1$). The addition of theta defensins reduced the levels of many cytokines that are released by LPS-stimulated cells, indicating that theta defensins can play a role during an inflammatory response. Reduction of pro-inflammatory cytokines such as TNF-α and IL-1β by RTD-1 indicates the anti-inflammatory property of the peptide are mediated through the regulation of cytokine production. Accordingly, theta defensins and analogs thereof can be used to decrease or inhibit the expression of pro-inflammatory molecules. Exemplary pro-inflammatory molecules include tumor necrosis factor-α, interleukin-1β (IL-1β), IL-2, IL-5, IL-6, IL-7, and IL-10, chemokines such as MIP-1-δ and RANTES, and growth stimulatory factors such as GM-CSF, SCF, and TGF-β1. Decreasing or inhibiting these or other signs of inflammation can be mediated by a theta defensin or analog thereof.

It is understood that modifications which do not substantially affect the activity of the various embodiments of this invention are also provided within the definition of the invention provided herein. Accordingly, the following examples are intended to illustrate but not limit the present invention.

EXAMPLE I

Isolation, Synthesis, and Antimicrobial Activities of Homodimeric Theta Defensins from Rhesus Macaque Leukocytes This example describes the isolation, synthesis and antimicrobial properties of RTD-1, 2 and 3.

Peptide synthesis, disulfide formation and cyclization of theta defensins were performed. Peptide synthesis was performed essentially as described for RTD-1 (Tang et al., Science 286:498–502 (1999)). Peptide sequences corresponding to open-chain versions of RTD-2 and 3 were assembled at 0.2 mmol scale on Fmoc-Arg(2,2,4,6,7-pentamethyldihydro-benzofuran-5-sulfonyl; Pbf) polyethyleneglycol-polystyrene resin with a Milligen 9050 automated synthesizer. Arg, Cys, and Thr side chains were protected with Pbf, triphenylmethyl (Trt), and tert-butyl (tBu) groups, respectively. All amino acids except cysteine were coupled with O-(7-azabenzotriazol-1-yl)-1,13,3-tetramethyluronium hexafluorophosphate/N,N-diisopropylethylamine (HATU/DIEA) activation. Cysteine residues were coupled as the pre-formed pentafluorophenyl ester derivative. RTD-2 was assembled with double coupling of Thr and Ile residues. RTD-3 was assembled with double coupling at every cycle. Following chain assembly of RTD-2, the peptide-resin was cleaved and deprotected by incubation in 20 ml of reagent K (trifluoroacetic acid (TFA):phenol:water:thioanisole:1,2-ethanedithiol; 82.5:5:5:5:2.5; v/w/v/v/v; (van Abel et al., International J. Peptide Prot. Res. 45:401–409 (1995)) for 4 h at 22° C. with agitation. Cleavage and deprotection of RTD-3 were performed similarly but using reagent R (TFA:thioanisole: 1,2 ethanedithiol; 92:5:3; v/v/v; (van Abel et al., supra, 1995). Crude synthetic products were obtained by filtration and extraction with 30% acetic acid/dichloromethane as described for the synthesis of RTD-1 (Tang et al., supra, 1999).

Linear synthetic RTD-2 and 3 were purified by preparative $C_{18}$ RP-HPLC on a 25×100 mm DeltaPak $C_{18}$ cartridge (Waters, MA) developed with a 0.25% per min gradient of water-acetonitrile containing 0.1%TFA. Aliquots from eluant fractions were analyzed by matrix-assisted laser desorption/ionization-time-of-flight mass spectroscopy (MALDI-TOF MS), and those containing reduced/linear peptides were pooled and concentrated ten-fold by centrifugal evaporation. The peptide solutions were diluted to 100–200 µg/ml in 17.4 mM ammonium acetate, pH 8.0, and stirred vigorously in an open container for 18 h at 22° C. Peptide folding and oxidation were monitored by $C_{18}$ RP-HPLC and MALDI-TOF MS. The acyclic versions of RTD-2 and 3 were then purified by preparative $C_{18}$ RP-HPLC as described above. Purity was confirmed by analytical C18 RP-HPLC and acid-urea PAGE on 12.5% polyacrylamide gels (Selsted, Genetic Engineering: Principles and Methods, J. K. Setlow, ed., pp. 253–261, Plenum, New York (1993)). For MALDI-TOF MS, peptide solutions were mixed with an equal volume of 10 mg/ml α-cyano-4-hydroxy-cinnamic acid in 50/50 water-acetonitrile containing 0.1%TFA, and analyzed on a Voyager DE-RP Mass Spectrometer (PerSeptive Biosystems, CA) (Tang et al., supra, 1999).

Acyclic RTD-2 (5 mg) and RTD-3 (10 mg) were lyophilized, first from 25 mM hydrochloric acid (3 times), then twice from distilled water. Peptide cyclization was carried out by dissolving the lyophilized peptides at 200–300 μg/ml in 0.1% diisopropylethylamine/dimethylsulfoxide (DIPEA/DMSO; v/v) containing 60 molar equivalents of 1-ethyl-2-[3-dimethylaminopropyl]carbodiimide (EDC) and 20 equivalents of 1-hydroxybenzotriazole (HOBt). The solutions were sealed under nitrogen and stirred for 18 h at 22° C. The extent of peptide cyclization was determined by $C_{18}$ RP-HPLC and MALDI-TOF MS. Cyclic peptides were purified to homogeneity by C18 RP-HPLC with water-acetonitrile gradients (0.25% per min) containing 0.1%TFA and characterized by analytical C18 RP-HPLC, AU-PAGE, MALDI-TOF MS and amino acid analysis (Tang et al., supra, 1999).

For antibody production, rabbit anti-RTD-2 antibody was produced as described previously for the preparation of anti-RTD-1 antibody (Tang et al., supra, 1999). Briefly, acyclic RTD-2 (3.5 mg) was conjugated to ovalbumin (3.5 mg) with 0.1% glutaraldehyde in 7 ml of 100 mM sodium phosphate, pH 7.4, and stirred for 18 h at 22° C. The reaction was quenched with 300 mM glycine, and the peptide/ovalbumin conjugate was dialyzed exhaustively against water. Two New Zealand White rabbits were repetitively immunized using standard procedures until the anti-RTD-2 antiserum titer was 1:10,000 as determined by enzyme-linked immunosorbent assay. IgG-enriched preparations were obtained by chromatography on a DEAE Econo-Pac column according to the manufacturer's protocol (Bio-Rad, CA).

For western blot analysis, five percent acetic acid (HOAc) extracts of $1 \times 10^7$ leukocytes were resolved on a 12.5% acid-urea polyacrylamide gel and electroblotted to a 0.22 μm nitrocellulose membrane with a LKB Novablot apparatus (Pharmacia, NJ) using the semi-dry transfer method (Wang et al., Anal. Biochem. 253:225–230 (1997)). Replica blots were blocked with 5% non-fat dried milk in TTBS (100 mM tris buffer, pH 7.5, containing 0.9% sodium chloride and 0.1% Tween 20) for 1 h at 22° C. with agitation and incubated with a 1:150 dilution (in TTBS) of either rabbit anti-RTD-1 (Tang et al., supra, 1999), anti-RTD-2, or normal rabbit IgG for 1 h. Blots were washed with TTBS ($5 \times 10$ min) and developed with the ABC-Elite kit (Vector Labs, CA) as follows: 30 min incubation in biotinylated goat anti-rabbit IgG diluted 1:2,800 in TTBS, $3 \times 5$ min washes, and 30 min incubation in a 1:10 dilution of the avidin-horse radish peroxidase reagent. Immunopositive bands were visualized with Supersignal chemiluminescent substrate (Pierce, IL) on Hyperfilm (Amersham Pharmacia Biotech, England).

For purification of RTD-1, 2, and 3, Rhesus macaque peripheral blood leukocytes (>90% PMN) were extracted with 5% HOAc as previously described (Tang et al., Infect. Immun. 67:6139–6144 (1999); Tang et al., supra, 1999). RTD-1, 2 and 3 were purified from the acid extracts on a $4.6 \times 250$ mm Vydac C18 column using water-acetonitrile gradients containing 0.1% TFA or 0.1% phosphoric acid ($H_3PO_4$). Leukocyte extracts ($1–10 \times 10^7$ cell equivalents) were chromatographed using a 70 min 0–30% water-acetonitrile gradient containing 0.1%TFA. Eluant fractions were analyzed by MALDI-TOF MS for peptides with molecular masses of RTD-1, 2 and 3. Three θ-defensins were purified to homogeneity by successive rounds of RP-HPLC using the same solvent gradient but alternating between 0.1% TFA and 0.1% $H_3PO_4$ as the ion pairing reagent.

Purified RTD-1, 2 and 3 were characterized by MALDI-TOF MS, amino acid analysis, and acid urea-polyacrylamide gel electrophoresis (AU-PAGE). Cysteine content was determined by comparing the masses of the native peptides with those obtained following reduction of disulfides with 1,4-dithiothreitol and alkylation with iodoacetamide (Navale et al., Analytical Biochem. 267:125–134 (1999)). The amino acid compositions of RTD-1, 2, and 3 were determined on 6N HCl hydrolysates (2 h, 150° C.) as 6-aminoquinolyl-N-hydroxysuccinimidyl carbamate derivatives (Cohen and Michaud, Analytical Biochem. 211:279–287 (1993)). The absence of free N-termini was determined by Edman sequence analysis on 20–50 pmols of natural RTD-2 and 3. Natural peptides were compared with synthetic versions by RP-HPLC, acid-urea PAGE, amino acid analysis and MALDI-TOF mass spectroscopy.

To determine the antimicrobial activities of RTD-1, 2 and 3, the antimicrobial activities of synthetic RTD-1, 2 and 3 against bacteria (Staphylococcus aureus 502a and Escherichia coli ML35) and fungi (Candida albicans 16820 and Cryptococcus neoformans 271A) were assessed in an agar diffusion assay as described previously (Osapay et al., J. Biol. Chem. 275:12017–12022 (2000)). Briefly, 10-μl wells were bored in a 9-$cm^2$ plate of agarose, buffered with 10 mM 1,4-piperazinebis(ethanesulfonic acid) (PIPES), pH 7.4, containing 5 mM glucose, and seeded with $1 \times 10^6$ mid-log phase cells. Five-μl aliquots of peptides, dissolved in 0.01% HOAc at 10–300 μg/ml, were added to each well. After incubation at 37° C. for 2 h, the seeded agar was overlaid with molten agarose containing 6% trypticase soy broth (for bacteria) or Sabouraud dextrose broth (for fungi). Plates were incubated at 37° C. for 18–24 h, and antimicrobial activity was determined by measuring the diameter of clearing around each well.

Microbicidal activity of each peptide was determined by incubating $2 \times 10^6$ CFU/ml with peptides (0.5–12 μg/ml) in 50 μl of 10 mM PIPES buffer containing 5 mM glucose, pH 7.4. After 2 h incubation at 37° C., the cell suspensions were diluted 1:50 with 10 mM sodium phosphate buffer, pH 7.4, and exponentially spread with an Autoplate 400 (Spiral Biotech, MD) onto trypticase soy agar (bacteria) or Sabouraud dextrose agar (fungi). After 37° C. incubation for 18–48 h, colonies were counted and cell survival was expressed as CFU/ml.

Binding of RTD-1 and RTD-3 to E. coli ML35 was evaluated by incubating $2 \times 10^6$ log-phase bacteria with increasing peptide concentrations (0.5–8 μg/ml final) in 1 ml of 10 mM PIPES, pH 7.4, containing 5 mM glucose. After 2 h incubation at 37° C., the cell suspensions were centrifuged at 25,000×g, and the amounts of peptides in the supernatants were quantified by RP-HPLC. Binding of each peptide to E. coli was determined by comparing peptide recovery with control peptide samples that were not exposed to bacteria.

RTD-2 and RTD-3 are the predicted cyclic analogs of RTD-1, which would be produced by homodimeric splicing of nonapeptides from RTD1a and RTD1b, respectively (FIGS. 1 and 2). The peptides were synthesized using a protocol established for the synthesis of RTD-1, as described above. The linear peptides were purified by preparative RP-HPLC and the disulfide bond formation proceeded efficiently, giving >90% yield of monomeric, tridisulfide peptide as determined by quantitative RP-HPLC and MALDI-TOF MS. The yields for peptide cyclization were 60% for RTD-2 and 90% for RTD-3. The cyclic peptides were purified by $C_{18}$ RP-HPLC and characterized by AU-PAGE, amino acid analysis, and mass spectroscopy. RTD-2 (3.2 mg) and RTD-3 (9.2 mg) preparations were more than 99% pure, and were indistinguishable from the natural peptides.

Following isolation of natural RTD-1, 2 and 3, synthetic RTD-1, 2 and 3 had unique $R_f$ values on acid-urea PAGE due to the differing arginine content of each peptide. Acid extracts of Rhesus macaque leukocytes contained a band that co-migrated with synthetic RTD-1 on Coomassie-stained gel and western blots. RTD-1, and two additional immunopositive bands that co-migrated with RTD-2 and -3 synthetic standards, were detected in leukocyte extracts with anti-RTD-1 and anti-RTD-2 antibodies. These data indicate the presence of RTD-2 and RTD-3 in leukocyte extracts.

RTD-1, 2 and 3 were isolated from leukocyte extracts by RP-HPLC, as described above. Peptides with masses of RTD-1, 2, and 3 were detected in three peaks in the initial chromatographic step and the RP-HPLC elution times matched those of the respective synthetic peptides. Each θ-defensin was purified to homogeneity, and their identities were confirmed.

For characterization of RTD-2 and 3, sequence analysis of 20–50 pmol of purified RTD-2 and 3 yielded no amino acid signal, consistent with the θ-defensin cyclic structure. The molecular masses of natural RTD-2 and 3, determined by MALDI-TOF MS, matched the calculated values of the predicted sequences. The cysteine content of purified RTD-1, 2 and 3 was determined by comparing the molecular masses of native peptides with those that had been reduced and alkylated. Carboxamidomethylated RTD-1, 2 and 3 had molecular masses of 2430.5 a.m.u. (2430.7=theoretical), 2424.5 a.m.u. (2423.6=theoretical) and 2436.9 a.m.u. (2437.7=theoretical), respectively, consistent with the complete alkylation of six cysteine residues in each θ-defensin.

The compositions of natural RTD-1, 2, and 3 were determined by amino acid analysis of peptide hydrolysates. The composition of purified RTD-1 was in agreement with that previously reported (Tang et al., supra, 1999). The amino acid compositions of RTD-2 and 3 were consistent with those of the corresponding structures shown in FIG. 1.

The amount of each θ-defensin isolated from acid extracts of rhesus leukocytes was determined by quantitative amino acid analysis. The cellular abundance of θ-defensins in extracts of $5.8 \times 10^8$ cell equivalents was 107 µg (51.4 nmol) RTD-1, 8.8 µg (4.2 nmol) RTD-2, and 3.8 µg (1.8 nmol) RTD-3, giving relative cellular abundances of 29:2:1 (RTD-1:RTD-2:RTD-3). These data indicate that ten fold more heterodimeric RTD-1 is present in cells than the homodimeric homologs.

Synthetic RTD-1 was found to be biochemically and functionally equivalent to the natural peptide (Tang et al., supra, 1999). Like RTD-1, synthetic RTD-2 and 3 were undistinguishable from the natural isolates by amino acid analysis, MALDI-TOF mass spectroscopy, AU-PAGE and analytical RP-HPLC.

The antimicrobial activities of RTD-1, 2 and 3 were determined. The antimicrobial activities of RTD-1, 2 and 3 against *Staphylococcus aureus* 502a, *Escherichia coli* ML35 and yeast forms of *Candida albicans* 16820 and *Cryptococcus neoformans* 271A were assessed in agar diffusion assays. The activities of the three θ-defensins were equivalent against *S. aureus*, *C. albicans* and *C. neoformans*. However, RTD-3 was 2- to 3-fold less active than RTD-1 and RTD-2 against *E. coli* (FIG. 3).

Figure 4:
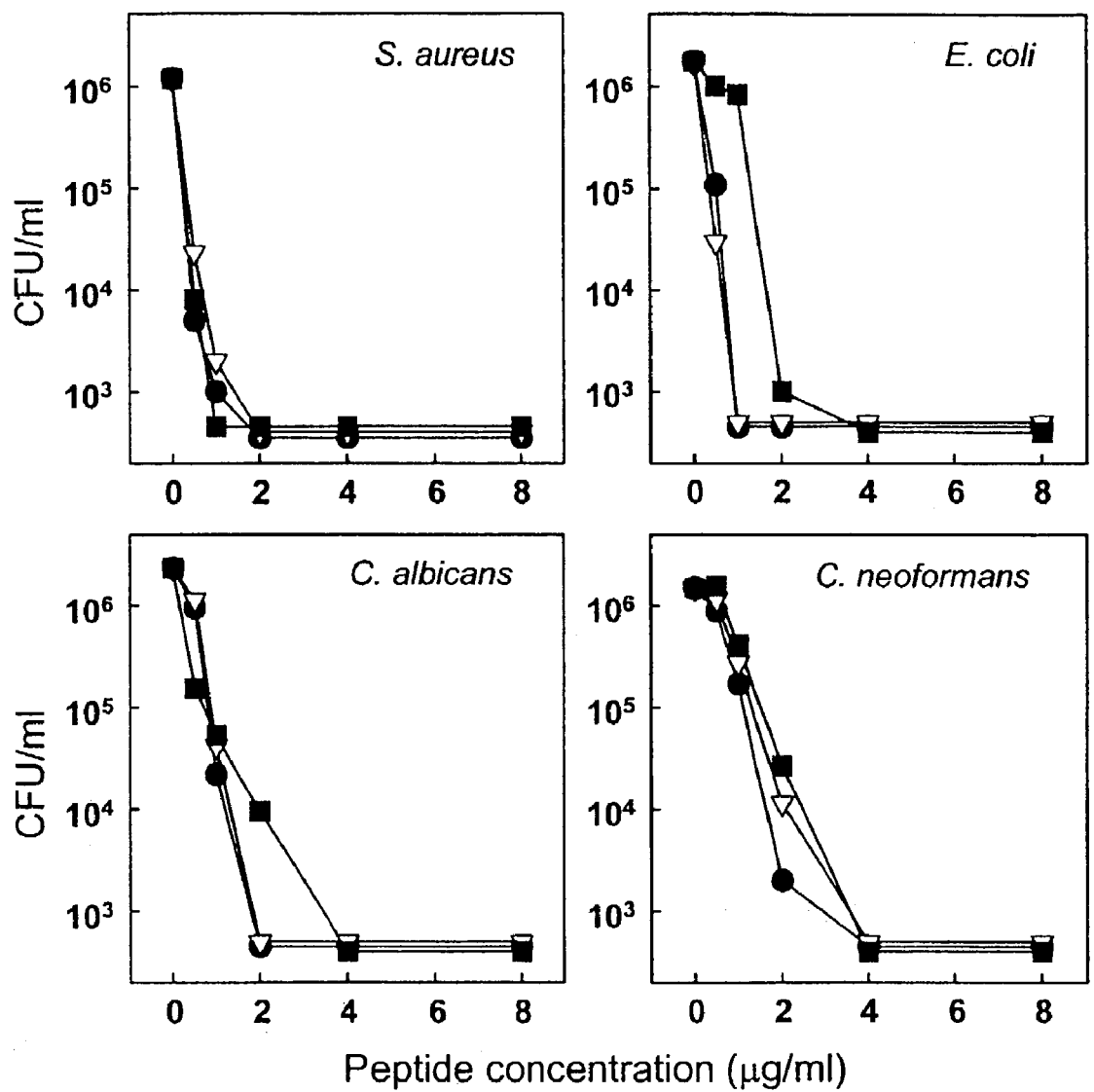
FIG. 4 shows microbicidal activities of RTD-1, 2, and 3. Each organism was incubated with increasing concentrations of RTD-1 (●), RTD-2 (∇), or RTD-3 (■) in 10 mM PIPES, pH 7.4, containing 5 mM glucose for 2 hours at 37° C. The limit of detection (1 colony per plate) was equal to $1\times10^3$ CFU/ml in the incubation mixture.

To determine the microbicidal potencies of RTD-1, 2, and 3, dose-dependent killing experiments were performed as described above. The bactericidal activities of all three peptides were nearly equivalent, and their fungicidal potencies were very similar. However, compared to bacterial killing, approximately twice as much peptide was required to kill the same number of fungal cells (FIG. 4).

Although RTD-3-mediated killing of *E. coli* showed a steep dose dependence similar to that of RTD-1 and 2, approximately twice as much of the peptide was required to achieve the microbicidal effect of RTD-1 and 2. However, at concentrations of 2 µg/ml or higher, all three θ-defensins reduced the viability of *E. coli* ML35 by at least 99.9%. Binding experiments disclosed that equal amounts of each θ-defensin bound to a fixed number of *E. coli* cells, indicating that the differing microbicidal potencies of RTD 1–3 are not a function of differential binding of peptides to the bacterial target.

The potency of RTD-1 was also compared to that of other potent antibacterial peptides. Microbicidal assays were performed in parallel with indolicidin and mouse enteric α-defensins (cryptdins) 3 and 4. On a molar basis, RTD-1, 2, and 3 were each 2- to 4-fold more potent than indolicidin against *S. aureus* 502a. Each of the θ-defensins was equipotent to the cryptdins against *S. aureus*.

A mixture (29:2:1) of synthetic RTD-1, -2 and -3 was prepared and used in microbicidal assays against the four test organisms. The peptide mixture exhibited nearly identical microbicidal potencies as RTD-1, indicating that synergistic microbicidal interactions do not occur under these assay conditions.

The relative yields of RTD-1, 2 and 3 obtained from leukocyte extracts indicated that RTD-1 is ten-fold more abundant than RTD-2 and -3 combined. This indicates a preference for production of RTD-1 by heterodimeric splicing of the RTD-1 precursors, RTD1a and RTD1b.

Despite differences in cationicity, RTD-1 (+5), RTD-2 (+4), and RTD-3 (+6) possess similar antimicrobial potencies against the four organisms tested, and the activities of the three peptides were nearly identical against *S. aureus*, *C. albicans* and *C. neoformans*. RTD-3 was slightly less active against *E. coli* than RTD-1 and RTD-2. This was in contrast to the previous observation that increased cationicity typically correlates with enhanced microbicidal potency and spectrum of activity (Hwang and Vogel, *Biochem. Cell Biol.* 76:235–246 (1998); Matsuzaki, *Biochim. Biophys. Acta* 1462:1–10 (1999)). However, RTD-3 activity against *E. coli* was nearly equivalent to that of RTD-1 and -2 when longer incubation times (4 or 6 h) were used. This suggests that binding of the three peptides to bacterial cells follow different kinetics under these assay conditions.

The binding of peptide to *E. coli* ML35 was equivalent for all three θ-defensins, indicating that the difference in bactericidal activities of RTD-1, 2 and 3 is due to subsequent interactions of peptides with bacterial cells. It is possible that the increased electrostatic interaction of the more cationic RTD-3 with components of the Gram-negative cell envelope adversely affects bactericidal activity. Given that the bacterial cell envelope is probably the target for microbicidal activity, increased affinity of RTD-3 for the bacterial cell envelope can attenuate the peptide's mobility and its ability to transition from the outer cell wall to the inner cytoplasmic membrane (Falla et al., *J. Biol. Chem.* 271:19298–19303 (1996)) or from its monomeric state to a muitimeric pore (Wimley et al., *Protein Science* 3:1362–1373 (1994)).

These results demonstrate that RTD-1, 2 and 3 exhibit antimicrobial activity against bacteria and fungi.

EXAMPLE II

Structure-Activity Relationships of Rhesus
θ-Defensins and Pig Neutrophil Protegrin PG-1

This examples describes the comparison of activities of Rhesus θ-defensins with protegrin.

For peptide synthesis, disulfide formation and peptide cyclization of protegrin, PG-1 and analogs were synthesized using protocols described for syntheses of RTD-1, RTD-2 and RTD-3 (see Example I, and Tang et al., supra, 1999). Briefly, linear sequences of peptide acids (see FIG. 5) were assembled on Fmoc-Arg(Pbf)-PEG-PS support (PerSeptive Biosystem, CA), and peptide amides were assembled on a Fmoc-PAL (peptide amide linker)-PEG-PS support. Each peptide was assembled at 0.1-mmol scale on a 9050 Peptide Synthesizer (PerSeptive Biosystem, CA). All amino acids except cysteine were coupled with in situ HATU/DIEA activation. Cysteine residues were coupled using the preformed pentafluorophenyl ester derivative. Several analogs were assembled simultaneously with double coupling at every residue. Peptides were cleaved and deprotected after 4 h treatment in reagent R (van Abel et al., *International J. Peptide Protein Res.* 45:401–409 (1995). (RTD-3 analogs) or reagent K (van Abel et al., supra, 1995) (PG-1 and analogs) (see Example I). Crude synthetic products were obtained with acetic acid/dichloromethane extraction followed by lyophylization of the aqueous phase (Tang et al., supra, 1999).

Linear versions of the peptides were purified by RP-HPLC and characterized by MALDI-TOF MS. Disulfide bonds were formed by air oxidation in 17.4 mM ammonium acetate, pH 7.5–8.0, similar to those for θ-defensins (see Example I and Tang et al., supra, 1999). Folding was monitored by analytical HPLC and mass spectroscopy. Peptide cyclization was performed in 0.1% DIPEA in DMSO with 60 and 20 molar equivalents of EDC and HOBt, respectively. The cyclic analogs cPG-1 and 3cys cPG-1 were prepared by cyclization of 4:4 PG-1-OH and 3cys 2:2 PG-1-OH, respectively. The extent of peptide cyclization was monitored by RP-HPLC followed by mass spectroscopy. Peptides were purified by preparative RP-HPLC and characterized by AU-PAGE, analytical RP-HPLC, amino acid analysis and MALDI-TOF MS. Peptide concentrations were determined by amino acid analysis.

To test microbicidal activities, the activities of each peptide against *S. aureus* 502a, *E. coli* ML35, and *C. albicans* 16820 were assessed essentially as described in Example I with modifications to allow for simultaneous analysis of all twenty peptides. Briefly, two-fold serial dilutions of each peptide (in 0.01% acetic acid 0.062–8.0 μg/ml final concentrations) were mixed with 10 mM PIPES, pH 7.4, containing 5 mM glucose in sterile polystyrene 96-well plates (Corning, N.Y.). Aliquots of log-phase bacteria or yeast were added to a $2\times10^6$ CFU/ml final density as determined by A620. After 2 h incubation at 37° C., 15 μl of the incubation mixture was removed and serially diluted ten-fold from 1:10 to $1:10^6$ in trypticase soy broth (bacteria) or Sabaraud dextrose broth (*C. albicans*). The diluted cell suspensions were grown 24–48 h at 37° C. until cell pellets were visible. Microbicidal activity was determined as absence of growth and was correlated to CFU/ml in control experiments where activity was determined in parallel by colony counting (see Example I). Absence of growth at the $1:10^3$ dilution is equivalent to a 3-log reduction in microbial viability. Minimum microbicidal concentration (MMC) was determined for each peptide as the lowest concentration that reduced cell viability by 99.9%.

To determine the effects of serum, salt, calcium chloride and magnesium chloride on microbicidal activities, peptide activities were determined in assays containing varying ionic strength, divalent cations, and serum. The effect of serum on staphylocidal activity of each peptide was determined by incubating $1\times10^6$ CFU/ml of *S. aureus* 502a with increasing peptide concentrations (0.5–4 μg/ml) in 10 mM PIPES, pH 7.4, containing 10% normal human serum for 2 h at 37° C. The effect of sodium chloride on staphylocidal activities was assessed with 5 μg/ml of each peptide in 10 mM PIPES, pH 7.4, containing varying concentrations of sodium chloride (0–160 mM). Effects of divalent cations, $CaCl_2$, or $MgCl_2$ (0–5.6 mM) were assessed in microbicidal assays against *E. coli* ML35. Bactericidal activities were determined by colony counting (see Example II), and microbicidal potencies were expressed as percent killing as follows:

$$\% \text{ killing} = \left[\frac{A_0 - A}{A_0}\right] \times 100\%$$

where A=surviving bacteria (CFU/ml) after initial incubation with each peptide in buffer containing serum, salt, or divalent cations and $A_o$=bacterial CFU/ml in the "no-peptide" controls.

Linear peptides produced by Fmoc solid phase methodology were purified by preparative reversed-phase HPLC and air oxidized to form the disulfide bonds, as described above. The folding reactions were monitored by RP-HPLC followed by MALDI-TOF MS. Folding and oxidation efficiency was between 50 and 60% for each peptide. The molecular masses of peptides with three disulfides (peptides 1–9 and 16–20, FIG. 5A) were 6 a.m.u. less than those of the linear molecules, consistent with formation of three disulfide bonds (FIG. 5A). Similarly, the molecular masses of fully oxidized peptides with two disulfide bonds (peptides 10–15) were 4 a.m.u. less than those of the linear product.

Cyclic analogs of protegrin, cPG-1 and 3cys cPG-1, were obtained by EDC/HOBt cyclization of the purified acyclic 4:4 PG-1 acid and 3cys 2:2 PG-1 acid, respectively. The extent of peptide cyclization was evaluated by RP-HPLC and MALDI-TOF MS. Efficiency of peptide cyclization for the two cyclized protegrin analogs was 30–50% as determined by quantitative RP-HPLC. On average, 5–6 mg of each peptide was obtained with greater than 99% purity, corresponding to 40–50% yield relative to the linear peptides obtained following cleavage and deprotection.

Purified peptides were characterized by analytical RP-HPLC, amino acid analysis, MALDI-TOF MS, and AU-PAGE. The amino acid compositions determined by amino acid analysis were consistent with those determined from the primary sequences. The molecular masses matched those predicted by the amino acid sequences of the peptides listed in FIG. 5A. RP-HPLC purified peptides were analyzed by AU-PAGE. The electrophoretic mobilities of the peptides correlated with their relative charge/mass ratios.

θ-defensins and protegrins share a number of structural features, including amino acid chain length, the occurrence of multiple disulfides, net cationicity, and overall peptide fold (Tang et al., supra, 1999). To determine the relative microbicidal activities of these two peptide families and specific structural features required for these activities, a series of analogs was synthesized to evaluate the functional contribution(s) of particular moieties. Specifically, analogs of θ-defensins were produced that were acyclic (that is, de-cyclized). The acyclic analogs, now resembling protegrins, were synthesized with either a carboxyl terminal acid or amide to assess the importance of this moiety (FIG. 5A, analogs 1–8). Since protegrins possess uneven (or overlapping) chain termini (FIG. 5A), two θ-defensin analogs were produced in which the chain termini were overlapping (FIG. 5A, analogs 9 and 10) to test the hypothesis that this feature might confer properties of protegrins upon θ-defensins. In addition, the differing disulfide content of analogs 9 (3 disulfides) and 10 (2 disulfides) allowed for the functional comparison of peptides with differing degrees of backbone constraint. As discussed below, these two peptides are among those that can be considered θ-defensin-protegrin hybrids.

The functional role of the overlapping chain termini in protegrins was addressed by producing C-terminal acid and amidated analogs of protegrin-1 in which the chain termini were even (that is, non overlapping; FIG. 5A, analogs 11, 12, 14, and 15). These analogs are most similar to the acyclic θ-defensin analogs. The role of cyclization per se was analyzed by producing cyclic θ-defensin-protegrin hybrids, namely cPG-1 (2 disulfides) and 3cys cPG-1 (3 disulfides). The functional significance of the three-disulfide motif (θ-defensins) versus the two-disulfide motif (protegrins) was further investigated by generating protegrin analogs 16–20 (FIG. 5A), in which the protegrin backbone was modified by adding an additional disulfide bond, while retaining net charge. Moreover, characterization of this group of peptides enabled an analysis of the contributions of cyclization, status of the carboxyl termini, and overlapping chain termini.

Additional theta defensin analogs were synthesized (FIG. 5B). All peptides were synthesized using protocols established for the synthesis of RTD-1, as described above. Linear peptides were oxidized to form the disulfide bonds (boxed Cys residues) and cyclized (loops). Each peptide was purified to homogeneity. The molecular masses of the linear peptides were calculated using the PeptideMass module of the Expert Protein Analysis System (ExPASy) (Wilkins et al., *Protein Identification and Analysis Tools in the ExPASy Server in: 2D Proteome Analysis Protocols,* Link, ed., Humana Press, New Jersey (1998)). The molecular masses for folded peptides were determined by subtracting the masses of protons eliminated upon formation of disulfide bonds; for cyclic peptides, the masses resulted from loss of 18 amu (water) upon peptide cyclization. The not applicable designation of "N/A" for peptide 24 for the folded form is because peptide 24 does not contain a disulfide.

Figure 5C:
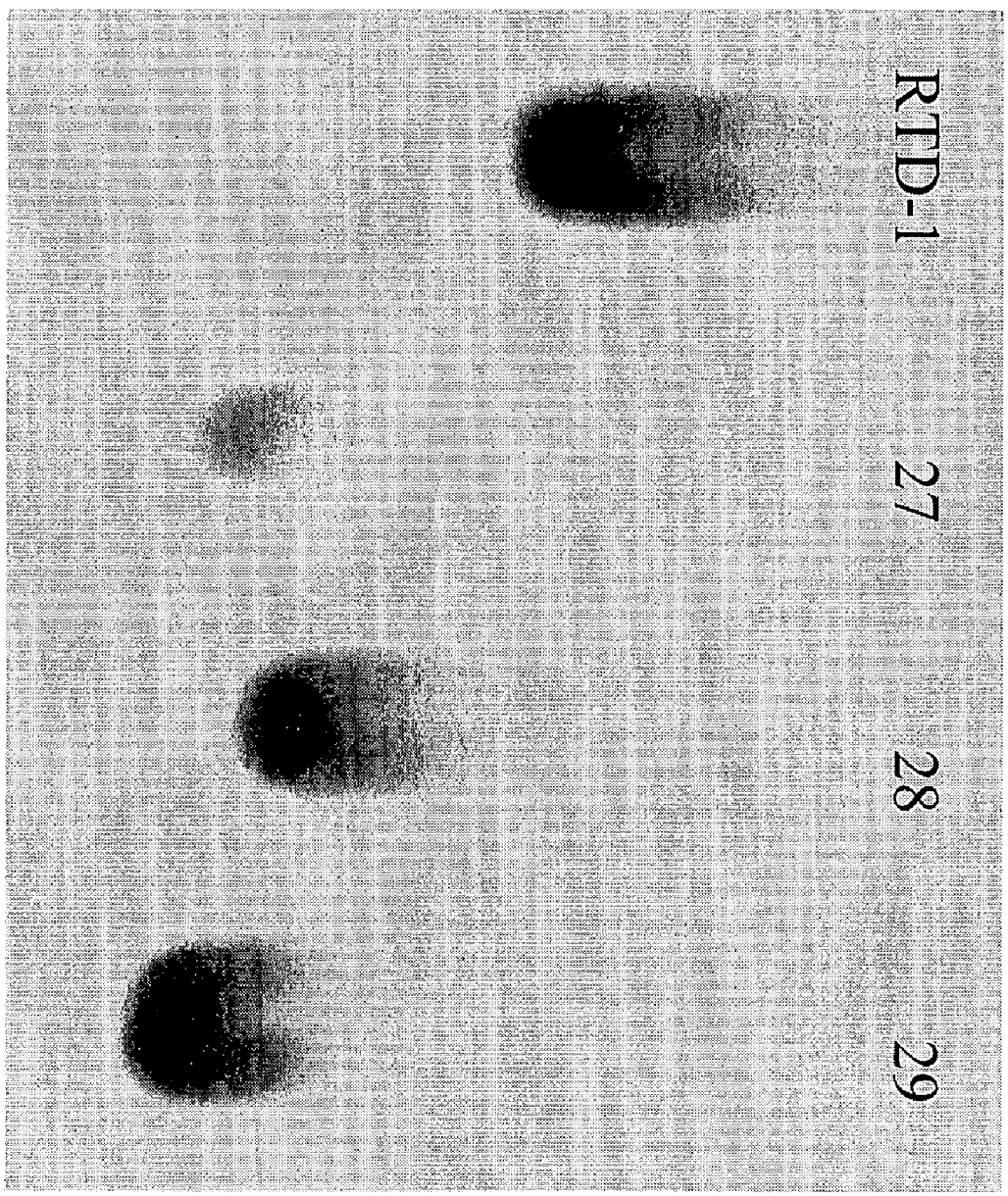
FIG. 5C shows acid-urea polyacrylamide gel electrophoresis (PAGE) analysis of theta defensin analogs. Lane 1 contains an aliquot of RTD-1, and lanes 2–4 contain aliquots of theta defensin analogs designated 27–29, respectively.

FIG. 5C shows acid-urea polyacrylamide gel electrophoresis (PAGE) analysis of theta defensin analogs. Aliquots containing 1–5 μg of each of the micro-θ-denfensins designated peptides 27–29 (see FIG. 5B) were compared with RTD-1. The molecular weights of RTD-1 and peptides 27–29 are 2182.6, 1652.0, 1720.2 and 1630.1, respectively. The peptides were visualized by silver staining.

The activities of antimicrobial peptides are typically evaluated in an agar diffusion assay and a cell-suspension microbicidal assay (see Example I). The combined microbicidal and microbiostatic activities are measured in the diffusion assay, but only the microbicidal activity is determined in the cell-suspension format. The conditions of the cell-suspension microbicidal assay can be modified with various modulators to test their effects on peptides activities, and the assay can also be adapted to evaluate the peptide permeabilization of bacterial cell envelope (see Example III). Therefore, a modified version of the microbicidal assay was used to determine the minimum microbicidal concentrations of all twenty peptides against three test organisms, as described above. The relative microbicidal activities of the various analogs were also evaluated in assays containing various concentrations of salt, divalent cations, and serum.

The microbicidal activities of some of the θ-defensin and PG-1 analogs were analyzed by determining the minimum microbicidal concentrations (MMC) for all twenty peptides against *S. aureus* 502a, *E. coli* ML35, and *C. albicans* 16820. Peptide activities were first analyzed against the three test organisms in 10 mM PIPES, 5 mM glucose, pH 7.4. As summarized in Table 2, the MMC for 17 of the 20 peptides ranged from 0.3 to 5 μg/ml. Three peptides (aRTD-1-OH; aRTD-2-OH; 3:1 aRTD-3-NH) did not achieve a 99.9% kill against one of the bacterial organisms at 8 μg/ml, the highest concentration tested. RTD-1,2 and 3 (also see Example I) and PG-1 were microbicidal at low micromolar concentrations (0.2–1.1 μM) against all three test organisms.

TABLE 2

| | MMC (μg/ml) | | |
|---|---|---|---|
| | S.aureus | E. coli | C. albicans |
| 1. aRTD-1-NH[a] | 5.0 | 2.0 | 1.0 |
| 2. RTD-1* | 1.0 | 2.0 | 1.0 |
| 3. aRTD-1-OH | 4.5 | (99%)[b] | 4.0 |
| 4. RTD-2* | 1.5 | 2.3 | 3.0 |
| 5. aRTD-2-OH | 1.5 | (90%)[b] | 3.0 |
| 6. RTD-3* | 1.0 | 2.0 | 1.0 |
| 7. aRTD-3-OH | 1.5 | 4.0 | 1.5 |
| 8. aRTD-3-NH | 4.5 | 1.0 | 0.8 |
| 9. 3:1 aRTD-3-NH | (99%)[b] | 1.0 | 0.8 |
| 10. 5:3 aRTD-3-NH | 1.0 | 3.0 | 2.3 |
| 11. PG-1* | 0.4 | 1.0 | 0.8 |
| 12. PG-1-OH | 2.0 | 1.5 | 1.5 |
| 13. cPG-1 | 2.0 | 1.0 | 2.5 |
| 14. 4:4 PG-1-OH | 1.0 | 1.0 | 2.5 |
| 15. 4:4 PG-1-NH | 0.5 | 1.0 | 1.5 |
| 16. 3cys cPG-1 | 0.5 | 1.3 | 2.5 |
| 17. 3cys 2:2 PG-1-OH | 2.0 | 1.0 | 4.0 |
| 18. 3cys 2:2 PG-1-NH | 0.3 | 1.0 | 1.5 |
| 19. 3cys 3:1 PG-1-OH | 0.5 | 1.5 | 1.5 |
| 20. 3cys 3:1 PG-1-NH | 2.0 | 1.5 | 4.0 |

Figure 6:
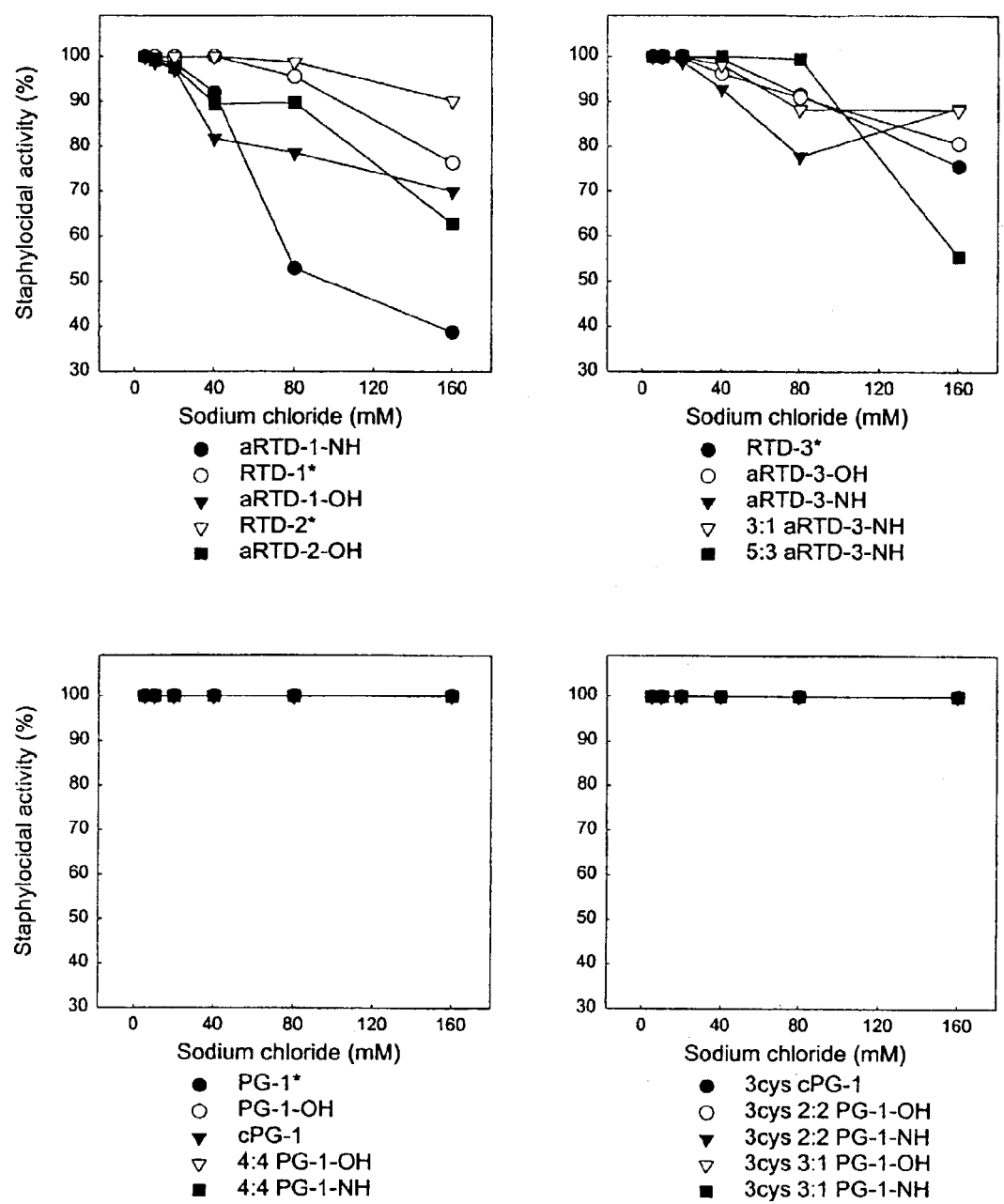
FIG. 6 shows the effect of sodium chloride on staphylocidal activities of θ-defensins, PG-1, and analogs. The activity of each peptide (5 μg/ml) was determined in assays containing increasing concentrations of sodium chloride. Staphylocidal activities were expressed as percentages of killing obtained in the absence of additional NaCl.
Figure 7:
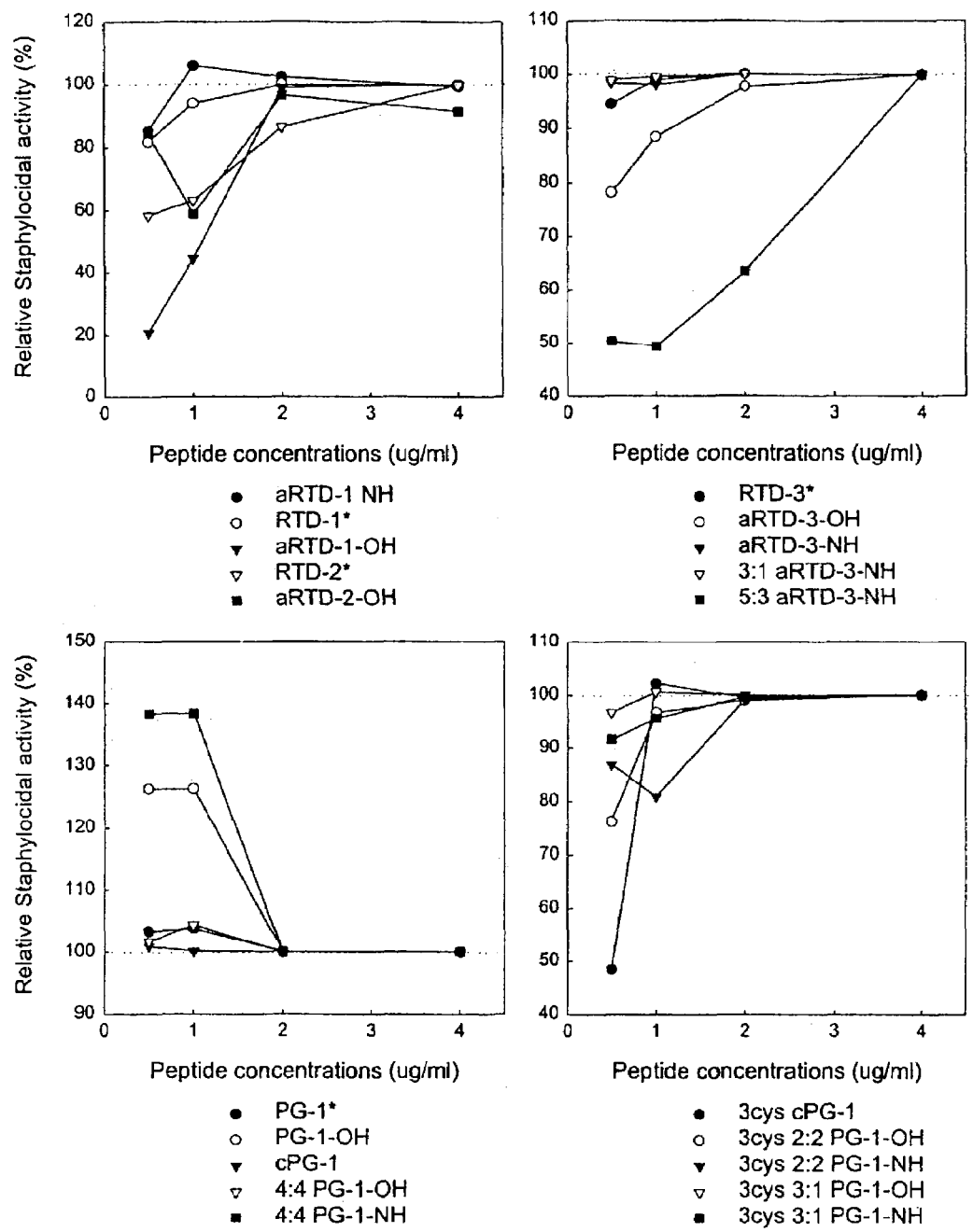
FIG. 7 shows the effect of serum on killing of S. aureus 502a by θ-defensins, PG-1, and analogs. Dose-dependent staphylocidal activity of each peptide was determined in assays containing 10% normal human serum. Percentages of killing are relative to activities of peptide-containing incubations in which serum was omitted.

[a]see FIG. 5 for peptide identities
[b]the 99.9% microbial killing defined for MMC was not reached. Killing percentages at 8 μg/ml, the highest concentration tested, are shown
*native sequences Modified assays were used to evaluate the bactericidal activities of the 20 peptides in physiologic concentrations of salt (145 mM NaCl), divalent cations (1–2 mM $CaCl_2$ and $MgCl_2$), and in 10% normal human serum. Under these conditions, the bactericidal activities of all three θ-defensins and PG-1 persisted (≧80% killing; FIGS. 6 and 7, and Table 3). The activities of θ-defensin analogs were inhibited to varying degrees by the incubation additives, whereas the activities of protegrin analogs were not affected (see below). The microbicidal activities of the twenty peptides are described below in the context of specific structure-activity studies, that is, peptide cyclization, C-terminal amidation, two- and three-disulfide motifs, and differing lengths of the chain termini.

TABLE 3

| | | % killing in divalent cations | | | |
|---|---|---|---|---|---|
| | | $CaCl_2$ (mM) | $MgCl_2$ (mM) | | |
| | | 1.4 | 1.4 | 2.8 | 5.6 |
| 1. | aRTD-1-NH[a] | 98 | 100 | 100 | 100 |
| 2. | RTD-1* | 99 | 100 | 100 | 97 |
| 3. | aRTD-1-OH | 20 | 100 | 100 | 74 |
| 4. | RTD-2* | 83 | 100 | 98 | 96 |
| 5. | aRTD-2-OH | 0 | 92 | 74 | 3 |
| 6. | RTD-3* | 99 | 100 | 100 | 100 |
| 7. | aRTD-3-OH | 70 | 100 | 100 | 0 |
| 8. | aRTD-3-NH | 93 | 100 | 100 | 96 |
| 9. | 3:1 aRTD-3-NH | 78 | 100 | 100 | 97 |
| 10. | 5:3 aRTD-3-NH | 0 | 77 | 0 | 0 |
| 11. | PG-1* | 100 | 100 | 100 | 100 |
| 12. | PG-1-OH | 100 | 100 | 100 | 100 |

TABLE 3-continued

% killing in divalent cations

| | | CaCl$_2$ (mM) | MgCl$_2$ (mM) | | |
|---|---|---|---|---|---|
| | | 1.4 | 1.4 | 2.8 | 5.6 |
| 13. | cPG-1 | 100 | 100 | 100 | 100 |
| 14. | 4:4 PG-1-OH | 100 | 100 | 100 | 100 |
| 15. | 4:4 PG-1-NH | 100 | 100 | 100 | 100 |
| 16. | 3cys cPG-1 | 100 | 100 | 100 | 100 |
| 17. | 3cys 2:2 PG-1-OH | 97 | 100 | 100 | 100 |
| 18. | 3cys 2:2 PG-1-NH | 93 | 100 | 100 | 100 |
| 19. | 3cys 3:1 PG-1-OH | 100 | 100 | 100 | 100 |
| 20. | 3cys 3:1 PG-1-NH | 100 | 100 | 100 | 100 |

$^a$see Fig. 5 for peptide identities
*native sequences

De-cyclization of θ-defensins reduces peptide microbicidal activities. The microbicidal activities of RTD 1, 2 and 3 and the de-cyclized (acyclic) analogs, aRTD-1-OH, aRTD-2-OH and aRTD-3-OH (peptide 3, 5, and 7) were analyzed to determine the effect of peptide cyclization on antimicrobial function (Table 2). The MMC values of aRTD-1-OH against all three test organisms were 4-fold higher than those of the native cyclic peptide. The minimum microbicidal concentrations of RTD-3 were increased by 1–2 fold after decyclization of the peptide backbone (aRTD-3-OH). Interestingly, the staphylocidal and candidacidal activities of aRTD-2-OH were equivalent to those of the native cyclic peptide, while the peptide potency against E. coli was reduced by at least 3-fold. These results indicate that the microbicidal potencies and spectra of θ-defensin activities are decreased by de-cyclization of the peptides.

In assays containing increasing concentrations of sodium chloride (up to 160 mM), killing of S. aureus by RTD 1, 2 and 3 was reduced by 10–20% in 80–160 mM salt concentrations. The acyclic peptides (aRTD-1–3-OH) were 20–40% inhibited in salt concentrations as low as 40 mM (FIG. 6). Analysis of relative microbicidal activities in physiologic salt and peptide net charges demonstrated that aRTD-2-OH (+4) was most inhibited, while aRTD-3-OH (+6) was least affected, and the inhibition of aRTD-1-OH (+5) activity was intermediate, suggesting that the extent of salt inhibition on microbicidal function of acyclic θ-defensins increases with decreasing peptide net charge.

The bactericidal activities of cyclic θ-defensins were generally unaffected in assays containing various concentrations of CaCl$_2$ (1.4 mM) or MgCl$_2$ (up to 5.6 mM), but the microbicidal activities of all three de-cyclized θ-defensin analogs were significantly attenuated in presence of the divalent salts (Table 3). In a physiologic concentration of calcium chloride, the bactericidal activity of aRTD-2-OH was completely ablated, aRTD-1-OH was 80% inhibited, and the activity of aRTD-3-OH was 30% attenuated. Calcium inhibition increased with decreasing peptide net charge, similar to that observed in salt-inhibition experiments.

θ-defensins and the acyclic analogs demonstrated dose-dependent killing of staphylococci in assays containing 10% NHS. At 2–4 µg/ml concentrations, the peptide activities were equivalent to those in buffer (FIG. 7). However, at the lower concentrations (0.5–1 µg/ml), the activities of the acyclic analogs were reduced by as much as 80%. Moreover, the acyclic peptides were generally more inhibited by serum than the native cyclic peptides. At low peptide concentrations, aRTD-1-OH was inhibited by 60–80%, while cyclic RTD-1 was inhibited at less than 20%. The activity of aRTD-3-OH was 10–20% inhibited, while RTD-3 showed less than 5% difference in activity compared to that in absence of serum. Activities of RTD-2 and the acyclic aRTD-2 analog were similarly attenuated by 20–40%, suggesting that peptide net charge can also contribute to the serum resistance of θ-defensins and that peptide cyclization enhanced microbicidal function in serum.

In incubations lacking ionic or serum additives, the relative MMC's of θ-defensins and the de-cyclized analogs suggested that peptide cyclization endows θ-defensins with optimal microbicidal potencies and spectrum of activity. The peptide activities in assays containing various physiologic modulators indicated that de-cyclization of θ-defensins renders the acyclic analogs sensitive to salt, divalent cations and serum. The inhibitory effects of salt, divalent cations and serum on bactericidal activities of acyclic θ-defensin analogs increased with decreasing peptide net charge. However, an association between peptide net charge and activity inhibition was not observed with the cyclic (native) θ-defensins.

Amidation of acyclic θ-defensins reduces the peptide spectrum of activities. The acyclic aRTD-1 and aRTD-3 were synthesized with carboxyl terminal acid (aRTD-1-OH and aRTD-3-OH) or amide (aRTD-1-NH and aRTD-3-NH) to evaluate the contribution of the C-terminal amide to microbicidal activity. Carboxamidation of decyclized aRTD-1 had no effect on peptide staphylocidal potency relative to that of the peptide acid, but potency against E. coli and C. albicans was enhanced by 4-fold (Table 2). Similarly, the activities of aRTD-3-NH were 2- to 4-fold higher than those of aRTD-3-OH against E. coli and C. albicans, but the staphylocidal potency was reduced by 3-fold. In nearly all cases, the carboxamide analogs were also less active than the cyclic θ-defensins. Thus, C-terminal amidation of acyclic θ-defensins enhances the peptide activities against E. coli and C. albicans relative to those of the peptide acid analogs, but the carboxamide group decreased the peptide potencies against S. aureus.

In assays containing sodium chloride, the carboxamidated θ-defensin analogs (aRTD-1-NH and aRTD-3-NH) were inhibited by as much as 40%, while the C-terminal acid peptides (aRTD-1-OH and aRTD-3-OH) were inhibited by 30% or less (FIG. 6). However, the activities of carboxamidated peptides were insensitive to the effects of divalent cations, while those of the peptide acid equivalents showed marked sensitivity (discussed above) (Table 3). Staphylocidal activities of all four θ-defensin analogs were unaffected in assay containing serum (FIG. 7). De-cyclization of θ-defensins had a profound effect on the peptide microbicidal potency, spectrum of activity and resistance to various physiologic modulators. Amidation of the C-terminus partially compensated for de-cyclization.

De-amidation of protegrin reduces the peptide microbicidal activities. As described above, peptide cyclization and amidation had profound effects on the microbicidal functions of θ-detensins. The structure-activity relationships of the carboxamide group in protegrins was evaluated. The analog PG-1-OH (peptide 12) was synthesized to determine whether the C-terminal moiety contributed to microbicidal activities of protegrin, a natural peptide amide (peptide 11). Staphylocidal potency of the acid analog was 5-fold less than that of the native peptide, and the microbicidal potencies of the analog against E. coli and C. albicans were attenuated 1- to 2-fold (Table 2). These results indicate that the carboxamide group is essential for optimal microbicidal potencies of protegrin against all three organisms.

Bactericidal activities of protegrin and the acid analog were unaffected in assays containing various concentrations of salt and divalent cations (FIG. 6 and Table 3). The staphylocidal activity of PG-1-OH appeared enhanced by 25% in assay containing 10% normal human serum, while that of the native PG-1 was unaffected (FIG. 7). The equivalent activities of PG-1 with or without the C-terminal amide group indicated that the carboxamide group is not likely be necessary for salt- and serum-resistance in protegrin.

Cyclization of protegrin reduces peptide microbicidal potencies. The effect of peptide cyclization on activities of protegrin was analyzed by comparing the native peptide and the cyclic cPG-1 (two disulfides) and 3cys cPG-1 (three disulfides) analogs. The minimum staphylocidal concentration of cPG-1 was 5-fold more than that of the native PG-1, while the MMC values for both peptides against E. coli were identical. Candidacidal potencies of cPG-1 and 3cys cPG-1 were attenuated by 3-fold (Table 2). Compared to PG-1, the microbicidal activities of the cyclized θ-defensin-protegrin hybrid cPG-1 were reduced by the same degree as the de-amidated analog of PG-1. Interestingly, the minimum microbicidal activities of the 3cys cPG-1 against E. coli and S. aureus were nearly equivalent to those of native PG-1, indicating that the incorporation of a tridisulfide motif and peptide cyclization confer microbicidal properties of θ-defensins upon PG-1. The activities of cPG-1 and 3cys cPG-1 analogs persisted in assays containing varying concentrations of salt (FIG. 6), divalent cations (Table 3), and 10% NHS (FIG. 7), indicating that neither peptide cyclization nor the increased disulfide content mitigate the protegrin resistance to the physiologic modulators. Thus, the combined tridisulfide motif and peptide cyclization (but not cyclization alone) appeared to compensate for the reduction in bactericidal potencies by "de-amidation" of PG-1.

The three-disulfide motif is important for optimal microbicidal activities of θ-defensin-protegrin hybrids. The contribution of increasing backbone constraint on the microbicidal activity of protegrin-1 was further addressed by producing tridisulfide θ-defensin-protegrin hybrids (peptides 16–20). The additional cysteine pair was incorporated into the tridisulfide PG-1 analogs by the Arg4 to Cys4 and Gly17 to Cys17 substitutions. The peptide arginine content of PG-1 was maintained with a Leu5 to Arg5 substitution. All of the tridisulfide PG-1 analogs (peptides 16–20) were resistant to physiologic salt, various concentrations of divalent cations, and 10% serum, indicating that the increase in disulfide content did not adversely affect the peptide activities in these physiologic modulators.

Incorporation of the tridisulfide motif resulted in reduced antimicrobial activities of 3cys 3:1 PG-1-NH (peptide 20) relative to those of native PG-1. The 3cys 3:1 PG-1-NH analog was 5-fold less active than PG-1 against S. aureus and C. albicans while the bactericidal activity against E. coli was not significantly reduced (Table 2). Surprisingly, the activities of the 3cys 3:1 PG-1-OH analog were nearly equivalent to those of PG-1 against all three organisms, indicating that the removal of the carboxamide group enhanced microbicidal activities of the tridisulfide θ-defensin-protegrin hybrid.

The effects of the two- and three-disulfide motifs on activities of θ-defensins were also evaluated with protegrin-RTD-3 hybrids 3:1 aRTD-3-NH and 5:3 aRTD-3-NH (peptides 9 and 10). Both peptides were produced with a C-terminal amide and overlapping chain termini to resemble the structure of protegrins. Staphylocidal activity of the three-disulfide 3:1 aRTD-3-NH was at least 8-fold less than those of RTD-3 and PG-1 (Table 2). However, the minimum staphylocidal concentration of the two-disulfide 5:3 aRTD-3-NH was equivalent to RTD-3, suggesting that decreasing disulfide constraint increased staphylocidal activity of protegrin-RTD-3 hybrids. The microbicidal activities of 3:1 aRTD-3-NH against E. coli and C. albicans were nearly equivalent to those of RTD-3 and PG-1, while the activities of 5:3 aRTD-3-NH against these two organisms were 2–3 fold less. These results suggested that the tridisulfide motif is important for killing of E. coli and C. albicans.

Unlike the θ-defensin-PG-1 hybrids (peptides 13, 16–20), whose activities were unaffected by physiologic modulators, bactericidal activities of protegrin-RTD-3 hybrids (peptides 9 and 10) were inhibited by 20–40% in salt and 20–50% in serum (FIGS. 6 and 7). Under both assay conditions, the two-disulfide 5:3 aRTD-3-NH (analog 10) was more inhibited than was the three-disulfide 3:1 aRTD-3-NH (analog 9). The bactericidal activity of the two-disulfide hybrid was also completely inhibited in assays containing various concentrations of divalent salts, whereas the activity of the three-disulfide hybrid was not significantly affected (Table 3). These results indicate that the tridisulfide motif contributed to the microbicidal function of θ-defensins in all assays containing ionic or serum additives.

Taken together, the additional backbone constraint conferred by the tridisulfide motif resulted in reduced activities of θ-defensin-PG-1 hybrids compared to native two-disulfide protegrin-1. However, this structural feature appeared to compensate for the reduction in potencies associated with the removal of the carboxamide group of protegrin. Moreover, the three-disulfide structure did not diminish the protegrin resistance to various physiological modulators. In contrast, the three-disulfide motif appeared necessary for salt- and serum resistance of the RTD-3-protegrin hybrids (analogs 9 and 10), indicating that this structural feature is essential for the optimal microbicidal functions of θ-defensins.

Microbicidal activities of θ-defensin-protegrin hybrids are generally unaffected by varying the lengths of chain termini. Since protegrins possess overlapping chain termini (FIG. 5), the contribution of this structural feature to the microbicidal functions of PG-1 and θ-defensin analogs was determined. The θ-defensin analogs 3:1 aRTD-3-NH and 5:3 aRTD 3-NH were produced with overlapping chain termini for comparison with the even-termini aRTD-3-NH. Activities of θ-defensin analogs bearing overlapping and even chain termini were discussed in context with de-cyclization, amidation, and production of θ-defensin-protegrin hybrids on RTD-3 sequence (see above). Briefly, the microbicidal activities of aRTD-3-NH and 3:1 aRTD-3-NH (analog 8 and 9) were nearly identical (Table 2), and the activities of both peptides persisted in various physiologic modulators. This indicates that the varying lengths of the chain termini are not essential for the microbicidal function of the de-cyclized θ-defensins (FIGS. 6 and 7 and Table 3). The enhanced staphylocidal potency of the two-disulfide 5:3 aRTD-3-NH hybrid relative to those of the carboxamidated aRTD-3 analogs (peptides 8 and 9) was due to the removal of a disulfide bond. However, the 5:3 aRTD-3-NH hybrid was completely inhibited in various concentrations of divalent cations.

Analogs of protegrins (peptides 14 and 1) were synthesized with even chain termini to analyze the contribution of this structural feature to microbicidal functions. The minimum bactericidal (*S. aureus* and *E. coli*) activities of 4:4 PG-1-NH were equivalent to those of PG-1 (Table 2). The candidacidal activity of 4:4 PG-1-NH analog was slightly less than that of the native peptide. The activities of the even-termini 4:4 PG-1-OH analog were also comparable to those of the overlapping-termini PG-1-OH (peptide 12), indicating that the varying lengths of chain termini had little or no contribution toward the microbicidal functions of protegrins.

The bactericidal activities of PG-1 (5:3 overlapping-termini, peptide 11) and 4:4 PG-1-NH (even-termini, peptide 15) were not affected in assays containing ionic and serum additives, indicating that the overlapping-termini structure was not essential for the salt- and serum-resistance of protegrin. Interestingly, the staphylocidal activity of 4:4 PG-1-NH was enhanced by nearly 40% in assays containing human serum (FIG. 7). The activity of PG-1-OH (peptide 12) was also enhanced in 10% serum. The results suggest that these two analogs of protegrins interact synergistically with components in serum in the killing of *staphylococci*.

The effect of length of chain termini was also evaluated by determining microbicidal activities of a group of tridisulfide θ-defensin-protegrin hybrids (peptides 17–20). The bactericidal activities of all four analogs against *E. coli* were nearly equivalent. However, the staphylocidal and candidacidal activities of the even-chain termini 3cys 2:2 PG-1-OH (peptide 17) were 2–4 fold less than those of 3cys 3:1 PG-1-OH (peptide 19), indicating that the microbicidal potencies were enhanced by the overlapping-chain termini. Surprisingly, the structure-function relationship was reversed when the same pair of analogs were produced with amidated C-termini (peptide 18 and 20). The microbicidal activities of the even-chain termini 3cys 2:2 PG-1-NH were 2–3 fold (*C. albicans*) and 6–7 fold (*S. aureus*) higher than those of the 3cys 3:1 PG-1-NH. Taken together, these results indicate that the activities of the tridisulfide, acyclic θ-defensin-protegrin hybrids are enhanced by different combinations of the two structural elements: i) C-terminal acid and overlapping-chain termini or ii) carboxamide and even-chain termini.

In summary, the structure-and-microbicidal-activity relationships of θ-defensins and protegrin-1 were evaluated by comparing the microbicidal activities of 20 analogs against 3 organisms and by determining the relative bactericidal activities in assays containing ionic and serum additives. The major findings are as follows: i) de-cyclization of θ-defensins attenuated microbicidal activities against all three test organisms. The activities of acyclic analogs were inhibited by various physiologic modulators, and the extent of inhibition increased with decreasing peptide net charge, ii) amidation of acyclic θ-defensins altered the balance between microbicidal potency and spectrum of activity. In assays containing ionic and serum additives, the carboxamidated θ-defensin analogs were more inhibited than the naturally-occurring cyclic peptides, iii) the three-disulfide structure is important for salt- and serum-resistance of protegrin-RTD-3 hybrids (peptides 9 and 10), iv) de-amidated protegrin was less microbicidal than the natural peptide amide, but this structural feature had little or no effect on the peptide salt- and serum-resistance, v) cyclization of protegrin had the same effect as de-amidation. However, in combination with the increased disulfide constraint, peptide cyclization appeared to compensate for the decrease in microbicidal potencies, vi) varying lengths of chain termini had little contributions to the activities of protegrin and acyclic θ-defensins. However, these structural features, combined with the C-terminal moiety, i.e., carboxamide or peptide acid groups, had opposing effects on the microbicidal functions of the three-disulfide θ-defensin-PG-1 hybrids (peptides 17–20).

Overall, peptides with cyclic backbones or C-terminal amide groups were generally more microbicidal than the peptide acid analogs. The enhanced microbicidal activity correlates with the increase in peptide net charge (carboxamidation) or the removal of the C-terminal acidic moiety (cyclization and amidation). Although the activities of de-cyclized θ-defensin and de-amidated protegrin analogs were attenuated by several fold relative to those of the native molecules, the structural analogs remained microbicidal at low micromolar concentrations.

EXAMPLE III

Membranolytic Activities of Rhesus θ-Defensins and Pig Neutrophil Protegrin PG-1

This example describes membranolytic activity of θ-defensins and protegrin analogs.

Twenty θ-defensin and protegrin analogs (FIG. 5A) were produced using Fmoc solid phase methodology as described in Example II. Linear peptides were air oxidized to form the disulfides. The cyclic peptides (peptides 2, 4, 6, 13 and 16) were produced from appropriate acyclic analogs (analogs 3, 5, 7, 14, and 17, respectively) using the EDC/HOBt cyclization method (Tang et al., supra, 1999). The RP-HPLC purified peptides were characterized by analytical RP-HPLC, AU-PAGE, MALDI-TOF MS, and amino acid analysis as described in Example II.

The microbicidal activities of each peptide against *E. coli* ML35, *S. aureus* 502a, and *C. albicans* 16820 were determined with cell-suspension microbicidal assays in 96-well plates (see Example II). Briefly, log-phase cells ($2 \times 10^6$ CFU/ml final) were incubated with increasing concentrations of peptides (0–8 μg/ml final) in 50 μl of 10 mM PIPES, 5 mM glucose, pH 7.4, for 2 h at 37° C. Incubation mixtures were diluted 1:10 to $1:10^6$ with trypticase-soy broth (bacteria) or Sabaraud dextrose broth (fungi) and incubated at 37° C. for 24–48 h until cell pellets were visible. Microbicidal activities (confirmed in control experiments as described in Example II) were determined as the absence of a cell pellet in the various dilutions. Peptide concentrations that caused ≧99.9% killing (absence of a cell pellet at 1:103 dilution) were taken as the minimum microbicidal concentrations (MMC).

For the membrane permeabilization assay, the permeabilization of bacterial cytoplasmic membranes was determined by measuring hydrolysis of o-nitrophenyl-β-D-galactcpyranoside (ONPG) in *E. coli* ML35 (Sitaram et al., *FEBS Lett.* 303:265–268 (1992); Lehrer et al., *J. Immunol. Methods* 108:153–158 (1988)). Peptides dissolved in 5 μl of 0.01% acetic acid were two-fold serially diluted with 10 mM PIPES, pH 7.4, containing 3 mM ONPG, to final peptide concentrations of 0–8.0 μg/ml. Log-phase bacteria, prepared in PIPES buffer as described for the microbicidal assay (see Example I), were added to $1 \times 10^6$ CFU/ml final density in a final volume of 90 μl. ONPG hydrolysis was measured at 405 nm for 60 min using a SpectraMAX 190 plate reader and SOFTmaxPRO 3.1 (Molecular Devices Corp., CA).

The effect of each peptide on β-galactosidase-dependent ONPG hydrolysis was determined by incubating 0–4 μg/ml of each peptide with recombinant β-galactosidase (a gift from Dr. Donald P. Satchell, University of California, Irvine, Department of Pathology) and 3 mM ONPG as described above. Dose-dependent inhibition of 10 nM β-galactosidase was determined for each peptide and used to calculate an adjusted rate of ONPG hydrolysis in whole bacteria as follows:

$$R'=R+[-\log_{10}C\times m]+(\Delta b)$$

where R'=adjusted rate, R=observed rate, C=peptide concentration, m=slope obtained from a log-linear plot of the dose-dependent β-galactosidase inhibition by each peptide, and Δb=difference of the y-intercepts obtained from plots of ONPG hydrolysis rates by purified β-galactosidase in 10 mM PIPES buffer and identical mixtures containing 1 μg/ml of each peptide.

For the hemolysis assay, the hemolytic activity of each peptide was determined by the method of Tam et al. (Tam et al., *Eur. J. Biochem.* 267:3289–3300 (2000)). Blood was obtained from a healthy donor in accordance to a protocol approved by the Institutional Review Board. Normal human serum was prepared from the same individual and stored at −20° C. Red blood cells (RBC) were prepared from blood collected in EDTA. RBC were harvested at 234×g for 10 min, 22° C., washed four times with 10 mM sodium phosphate, 150 mM NaCl, pH 7.4 (PBS), containing 4 mM EDTA and resuspended in PBS without EDTA. Peptides dissolved in 10 μl 0.01% HOAc were diluted with PBS to final concentrations of 0.3–100 μg/ml. RBC were added to a 2% final density in 100 μl. Incubation mixtures were also prepared with 10% serum. After 1 h incubation at 37° C., the cell suspensions were centrifuged at 234×g for 10 min, 22° C. Fifty-μl samples of the supernatants were removed, and the absorbance at 405 nm (A) was measured. Hemolytic activity of each peptide was calculated relative to lysis by 1% NP-40 using the following formula:

$$\% \ hemolysis = \frac{A_{peptide} - A_{buffer}}{A_{1\% NP-40} - A_{buffer}} \times 100\%$$

A selectivity index (SI=H/M) was calculated as a ratio of a peptide concentration (μg/ml) that causes 3% hemolysis (H) obtained from a dose-dependent hemolysis plot over 0.3 to 3 μg/ml of each peptide in PBS and the lowest MMC value (M) for any of the three test microorganisms (see Example II; Table 2).

Synthetic RTD 1, 2 and 3, PG-1, and their analogs were produced as described in Example II to test the effects of cyclization, carboxamidation, inclusion of two and three disulfide bonds, and varying lengths of chain termini on peptide activities (FIG. 5A). The purity of each peptide (≧99%) was determined by analytical RP-HPLC, and the purified peptides were characterized by amino acid analysis, MALDI-TOF MS, and AU-PAGE (see Example II). The minimum microbicidal concentration (MMC) of each peptide against *E. coli*, *S. aureus*, and *C. albicans* was determined in microbicidal assays as described in Example II. The peptide MMC's against *E. coli* are listed in Table 4. The lowest MMC value for each peptide against any of the three test organisms is shown in Table 5.

Figure 8A:
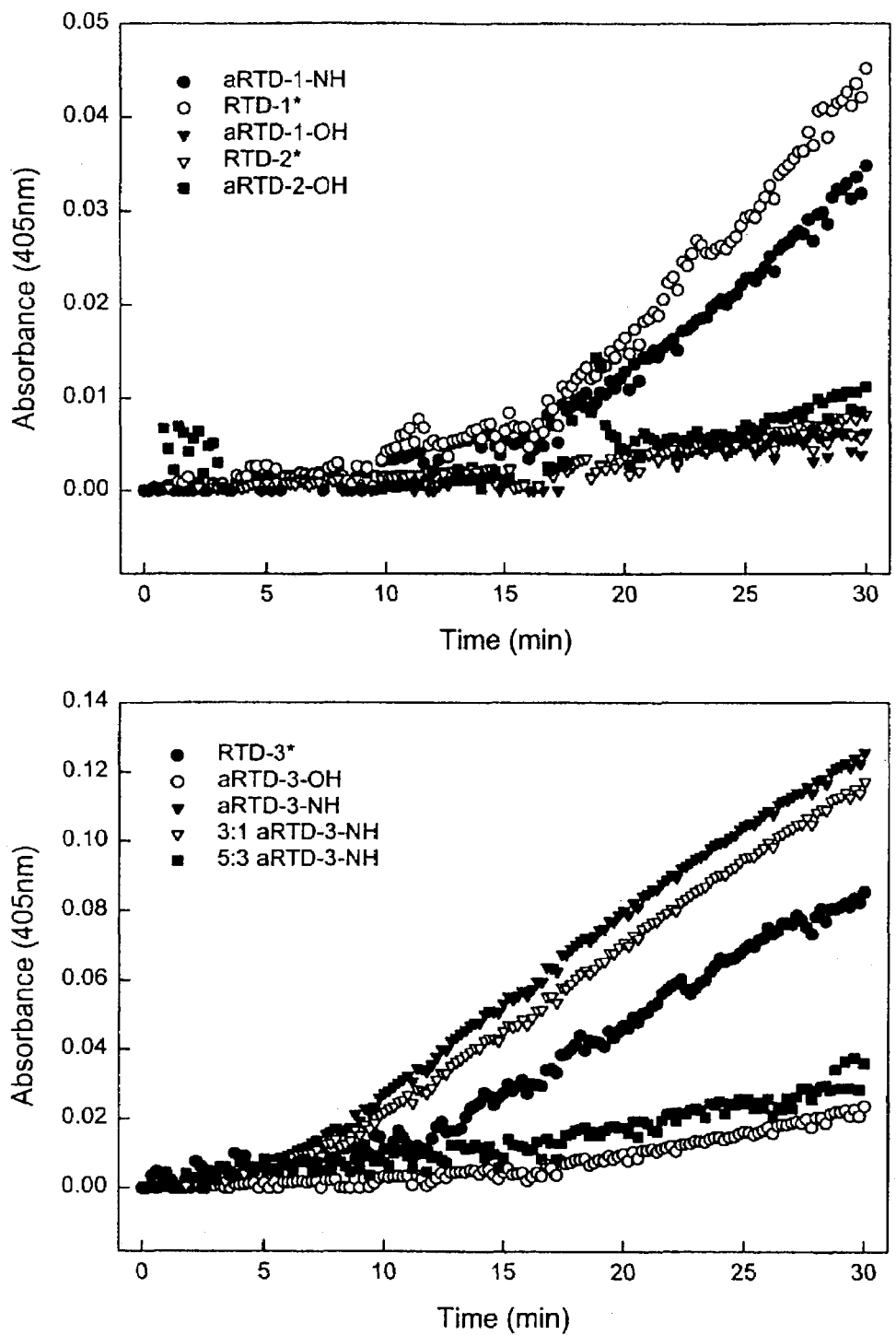
FIGS. 8A and 8B show permeabilization of bacterial cells by θ-defensins, PG-1, and analogs. Permeabilization of E. coli ML35 was determined as ONPG hydrolysis ($A_{405}$) in log-phase bacteria during the 30-min incubation with 1 μg/ml of each peptide.
Figure 8B:
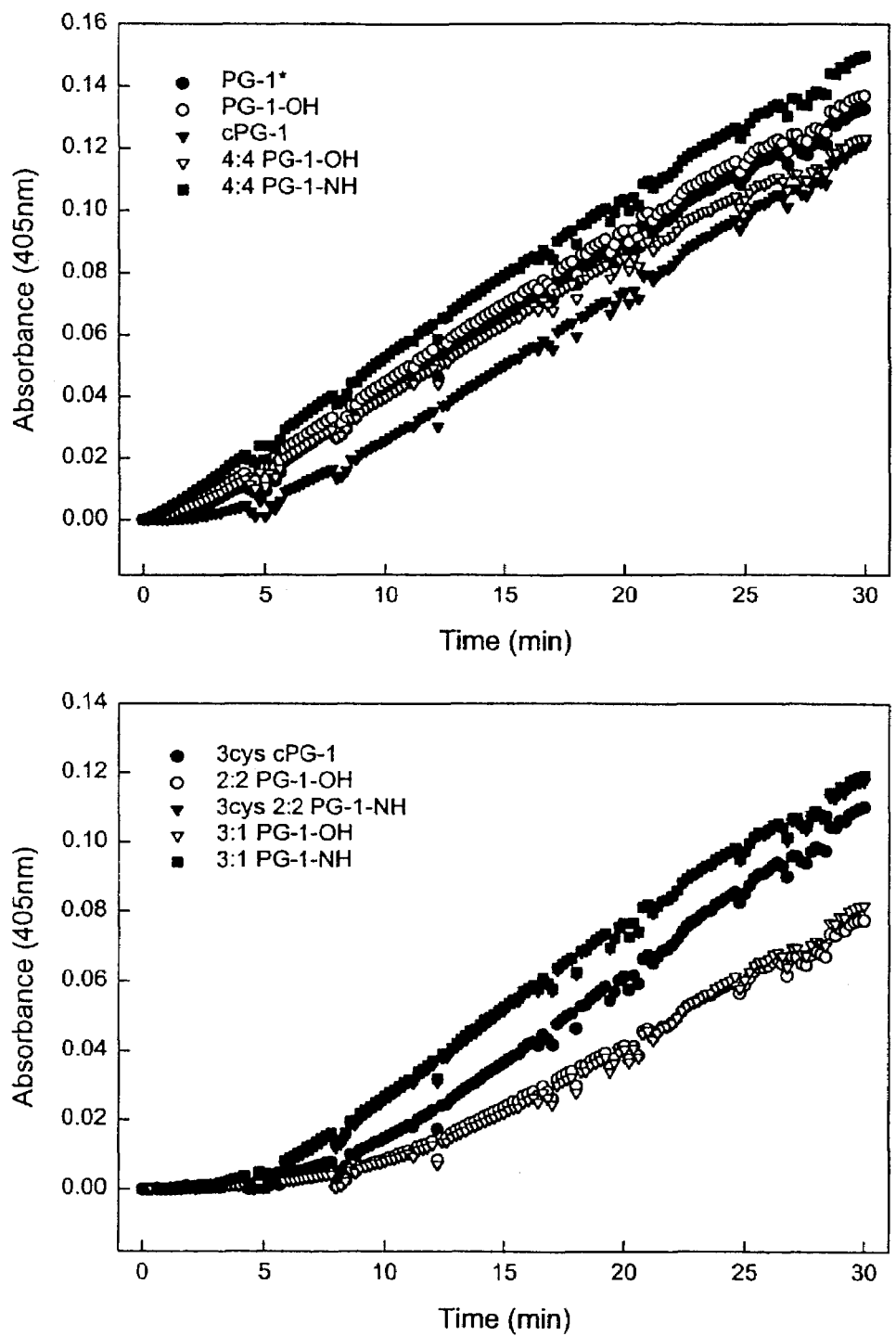

Permeabilization of *E. coli* cytoplasmic membranes by θ-defensins, PG-1 and analogs. To determine whether the microbicidal action of the peptides under investigation is due to (or closely linked with) disruption of the bacterial cytoplasmic membrane, permeabilization of *E. coli* cells was determined by measuring the rates of ONPG hydrolysis. In initial experiments, ONPG hydrolysis was observed for all test peptides (FIG. 8). However, the dose-dependent rates of ONPG hydrolysis (FIG. 9) demonstrated that RTD-1 and RTD-3 permeabilized *E. coli* cells to a greater extent than RTD-2 despite the nearly identical MMC's (2.0–2.3 μg/ml) of the three θ-defensins (Table 4). Furthermore, the rates of ONPG hydrolysis by nearly all of the 20 peptides reached a maximum at 1–2 μg/ml of peptide but were reduced at 4–8 μg/ml. These findings indicate that hydrolysis of ONPG was inhibited by increasing peptide concentrations.

Figure 10:
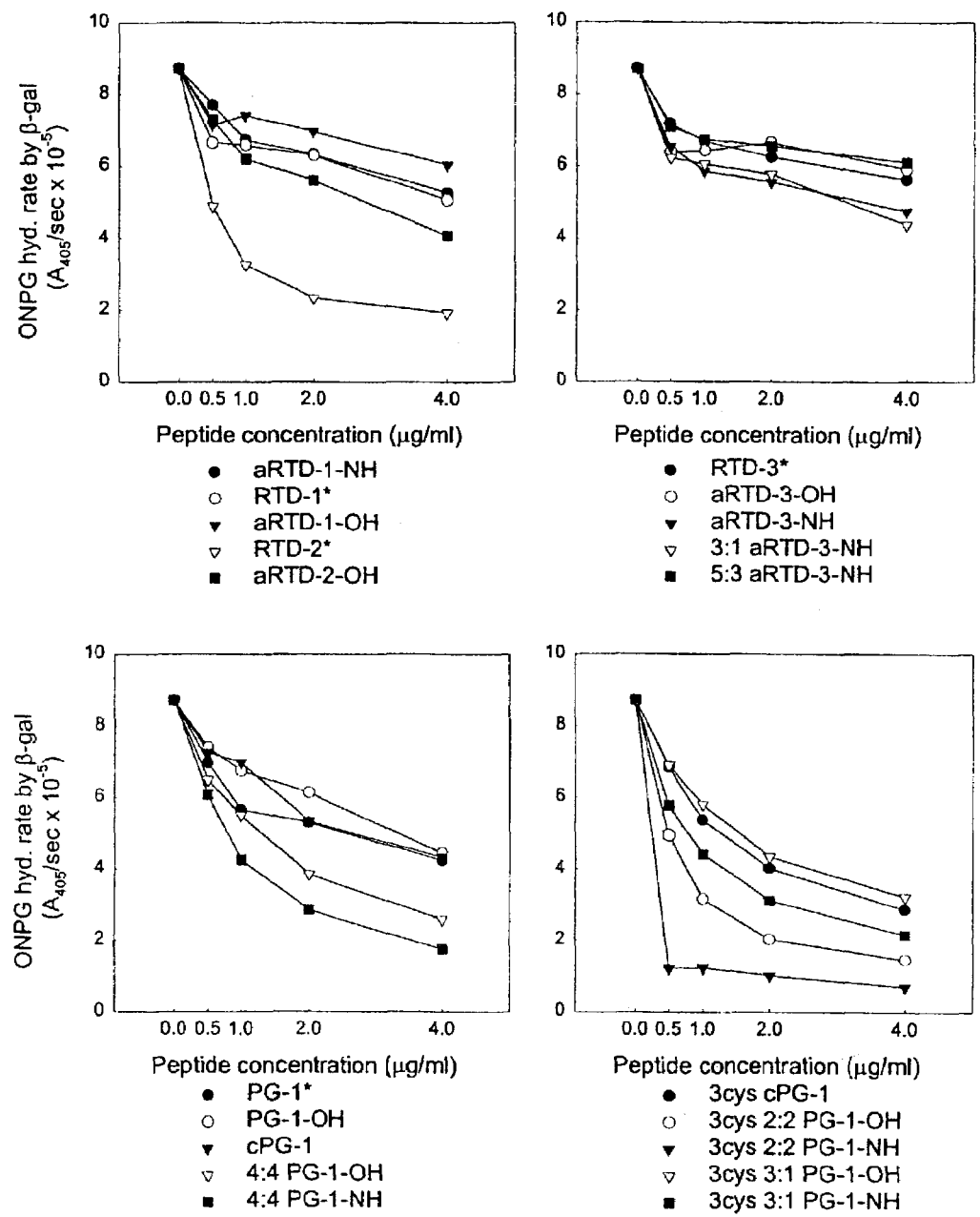
FIG. 10 shows inhibition of β-galactosidase by θ-defensins, PG-1, and analogs. Dose-dependent rates of ONPG hydrolysis were determined using 10 nM of purified β-galactosidase.

Experiments were performed using purified β-galactosidase to determine the effect of each peptide on β-galactosidase activity. As shown in FIG. 10, all 20 peptides caused some degree of direct inhibition of β-galactosidase activity. RTD-1, RTD-3 and θ-defensin analogs 5–10 reduced ONPG hydrolysis by 50% at the highest peptide concentration tested (4 μg/ml). At 2 μg/ml of RTD-2, the rate of ONPG hydrolysis was reduced by 80% relative to those in incubations without peptide, indicating that the peptide is a potent inhibitor of β-galactosidase. Protegrin PG-1 and the two-disulfide PG-1 analogs (peptides 11–15) inhibited β-galactosidase activity by 75–80%, and the tridisulfide θ-defensin-PG-1 hybrids (peptides 16–20) also reduced ONPG hydrolysis to similar extent. Like RTD-2, the 3cys 2:2 PG-1-NH (peptide 18) was also a potent inhibitor of β-galactosidase, causing a steep dose-dependent reduction in the rates of ONPG hydrolysis.

To determine whether β-galactosidase inhibition occurred intracellularly, extracellularly, or both, ONPG hydrolysis experiments were performed using supernatants from incubation mixtures of *E. coli* cells with 1 μg/ml peptide, a concentration that was bactericidal and caused permeabilization of bacterial cells (FIG. 8). Hydrolysis of ONPG was not detected in these supernatants, indicating that the 465-kDa β-galactosidase remained within the bacterial cell. Thus, the inhibition of ONPG hydrolysis in incubations containing *E. coli* ML35 indicated that inhibition of β-galacuosidase activity occurs in the bacterial cytoplasm, providing evidence that the peptides actually enter the-cytosol.

Figure 9:
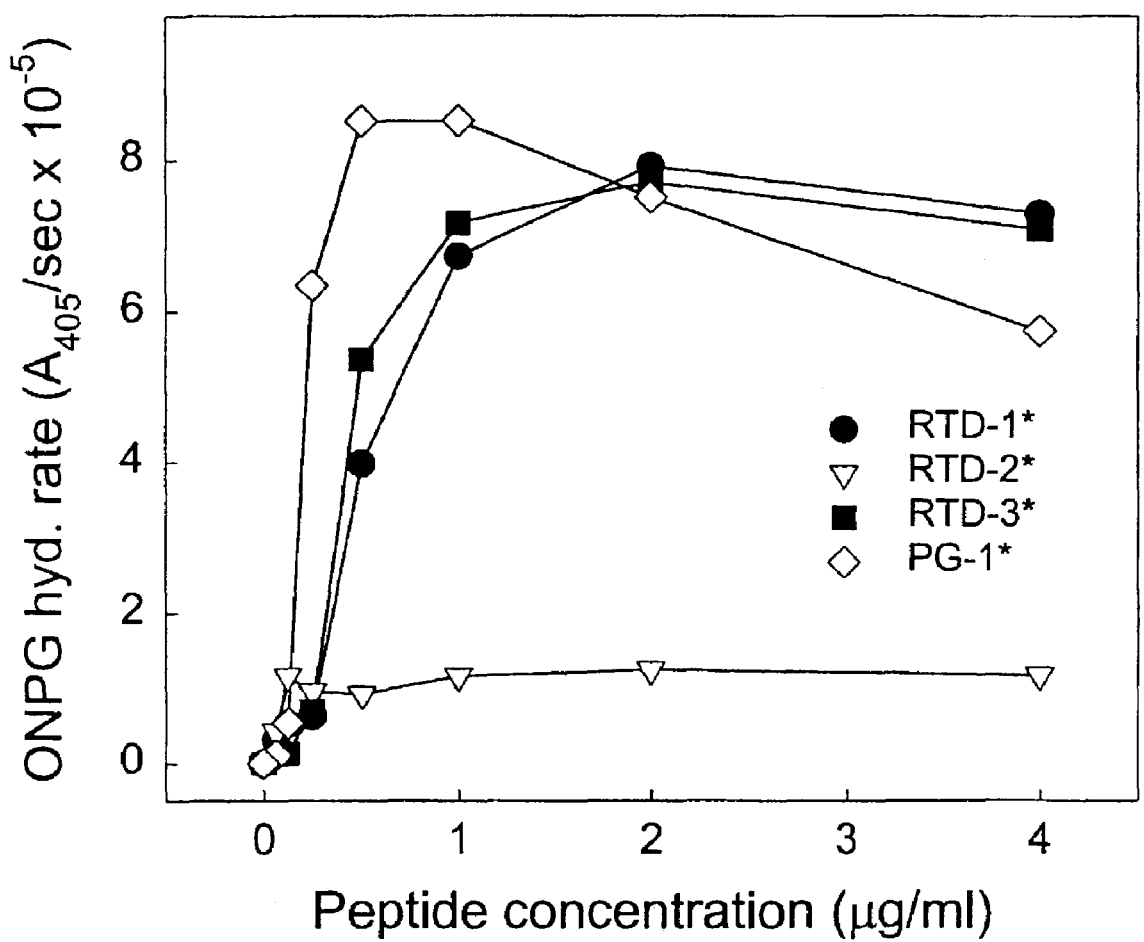
FIG. 9 shows dose-dependent rates of ONPG hydrolysis by RTD-1, 2 and 3 and PG-1. The rates of ONPG hydrolysis ($A_{405}$/sec) in E. coli ML35 were determined as the highest slope from the kinetic data for each peptide as shown in FIG. 8. The dose-dependent ONPG hydrolysis rates of θ-defensin and PG-1 analogs resemble those of RTD-1 and PG-1.
Figure 11:
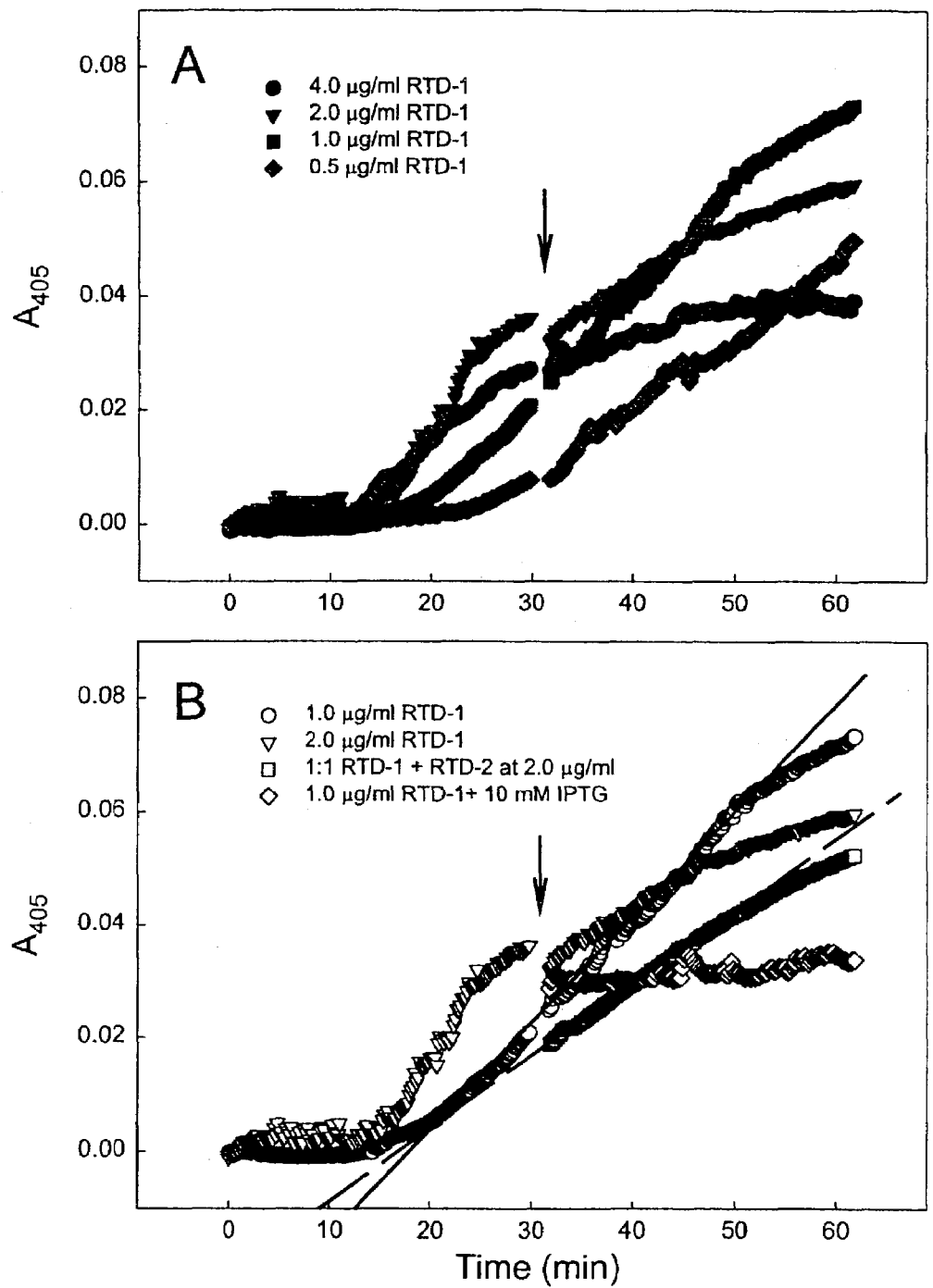
FIG. 11 shows permeabilization of E. coli cells and internalization of the θ-defensin into the bacterial cytoplasm.

To test whether θ-defensins are internalized by peptide-permeabilized *E. coli* ML35, ONPG-hydrolysis experiments were performed using RTD-1 and RTD-2, two θ-defensins that inhibit β-galactosidase to different degrees. *E. coli* cells were permeabilized with 0.5–4.0 μg/ml RTD-1 (FIGS. 9 and 11A). The rates of ONPG hydrolysis increased to a maximum at 2 μg/ml of peptide and then decreased at the highest concentration tested (4 μg/ml). After 30 min (indicated by the arrows), RTD-2 (1.0 μg/ml final) and isopropyl-β-D-thiogalactopyranoside (IPTG, 10 mM final) were added to replicate incubations. IPTG, a non-hydrolyzable analog of ONPG, rapidly halted the hydrolysis of ONPG (FIG. 11B). Addition of RTD-2 reduced the rate of ONPG hydrolysis by approximately 30% (FIG. 11B, dashed line) relative to the rate for 1 μg/ml of RTD-1 (solid line). These data indicate that RTD-2 was also internalized into the bacterial cytoplasm, where it inhibited β-galactosidase. The kinetics of ONPG hydrolysis by 2 μg/ml of RTD-1 rose to a maximum after the initial 10 min of incubation but decreased after 25 min. These results indciate that after the initial permeabilization of *E. coli* membranes, RTD-1 was also internalized, and like RTD-2, inhibited the activity of the cytoplasmic β-galactosidase. These results are consistent with the hypothesis that θ-defensins permeabilize the *E. coli* cells and allow passage of normally excluded molecules across the cytoplasmic membranes. Permeabilization of the bacterial cell envelope facilitates the internalization of peptides into the cytoplasmic space, where essential cellular functions can also be inhibited.

Figure 12:
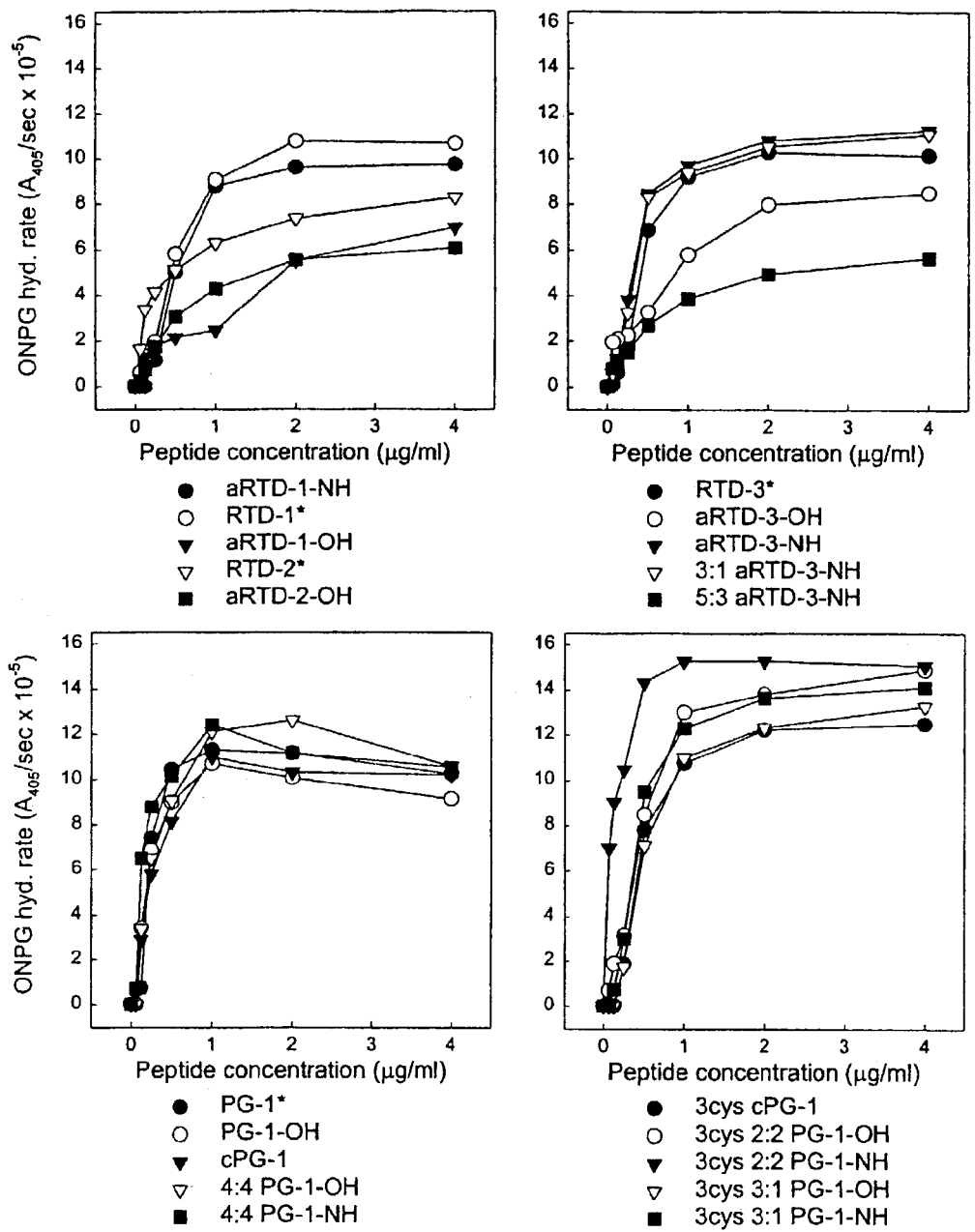
FIG. 12 shows dose-dependent permeabilization of E. coli ML35 by θ-defensins, PG-1 and analogs. The rates of ONPG hydrolysis ($A_{405}$/sec) were measured and adjusted for the inhibition of β-galactosidase activity.

The direct inhibition of β-galactosidase and the peptide internalization appear to explain the reduction of ONPG hydrolysis rates with increasing peptide concentrations above 1–2 μg/ml (FIG. 9). Permeabilization of E. coli cells can enable extracellular peptide to equilibrate with the bacterial cytosol. Based on this model, a set of corrections was derived from the dose-dependent inhibition of β-galactosidase activity (FIG. 10) and used to adjust for the observed ONPG hydrolysis rates by the twenty peptides. The adjusted dose-dependent rates of ONPG hydrolysis for all twenty peptides rose to a maximum and reached a plateau at concentrations close to the peptide MMC values against E. coli (FIG. 12).

Figure 13:
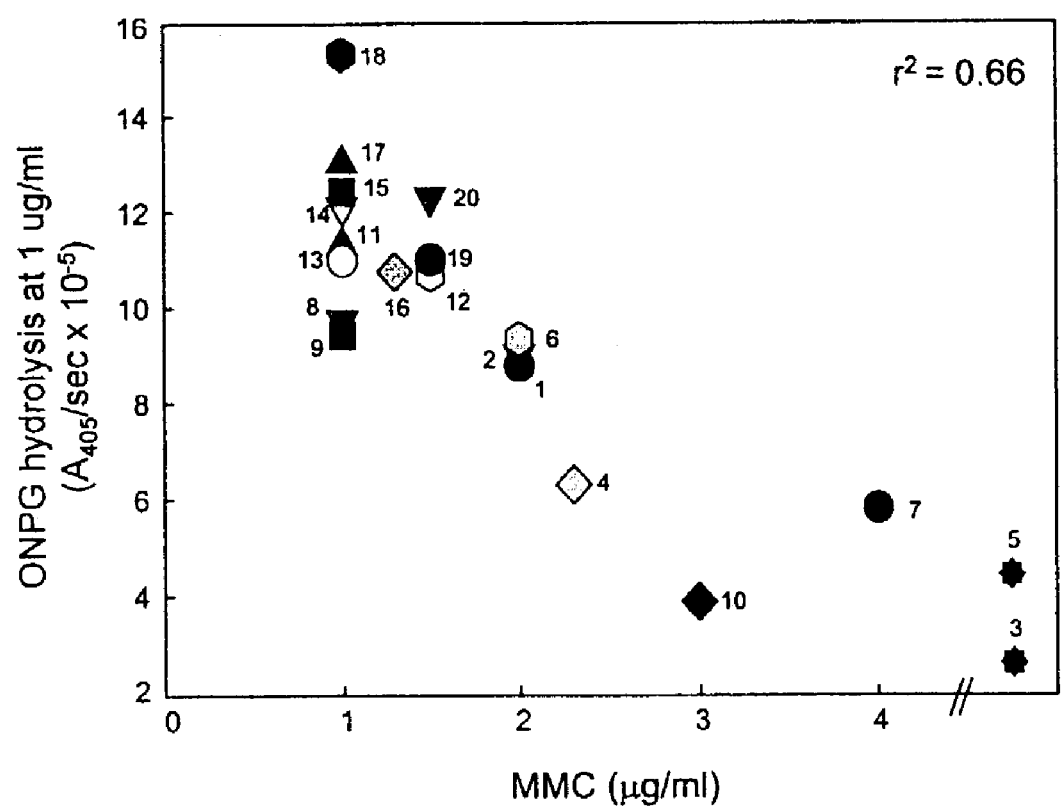
FIG. 13 shows a scatter plot of the rates of ONPG hydrolysis and bactericidal potencies of θ-defensins, PG-1, and analogs. ONPG-hydrolysis rates and MMC values (Table 3) were used to determine the correlation between permeabilization of E. coli cells and bacterial killing.

To correlate membrane permeabilization with killing of bacteria, the maximum rates of ONPG hydrolysis by the twenty peptides were compared with their relative microbicidal potencies (MMC) against E. coli ML35 (Table 4). Peptides with high MMC values induced low rates of ONPG hydrolysis and vice versa, demonstrating that there is a correlation ($r^2=0.66$) between the peptide membrane permeabilizing potentials and bactericidal activities (FIG. 13). For example, aRTD-1-OH, aRTD-2-OH, and aRTD-3-OH, 5:3 aRTD-3-NH (peptides 3, 5, 7, and 10) have high MMC values ($\geqq 3$ μg/ml) and low rates of ONPG hydrolysis ($2.4$–$5.8 \times 10^{-5}$ $A_{405}$/sec), whereas RTD-1, RTD-3, PG-1 and several analogs with potent microbicidal activities (MMC=1–2 μg/ml) induce high rates of ONPG hydrolysis ($9$–$12 \times 10^{-5}$ $A_{405}$/sec). This correlation suggests that permeabilization of the cytoplasmic membranes is closely linked with killing of E. coli by θ-defensins, protegrin-1, and the various analogs. It is important to note that the MMC's of peptides 8, 9, 11, 13–15, 17, and 18 are identical (1 μg/ml) while their respective membrane permeabilization potentials (ONPG hydrolysis rates) are significantly different ($9.4$–$15.3 \times 10^{-5}$ $A_{405}$/sec) (Table 4 and FIG. 13). The differing rates of ONPG hydrolysis are likely indicative of bactericidal activities at peptide concentrations below 1 μg/ml. Because MMC's were defined as $\geqq$3-log kill, the relationship between killing and permeabilization can be obscured in quantitative terms. This suggests that a plot equating 90–99% bactericidal activities (i.e. 1 or 2-log kill) and permeabilization can be used to further analyze the relationship between these two functional parameters.

TABLE 4

| | ONPG hydrolysis[a] ($A_{405}$/sec) · $10^{-5}$ | MMC[b] (μg/ml) |
|---|---|---|
| 1. aRTD-1-NH[c] | 8.8 | 2.0 |
| 2. RTD-1* | 9.0 | 2.0 |
| 3. aRTD-1-OH | 2.4 | (99%)[d] |
| 4. RTD-2* | 6.3 | 2.3 |
| 5. aRTD-2-OH | 4.3 | (90%)[d] |
| 6. RTD-3* | 9.2 | 2.0 |
| 7. aRTD-3-OH | 5.8 | 4.0 |
| 8. aRTD-3-NH | 9.7 | 1.0 |
| 9. 3:1 aRTD-3-NH | 9.4 | 1.0 |
| 10. 5:3 aRTD-3-NH | 3.9 | 3.0 |
| 11. PG-1* | 11.3 | 1.0 |
| 12. PG-1-OH | 10.7 | 1.5 |
| 13. cPG-1 | 11.0 | 1.0 |
| 14. 4:4 PG-1-OH | 12.1 | 1.0 |
| 15. 4:4 PG-1-NH | 12.4 | 1.0 |
| 16. 3cys cPG-1 | 10.7 | 1.3 |
| 17. 3cys 2:2 PG-1-OH | 13.0 | 1.0 |
| 18. 3cys 2:2 PG-1-NH | 15.3 | 1.0 |

TABLE 4-continued

| | ONPG hydrolysis[a] ($A_{405}$/sec) · $10^{-5}$ | MMC[b] (μg/ml) |
|---|---|---|
| 19. 3cys 3:1 PG-1-OH | 11.0 | 1.5 |
| 20. 3cys 3:1 PG-1-NH | 12.3 | 1.5 |

Figure 14:
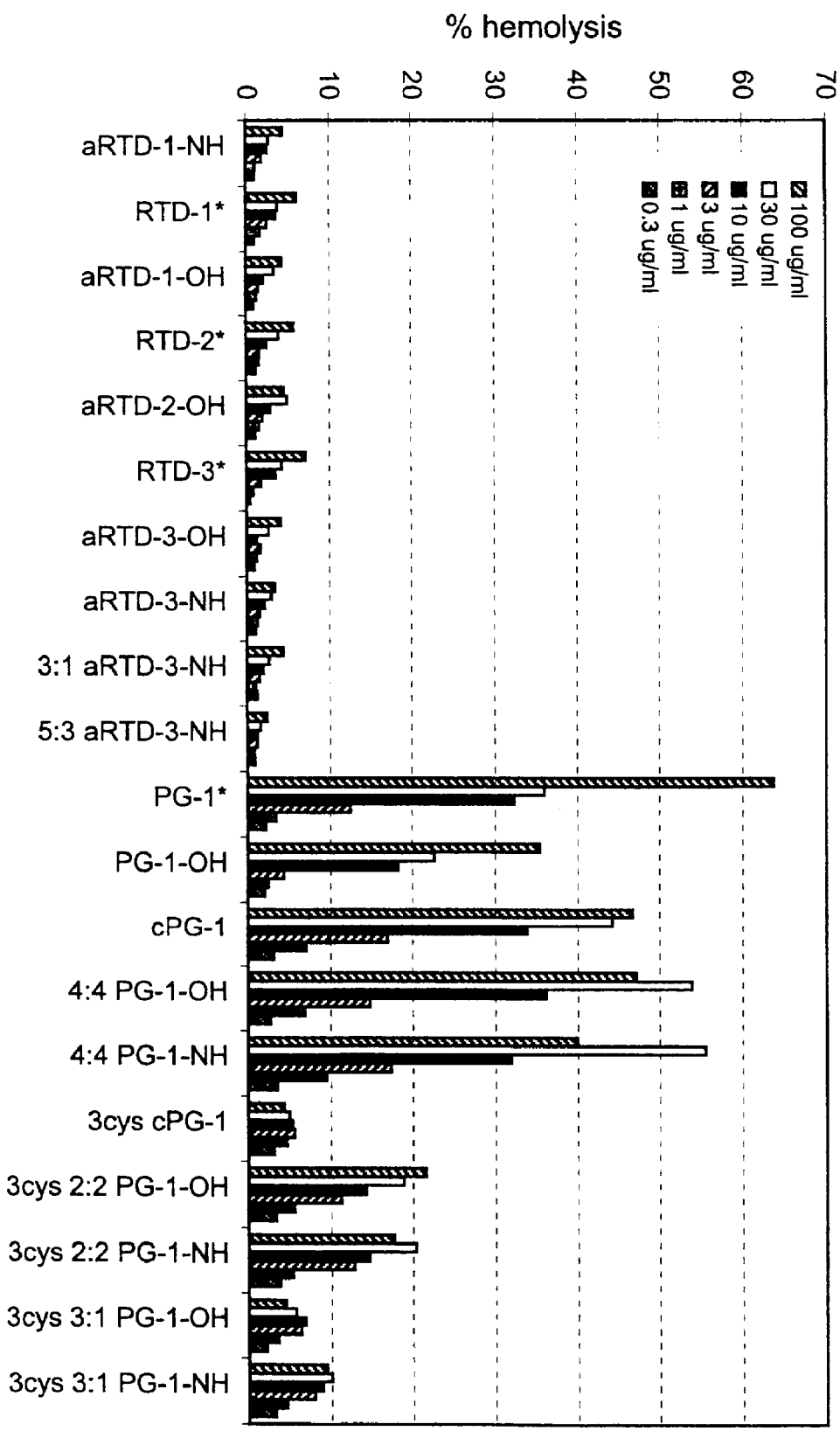
FIG. 14 shows hemolytic activities of θ-defensins, PG-1, and analogs. Hemolysis (%) was determined as a function of increasing peptide concentrations.

[a]rates at 1 μg/ml concentration of each peptide shown in FIG. 8
[b]values against E. coil ML35 from Table 2
[c]see FIG. 5 for peptide identities
[d]the 99.9% microbial killing defined for MMC was not reached. Killing percentages at 8 μg/ml, the highest concentration tested, are shown
*native sequences Hemolytic activities of θ-defensin and PG-1 analogs. Killing of E. coli by θ-defensins, PG-1, and analogs appears to be linked to permeabilization of the cytoplasmic membrane. To investigate whether the peptides also permeabilize mammalian cells, and thereby disclosing the peptide selectivity for microbial targets, hemolytic activity of each peptide was determined by incubating human erythrocytes with increasing peptide concentrations in 10 mM sodium phosphate-buffered saline and in incubation mixtures containing 10% autologous normal human serum (NHS). Hemolysis was measured spectrophotometrically and calculated as a percentage of maximum hemolysis (1% NP-40; see above). RTD 1, 2 and 3 and the seven θ-defensin analogs (peptides 1–10) were only weakly hemolytic; 100 μg/ml of each peptide caused less than 10% hemolysis. Acyclic θ-defensins (aRTD-1–3-OH) and carboxamidated analogs aRTD-1-NH and aRTD-3-NH, which were produced to test the effect of de-cyclization and carboxamidation on peptide activities, were also weakly hemolytic (FIG. 14). The protegrin-RTD-3 hybrids (3:1aRTD-3-NH and 5:3 aRTD-3-NH) possessed little hemolytic activity, similar to native RTD-3, indicating that the inclusion of protegrin structural features (i.e. C-terminal amidation, a two-disulfide motif, and "overlapping" chain termini) did not confer the hemolytic properties of protegrin-1 (see below) to θ-defensins.

Protegrin-1 and the two-disulfide PG-1 analogs (peptides 11–15) caused 35–63% hemolysis at 30 and 100 μg/ml of peptide (FIG. 14). Native PG-1 was the most hemolytic of the twenty peptides causing 63% hemolysis at the highest concentration tested (100 μg/ml). PG-1-OH (peptide 12) was about 50% less hemolytic than native PG-1. However, PG-1-OH was also 2–3 fold less microbicidal than PG-1 (Table 5; see also Example II). These results indicate that de-amidation of protegrin decreases the protegrin cytocidal activity without altering its selectivity for microbial targets.

TABLE 5

| | M[a] (μg/ml) | H[b] (μg/ml) | Selective index (H/M) |
|---|---|---|---|
| 1. aRTD-1-NH[c] | 1 | 8.8 | 8.8 |
| 2. RTD-1* | 1 | 5.5 | 5.5 |
| 3. aRTD-1-OH | 4 | 15.0 | 3.8 |
| 4. RTD-2* | 1.5 | 21.4 | 14.3 |
| 5. aRTD-2-OH | 1.5 | 10.0 | 6.7 |
| 6. RTD-3* | 1 | 6.3 | 6.3 |
| 7. aRTD-3-OH | 1.5 | 11.1 | 7.4 |
| 8. aRTD-3-NH | 0.75 | 16.7 | 22.2 |
| 9. 3:1 aRTD-3-NH | 0.75 | 18.8 | 25.0 |
| 10. 5:3 aRTD-3-NH | 1 | 23.1 | 23.1 |
| 11. PG-1* | 0.38 | 0.8 | 2.0 |
| 12. PG-1-OH | 1.5 | 1.7 | 1.2 |
| 13. cPG-1 | 1 | 1.0 | 1.0 |
| 14. 4:4 PG-1-OH | 1 | 0.9 | 0.9 |

TABLE 5-continued

|  | $M^a$ (µg/ml) | $H^b$ (µg/ml) | Selective index (H/M) |
|---|---|---|---|
| 15. 4:4 PG-1-NH | 0.5 | 1.1 | 2.2 |
| 16. 3cys cPG-1 | 0.5 | 3.7 | 7.3 |
| 17. 3cys 2:2 PG-1-OH | 1 | 1.0 | 1.0 |
| 18. 3cys 2:2 PG-1-NH | 0.25 | 0.9 | 3.5 |
| 19. 3cys 3:1 PG-1-OH | 0.5 | 0.7 | 1.3 |
| 20. 3cys 3:1 PG-1-NH | 1.5 | 1.7 | 1.2 |

[a]peptide concentration that kill 99.9% of either *S. aureus, E. coil,* or *C. albicans* taken from MMC values in Table 2
[b]peptide concentration that causes 3% hemolysis calculated from the dose-dependent hemolysis plot over 0.3–3 µg/ml peptide concentrations as shown in FIG.14
[c]see FIG. 5 for peptide identities
*native sequences Peptide cyclization alone did not confer the non-hemolytic property of θ-defensins upon protegrin-1, as indicated by the 40–50% hemolysis of the cyclized cPG-1 hybrid (peptide 13). The three-disulfide (3cys) θ-defensin-PG-1 hybrids (peptides 16–20) were significantly less hemolytic than the two-disulfide analogs. The hemolytic activities of 3cys 3:1 PG-1 hybrids (peptides 19–20) were 3- to 5-fold less than those of the two-disulfide analogs (peptides 11–12), indicating that the tridisulfide motif contributed to the low-hemolytic properties of θ-defensin-PG-1 hybrids. The 5–6% hemolysis of 3cys cPG-1 (peptide 16) demonstrated that structural features of RTD 1–3 confer the low-hemolytic properties of θ-defensins upon PG-1. These results also indicate that the tridisulfide motif of θ-defensins contributes to the reduced hemolytic activities of PG-1 analogs. Interestingly, the 3cys 2:2 PG-1 analogs with even-chain termini (peptides 17–18) were two fold more hemolytic than the 3cys 3:1 PG-1 with overlapping-termini (peptides 19–20), suggesting that even-chain termini causes an increase in hemolysis. In either case, C-terminal amidation appears to have little effect on the hemolytic activities of tridisulfide θ-defensin-PG-1 hybrids.

Figure 15:
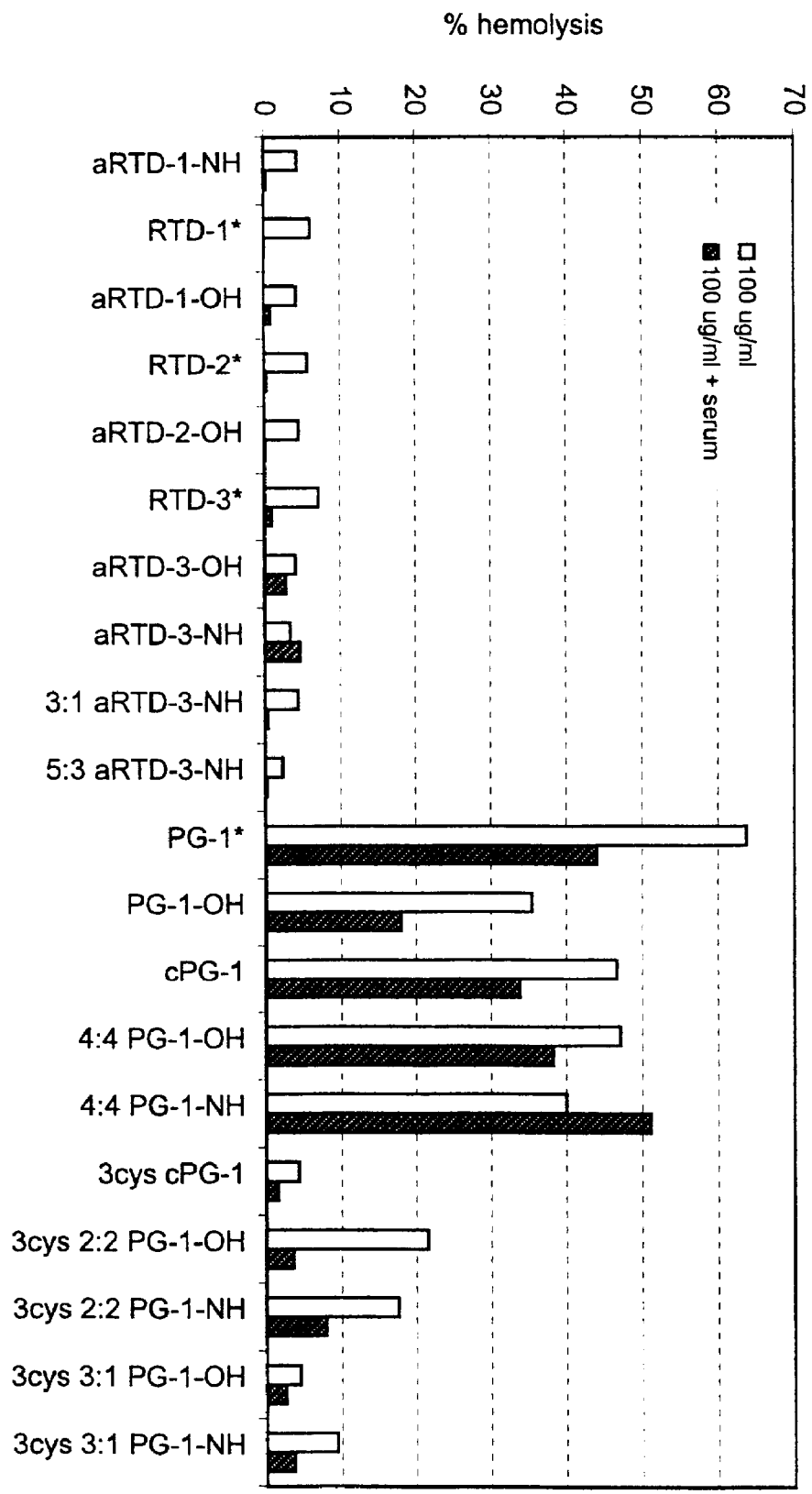
FIG. 15 shows the effect of serum on the hemolytic activities of θ-defensins, PG-1 and analogs. Hemolysis by 100 μg/ml each of the twenty peptides was determined in 10% autologous normal human serum (NHS).
Figure 16:
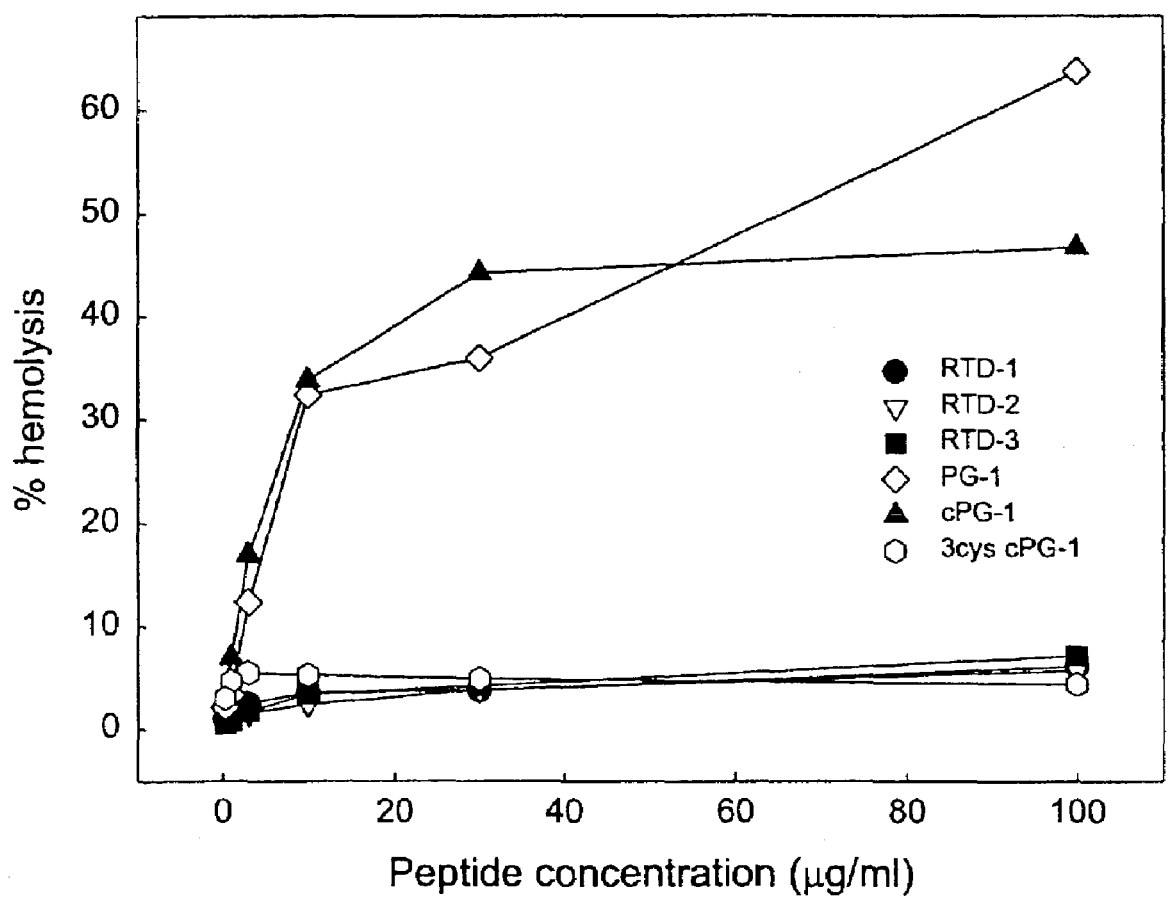
FIG. 16 shows that cyclization and the tridisulfide motif are associated with low hemolytic potential of natural θ-defensins and 3cys cPG-1. Dose-dependent hemolytic activities of RTD-1, 2 and 3, PG-1 and cyclic θ-defensin-protegrin hybrids cPG-1 and 3cys cPG-1 were determined.

Hemolysis by the twenty peptides was generally attenuated in assays containing 10% normal human serum (FIG. 15). However, the staphylocidal activities of all twenty peptides persisted in assays containing serum (see Example II), indicating that the addition of serum reduces peptide cytotoxicity without significantly affecting microbicidal activity. The low-hemolysis by RTD 1–3 was virtually ablated by the addition of 10% serum. However, serum had little effect on the hemolytic activities of θ-defensin analogs 7–8, which possess the even-termini structure.

The hemolytic activities of the two-disulfide PG-1 analogs were somewhat attenuated in assays containing 10% NHS, but hemolysis persisted at between 20 and 50% for each peptide at 100 µg/ml (FIG. 15). Interestingly, while varying the lengths of the chain termini did not reduce the hemolytic activity of the two 4:4 PG-1 analogs (FIG. 14), the 4:4 PG-1-NH was more hemolytic in incubations containing 10% NHS. The 3cys 2:2 PG-1-NH peptide with even-chain termini was also more hemolytic than the other tridisulfide θ-defensin-PG-1 hybrids. These results suggest that the even-termini structure increases hemolytic activities of the PG-1 analogs.

Cytocidal selectivities of θ-defensin and PG-1 analogs. The relative cytocidal selectivity of the twenty peptides under investigation was determined by comparing selectivity index of each peptide, as described above. As summarized in Table 5, the selectivity indices of the twenty peptides ranged from 0.9 to 25.0. The low-hemolytic activities of θ-defensins combined with their potent microbicidal activities contributed to the high degrees of selectivity for RTD 1, 2 and 3. The least cationic θ-defensin, RTD-2 (S.I.=14.3), was 2- to 2.5-fold more selective than RTD-1 (S.I.=5.5) and RTD-3 (S.I.=6.3), indicating that a low net charge enhances peptide selectivity. Acyclic θ-defensins (aRTD 1–3-OH) had similar S.I. values to those of native RTD 1, 2 and 3, indicating that de-cyclization had little effect on the cytocidal selectivity of θ-defensins, even though microbicidal potencies were somewhat attenuated (Table 5, also see Example II). The selectivities of carboxamidated aRTD-3-NH, 3:1 aRTD-3-NH, and 5:3 aRTD-3-NH were 3 to 4-fold higher than those of native RTD-3. However, the spectra of activities of these three analogs were reduced, as indicated by the high MMC's of aRTD-3-NH (4.5 µg/ml) and 3:1 aRTD-3-NH (>8 µg/ml) against *S. aureus,* and of 5:3 aRTD-3-NH against *E. coli* (3 µg/ml) and *C. albicans* (2.3 µg/ml) compared to those of native RTD-3 (1–2 µg/ml) (see Example II; Table 2). Since the lowest MMC value of each peptide against any of the three organisms was used to calculate the selectivity index, this reduction in spectrum of activity was not indicated by these S.I. values.

Compared to θ-defensins, PG-1 was three-fold less selective than RTD-1 and 3, and was 7-fold less selective than RTD-2 (Table 5). The low selectivity of PG-1 is predominantly a function of the peptide's hemolytic activity (FIG. 14). The selectivity indices of cyclic cPG-1, PG-1-OH, and 4:4 PG-1-OH were about 50% lower than those of the amidated analogs (4:4 PG-1-NH and PG-1) due to the fact that cyclization and de-amidation reduce PG-1 microbicidal potency without altering its hemolytic activity. However, a combination of peptide cyclization and increased disulfide constraint (three-disulfide motif) enhanced the selectivity of 3cys cPG-1 by nearly four-fold relative to that of the native peptide, consistent with the observation that certain structural features of RTD 1, 2 and 3 endow protegrin analogs with low-hemolytic activity without significantly affecting microbicidal potency. The selectivity indices of tridisulfide (3cys) 2:2 PG-1-OH and 3:1 PG-1-OH (peptides 17 and 20) were also lower than that of PG-1, despite the reduced hemolytic activities of the tridisulfide θ-defensin-PG-1 hybrids. The reduced selectivity was primarily due to the higher MMC values (Table 5). Peptide 19, 3cys 3:1 PG-1-OH, was less selective than PG-1 despite having nearly similar MMC but a steep dose-dependent hemolytic activity as indicated by the lowest H value (0.7) of all PG-1 analogs. Finally, the S.I. value of 3cys 2:2 PG-1-NH (peptide 18) was nearly two-fold higher than that of PG-1, indicating that increasing disulfide constraint and the even-termini structural feature enhances the peptide cytocidal selectivity.

PG-1 permeabilized the cytoplasmic membranes of both bacterial cells and human erythrocytes. However, θ-defensins were much more selective toward bacterial cells (Table 5). Thus, although θ-defensins and protegrin-1 share certain structural and microbicidal properties, θ-defensins are substantially less hemolytic than protegrin PG-1. The increased selectivity of carboxamidated acyclic RTD-1 and RTD-3 indicates that increasing peptide net charge can enhance the microbicidal potencies of θ-defensins without affecting their low-hemolytic properties.

EXAMPLE IV

Figure 17:
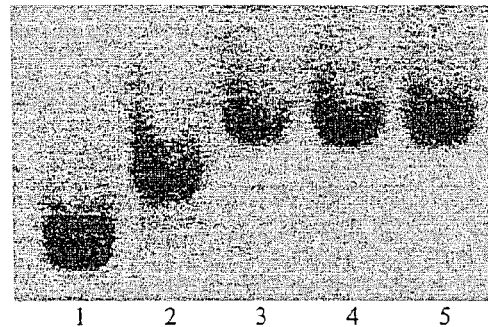
FIG. 17A shows a schematic of aRTD-1Hse[19] and RTD-1 construct, interrupted by a methionine residue, cloned into the pET-28a(+) vector (Novagen). Transformed E. coli were induced with IPTC, the cells lysed, and soluble 6-His-Tag fusion protein was purified on Ni-NTA resin. RTD-1-Hse[19] was produced by CNBr cleavage at the methionine residues (arrows). Acyclic RTD-1 (aRTD-1-OH), produced after N-terminal cleavage (open arrow), was cyclized using the EDC/HOBt protocol established for the synthesis of RTD-1.
FIG. 17B shows acid-urea PAGE of recombinant RTD-1, aRTD-1-OH, and aRTD-1-Hse[19]. One μg of purified recombinant aRTD-1-Hse[19] (lane 1), aRTD-1-OH (lane 2), and RTD-1 (lane 3) were compared to synthetic RTD-1 (lane 4) and a 1:1 mixture of recombinant and synthetic versions of RTD-1 (lane 5). Peptides were resolved on a 12.5% polyacrylamide gel and the gel was stained with formalin-Coomassie.
Figure 18:
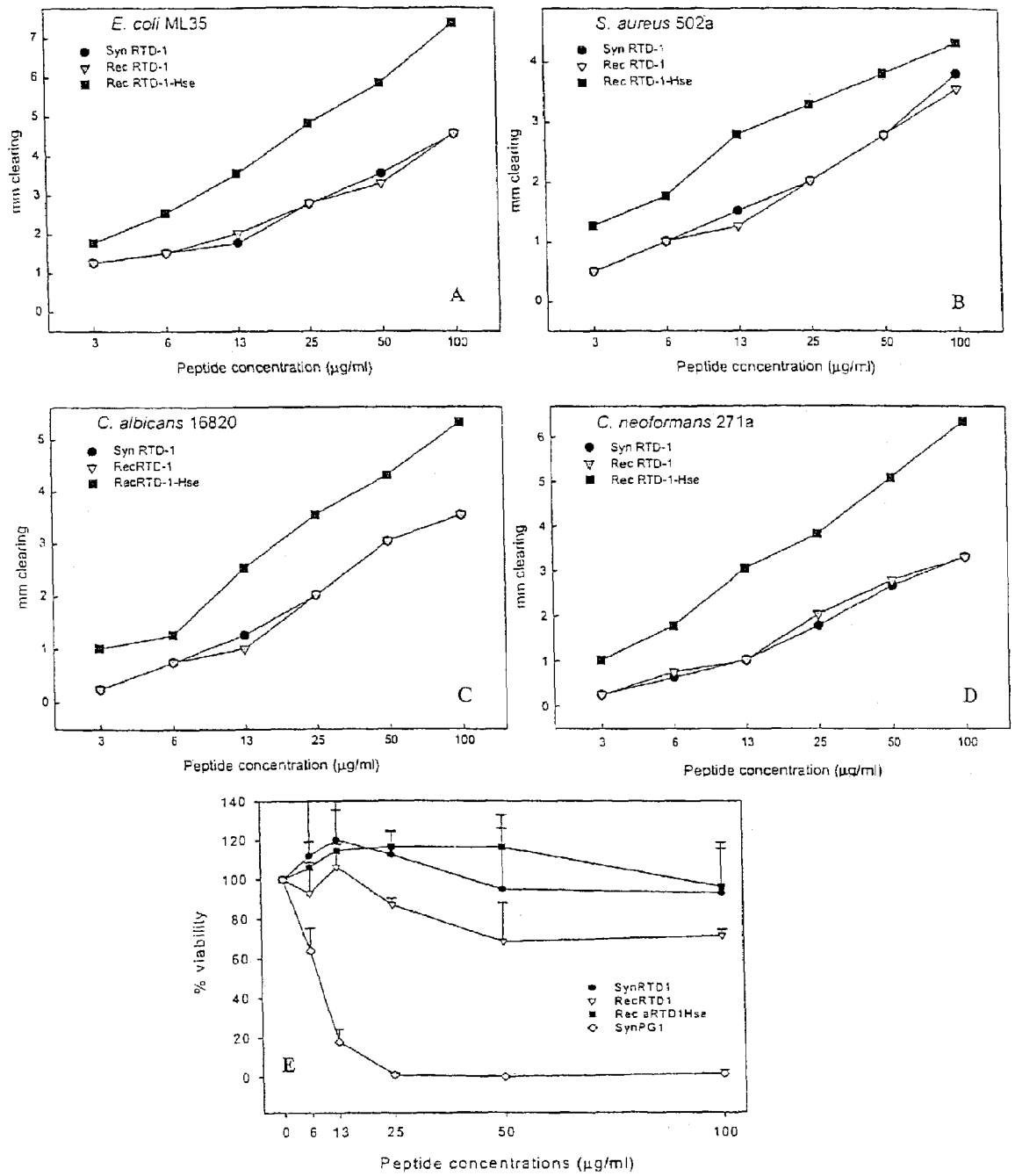
FIG. 18 shows antimicrobial activities (A–D) and cytotoxicities (E) of synthetic RTD-1, recombinant RTD-1 and aRTD-1-Hse. Antimicrobial activities of each peptide were determined in agar diffusion assays against E. coli, S. aureus, C. albicans, and C. neoformans. (E) Cytotoxicity of each peptide was determined by measuring viability of HS68 cells ($5\times10^3$) after 1-h exposure to increasing concentrations of synthetic and recombinant RTD-1, RTD-1-Hse, and PG-1 in 100 μl Dulbecco's modified Eagle media (DMEM) containing 0.4% fetal bovine serum.

Recombinant Expression of RTD-1 and a Homoserine Analog with Enhanced Antimicrobial Activities Structure-function studies revealed that amidation of the carboxyl termini enhanced microbicidal function of acyclic θ-defensins without significantly affecting the peptide cytocidal selectivities. RTD-1 was expressed as a His-Tag fusion protein in *E. coli* to test the hypothesis that the peptide is producible in a bacterial recombinant system. Furthermore, a tandem repeat of RTD-1 containing a single methionine residue allows simultaneous yield of a linear version of RTD-1 and a homoserine analog (RTD-1-Hse) after cleavage of the expressed protein with cyanogen bromide (FIG. 17). Linear versions of the recombinant RTD-1 and RTD-1-Hse were purified by $C_{18}$ reversed-phase HPLC and air oxidized to form the disulfide bonds and the peptides were purified to homogeneity. Cyclization of the acyclic RTD-1 was performed using the EDC/HOBt protocol established for the synthesis of RTD-1.

The antimicrobial activities of recombinant and synthetic versions of RTD-1, and RTD-1-Hse against *E. coli, S. aureus, C. albicans,* and *C. neoformans* were compared in agar diffusion assays. The antimicrobial activities of recombinant and synthetic RTD-1 were virtually indistinguishable (FIGS. 18A–D). The acyclic analog RTD-1-Hse appears more antimicrobial than native RTD-1, suggesting that the additional homoserine residue enhances antimicrobial function. The peptide cytotoxicities for HS68 cells were also evaluated in the MTT-cytotoxicity assays (Li and Zhang, *Toxicology in Vitro* 15:643–647 (2001)). Like synthetic RTD-1, recombinant RTD-1 and aRTD-1-Hse were non-cytotoxic for human fibroblasts with ≧68.4% of HS68 cells remained viable after incubation with up to 100 μg/ml of each peptide (FIG. 18E), while PG-1 completely ablated the HS68 at 25 μg/ml and higher peptide concentrations.

EXAMPLE V

Anti-Inflammatory Activity of Theta Defensins

This example describes anti-inflammatory activity of RTD-1.

The anti-inflammatory properties of RTD-1 were evaluated by determining the relative levels of cytokines produced by stimulated white blood cells. Blood was obtained from healthy donors in accordance with institutional guidelines. Serum was prepared from the same donor following coagulation and high-speed centrifugation (12,000–15,000× g). White blood cells (WBC) were prepared from EDTA anti-coagulated blood using an established protocol. WBC were suspended in RPMI 1640 (Gibco; Invitrogen, Carlsbad Calif.) containing 10% FBS and 1% autologous serum. Aliquots containing $2 \times 10^6$ cells were added to each well of a sterile 12-well plate, and cells were allowed to incubate for 18 h at 37° C. in a humidified incubator with 5% carbon dioxide. *Salmonella* minnesota-derived LPS (Sigma; St. Louis Mo.) or RTD-1 were re-suspended in RPMI 1640 and added to final concentrations of 100 ng/ml in triplicate wells and incubated for 18 h. Cell-free supernatants were collected by centrifugation at 12,000×g and incubated with cytokine-antibody arrays per the manufacturer's protocol (RayBiotech; Norcross Ga.). The cytokines on each array were visualized with a chemi luminescent kit (Pierce; Rockford Ill.) and enumerated by spot density analysis with Chemi-Imager 5.5 (Alpha Innotech; San Leandro Calif.). Cytokine levels are expressed as fold increase relative to those from control supernatants, where LPS and RTD-1 were omitted.

The effect of RTD-1 on cytokine expression is shown in Table 6. The release of inflammatory cytokines by white blood cells are indicative of immune activation in response to bacterial endotoxin. LPS was used to stimulate white blood cells in an ex vivo model, and the cytokine production was quantified by an antibody microarray system. LPS was found to stimulate the production of several cytokines including tumor necrosis factor-α, several interleukins (IL-1β, 2, 5, 6, 7, and 10), several chemokines (MIP-1-δ, RANTES) and growth stimulatory factors (GM-CSF, SCF, and TGF-β1). The addition of RTD-1 appears to reduce levels of many cytokines that are released by LPS-stimulated cells, indicating that RTD-1 can play a role during an inflammatory response. Reduction of pro-inflammatory cytokines such as TNF-A and IL-1β by RTD-1 indicates the anti-inflammatory property of the peptide is mediated through the regulation of cytokine production.

TABLE 6

| Cytokine | Fold increase | | Stimulus |
|---|---|---|---|
| | + | + | LPS (100 ng/ml) |
| | | + | + | RTD-1 (100 ng/ml) |
| ENA-78 | 16 | 1 | 10 |
| GCSF | 60 | 1 | 1 |
| GM-CSF | 237 | 1 | 1 |
| GRO | 24 | 4 | 19 |
| IFN-γ | 355 | 1 | 60 |
| IL-10 | 4 | 1 | 2 |
| IL-1β | 414 | 178 | 118 |
| IL-2 | 60 | 1 | 1 |
| IL-5 | 933 | 60 | 118 |
| IL-6 | 3 | 2 | 2 |
| IL-7 | 3 | 1 | 1 |
| MCP-2 | 5 | 2 | 4 |
| MCSF | 118 | 60 | 1 |
| MDC | 8 | 2 | 4 |
| MIP-1-δ | 237 | 1 | 1 |
| RANTES | 593 | 1 | 237 |
| SCF | 237 | 1 | 1 |
| SDF-1 | 533 | 1 | 178 |
| TARC | 178 | 1 | 60 |
| TGF-β1 | 119 | 1 | 1 |
| TNF-α | 237 | 1 | 1 |

This example demonstrates that theta defensins have anti-inflammatory activity.

Throughout this application various publications have been referenced. The disclosures of these publications in their entireties are hereby incorporated by reference in this application in order to more fully describe the state of the art to which this invention pertains. Although the invention has been described with reference to the examples provided above, it should be understood that various modifications can be made without departing from the spirit of the invention.

What is claimed is:

1. A theta defensin analog comprising SEQ ID NO:25.

2. A pharmaceutical composition, comprising the theta defensin analog of claim 1 and a pharmaceutically acceptable carrier.

3. A method of reducing or inhibiting growth or survival of a microorganism in an environment capable of sustaining the growth or survival of the microorganism, comprising administering an effective amount of the theta defensin analog claim 1 to said environment, thereby reducing or inhibiting of the growth or survival of the microorganism.

4. The method of claim 3, wherein said environment is a food or food product.

5. The method of claim 3, wherein said environment is a solution.

6. The method of claim 5, wherein said solution is a contact lens solution.

7. The method of claim 5, wherein said solution is an eye wash solution.

8. The method of claim 3, wherein said environment is an inanimate object comprising a surface.

9. The method of claim 3, wherein said environment is a mammal.

10. The method of claim 3, wherein said administration is topical.

11. The method of claim 3, wherein said administration is by injection.

12. The method of claim 3, wherein said administration is oral.

* * * * *